United States Patent
Vogt et al.

(10) Patent No.: US 10,420,341 B2
(45) Date of Patent: Sep. 24, 2019

(54) HERBICIDAL PHENYLPYRIMIDINES

(71) Applicant: BASF SE, Ludwigshafen am Rhein (DE)

(72) Inventors: Florian Vogt, Mannheim (DE); Matthias Witschel, Bad Duerkheim (DE); Thomas Seitz, Viernheim (DE); Anna Aleksandra Michrowska-Pianowska, Mannheim (DE); Liliana Parra Rapado, Offenburg (DE); Richard Evans, Raleigh, NC (US); Gerd Kraemer, Kerzenheim (DE); Trevor William Newton, Neustadt (DE); Kristin Hanzlik, Bobenheim am Berg (DE); Doreen Schachtschabel, Mannheim (DE); Klaus Kreuz, Denzlingen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/546,832

(22) PCT Filed: Jan. 28, 2016

(86) PCT No.: PCT/EP2016/051741
§ 371 (c)(1),
(2) Date: Jul. 27, 2017

(87) PCT Pub. No.: WO2016/120355
PCT Pub. Date: Aug. 4, 2016

(65) Prior Publication Data
US 2018/0271094 A1    Sep. 27, 2018

(30) Foreign Application Priority Data

Jan. 30, 2015 (EP) .................................. 15153269

(51) Int. Cl.
| | |
|---|---|
| *A01N 43/54* | (2006.01) |
| *C07D 405/04* | (2006.01) |
| *C07D 239/30* | (2006.01) |
| *C07D 239/34* | (2006.01) |
| *C07D 239/38* | (2006.01) |
| *C07D 239/42* | (2006.01) |
| *C07D 401/04* | (2006.01) |
| *C07D 239/28* | (2006.01) |

(52) U.S. Cl.
CPC ........... *A01N 43/54* (2013.01); *C07D 239/28* (2013.01); *C07D 239/30* (2013.01); *C07D 239/34* (2013.01); *C07D 239/38* (2013.01); *C07D 239/42* (2013.01); *C07D 401/04* (2013.01); *C07D 405/04* (2013.01)

(58) Field of Classification Search
CPC .... A01N 43/54; C07D 239/30; C07D 239/34; C07D 239/38; C07D 239/42; C07D 239/28; C07D 401/04; C07D 405/04
See application file for complete search history.

(56) References Cited

U.S. PATENT DOCUMENTS

| | | |
|---|---|---|
| 2007/0208056 A1 | 9/2007 | Carter et al. |
| 2011/0183979 A1 | 7/2011 | Bleicher et al. |
| 2011/0306589 A1 | 12/2011 | Bleicher et al. |
| 2014/0350251 A1 | 11/2014 | Clark et al. |

FOREIGN PATENT DOCUMENTS

| | | | |
|---|---|---|---|
| CN | 103980206 A | | 8/2014 |
| EP | 136976 | * | 4/1985 |
| WO | WO-00/73278 | | 12/2000 |
| WO | WO-2006/004532 | | 1/2006 |
| WO | WO-2011/130628 | | 10/2011 |
| WO | WO-2013/165854 | | 11/2013 |
| WO | WO-2014/187705 | | 11/2014 |
| WO | WO-2015/052152 | | 4/2015 |

(Continued)

OTHER PUBLICATIONS

Derwent abstract 1985-088770; abstracting EP 136976 (Apr. 1985).*

(Continued)

*Primary Examiner* — John Pak
(74) *Attorney, Agent, or Firm* — Brinks Gilson & Lione

(57) ABSTRACT

The present invention relates to the use of phenylpyrimidines of formula (I)

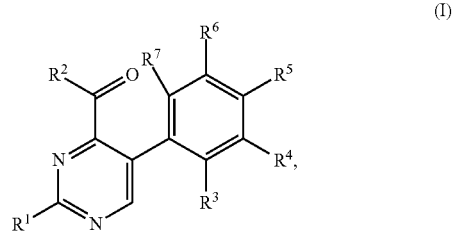

or their agriculturally acceptable salts or derivatives as herbicides, wherein the variables are defined according to the description, specific phenylpyrimidines of formula (I), processes and intermediates for preparing the phenylpyrimidines of the formula (I), compositions comprising them and their use as herbicides, i.e. for controlling harmful plants, and also a method for controlling unwanted vegetation which comprises allowing a herbicidal effective amount of at least one phenylpyrimidine of the formula (I) to act on plants, their seed and/or their habitat.

7 Claims, No Drawings

(56) References Cited

FOREIGN PATENT DOCUMENTS

| WO | WO-2015/052153 | 4/2015 |
|---|---|---|
| WO | WO-2015/158565 | 10/2015 |
| WO | WO-2016/062814 | 4/2016 |
| WO | WO-2016/120116 | 8/2016 |
| WO | WO-2016/120355 | 8/2016 |

OTHER PUBLICATIONS

Machine translation of EP 136976 (Apr. 1985).*
Brown, et al, "Characterization of a Crystalline Synthetic Analogue of Copper (II)-Bleomycin," Journal of the American Chemical Society, 1988, vol. 110, Issue 6, pp. 1996-1997.
Budesinsky, et al., "Nucleophilic Substitutions in the 2-Methanesulfonylpyrimidine Series," Collection of Czechoslovak Chemical Communications, 1972, vol. 37, Issue 5, pp. 1721-1733.
King, et al., "The Condensation of Isatin and of 1-Methylisatin with Barbituric Acid," Journal of the Chemical Society, Jan. 1948, pp. 552-556.
Pierre, et al, "Novel Potent Pyrimido[4,5-c]Quinoline Inhibitors of Protein Kinase CK2: SAR and Preliminary Assessment of their Analgesic and Anti-Viral Properties," Bioorganic & Medicinal Chemistry Letters, 2011, vol. 21, Issue 6, pp. 1687-1691.
Regan, et al., "A Facile Synthesis of 5-Halopyrimidine-4-Carboxylic Acid Esters via a Minisci Reaction," Synlett, 2012, vol. 23, Issue 3, pp. 443-447.
International Preliminary Report on Patentability dated Apr. 24, 2017 for PCT/EP2016/051741.
International Search Report dated Sep. 12, 2016 for PCT/EP2016/051741.

* cited by examiner

HERBICIDAL PHENYLPYRIMIDINES

This application is a National Stage application of International Application No. PCT/EP2016/051741, filed Jan. 28, 2016. This application also claims priority under 35 U.S.C. § 119 to European Patent Application No. 15153269.4, filed Jan. 30, 2015.

The present invention relates to phenylpyrimidines of the general formula (I) defined below and to their use as herbicides. Moreover, the invention relates to compositions for crop protection and to a method for controlling unwanted vegetation.

Compounds having a 5-phenyl pyrimidine moiety are known in the art. WO 2000/073278 describes such compounds being antagonists of the Neurokinin 1 receptor and thus having pharmaceutical properties.

In agriculture, there is a constant demand to develop novel active ingredients, which complement or outperform present methods of treatment regarding activity, selectivity and environmental safety.

These and further objects are achieved by phenylpyrimidines of formula (I), defined below, and by their agriculturally suitable salts.

Accordingly, the present invention provides the use of phenylpyrimidines of formula (I)

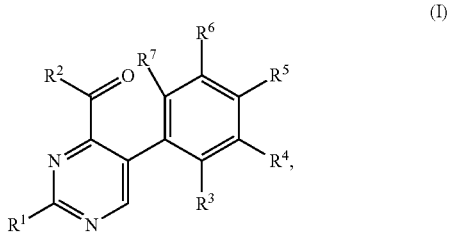

or their agriculturally acceptable salts or derivatives, provided the phenylpyrimidines of formula (I) have a carboxyl group,
as herbicides, i.e. for controlling harmful plants,
wherein in formula (I) the variables have the following meanings:

$R^1$ $C_1$-$C_6$-alkyl, $C_1$-$C_6$-haloalkyl, hydroxy-$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkinyloxy, $C_3$-$C_6$-haloalkinyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl,
$C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy,
phenyl, 5- or 6-membered heteroaryl, or 3- to 6-membered heterocyclyl wherein the cycloalkyl, phenyl, heteroaryl and heterocyclyl substituents independently of one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^2$ H, halogen, $C_1$-$C_6$-alkyl, $C_1$-$C_6$-haloalkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkylcarbonyl-$C_1$-$C_6$-alkyl, $C_1$-$C_6$-haloalkoxycarbonyl-$C_1$-$C_6$-alkyl, $C_1$-$C_6$-alkylcarbonyl-$C_1$-$C_6$-haloalkyl, $C_1$-$C_6$-alkoxycarbonyl-$C_1$-$C_6$-haloalkyl, $C_1$-$C_6$-haloalkylcarbonyl-$C_1$-$C_6$-haloalkyl, $C_1$-$C_6$-haloalkoxycarbonyl-$C_1$-$C_6$-haloalkyl, OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy, $C_1$-$C_6$-haloalkoxy, $C_1$-$C_6$-cyanoalkoxy, $C_1$-$C_6$-hydroxyalkoxy, $C_2$-$C_6$-alkenyloxy, $C_2$-$C_6$-alkenyloxy-$C_1$-$C_6$-alkoxy, $C_2$-$C_6$-haloalkenyloxy-$C_1$-$C_6$-haloalkoxy, $C_2$-$C_6$-alkenyloxy-$C_1$-$C_6$-haloalkoxy, $C_2$-$C_6$-haloalkenyloxy, $C_2$-$C_6$-alkynyloxy, $C_2$-$C_6$-haloalkynyloxy, $C_2$-$C_6$-alkynyloxy-$C_1$-$C_6$-alkoxy, $C_2$-$C_6$-haloalkynyloxy-$C_1$-$C_6$-haloalkoxy, $C_2$-$C_6$-alkynyloxy-$C_1$-$C_6$-haloalkoxy, $C_2$-$C_6$-alkynyloxy-$C_2$-$C_6$-alkenyloxy, $C_2$-$C_6$-haloalkynyloxy-$C_2$-$C_6$-alkenyloxy, $C_2$-$C_6$-alkynyloxy-$C_2$-$C_6$-haloalkenyloxy, $C_2$-$C_6$-haloalkynyloxy-$C_2$-$C_6$-haloalkenyloxy, $C_2$-$C_6$-alkynyloxy-$C_2$-$C_6$-alkynyloxy, $C_2$-$C_6$-haloalkynyloxy-$C_2$-$C_6$-alkynyloxy, $C_2$-$C_6$-alkynyloxy-$C_2$-$C_6$-haloalkynyloxy, $C_2$-$C_6$-haloalkynyloxy-$C_2$-$C_6$-haloalkynyloxy, ($C_1$-$C_6$-alkyl)carbonyl-$C_1$-$C_6$-alkoxy, ($C_1$-$C_6$-haloalkyl)carbonyl-$C_1$-$C_6$-haloalkoxy, ($C_1$-$C_6$-haloalkyl)carbonyl-$C_1$-$C_6$-alkoxy, ($C_1$-$C_6$-alkyl)carbonyl-$C_1$-$C_6$-haloalkoxy, ($C_1$-$C_6$-alkoxy)carbonyl-$C_1$-$C_6$-alkoxy, ($C_1$-$C_6$-haloalkoxy)carbonyl-$C_1$-$C_6$-alkoxy, ($C_1$-$C_6$-alkoxy)carbonyl-$C_1$-$C_6$-haloalkoxy, ($C_1$-$C_6$-haloalkoxy)carbonyl-$C_1$-$C_6$-haloalkoxy, ($C_1$-$C_6$-alkoxy-$C_1$-$C_6$-alkyl)carbonyl-$C_1$-$C_6$-alkoxy, ($C_1$-$C_6$-haloalkoxy-$C_1$-$C_6$-alkyl)carbonyl-$C_1$-$C_6$-alkoxy, ($C_1$-$C_6$-alkoxy-$C_1$-$C_6$-haloalkyl)carbonyl-$C_1$-$C_6$-alkoxy, ($C_1$-$C_6$-alkoxy-$C_1$-$C_6$-alkyl)carbonyl-$C_1$-$C_6$-haloalkoxy, ($C_1$-$C_6$-haloalkoxy-$C_1$-$C_6$-haloalkyl)carbonyl-$C_1$-$C_6$-alkoxy, ($C_1$-$C_6$-haloalkoxy-$C_1$-$C_6$-alkyl)carbonyl-$C_1$-$C_6$-haloalkoxy, ($C_1$-$C_6$-alkoxy-$C_1$-$C_6$-haloalkyl)carbonyl-$C_1$-$C_6$-haloalkoxy, ($C_1$-$C_6$-haloalkoxy-$C_1$-$C_6$-haloalkyl)carbonyl-$C_1$-$C_6$-haloalkoxy, ($C_1$-$C_6$-alkylthio)carbonyl-$C_1$-$C_6$-alkoxy, ($C_1$-$C_6$-haloalkylthio)carbonyl-$C_1$-$C_6$-alkoxy, ($C_1$-$C_6$-alkylthio)carbonyl-$C_1$-$C_6$-haloalkoxy, ($C_1$-$C_6$-haloalkylthio)carbonyl-$C_1$-$C_6$-haloalkoxy, ($C_1$-$C_6$-alkylthio-$C_1$-$C_6$-alkyl)carbonyl-$C_1$-$C_6$-alkoxy, ($C_1$-$C_6$-haloalkylthio-$C_1$-$C_6$-alkyl)carbonyl-$C_1$-$C_6$-alkoxy, ($C_1$-$C_6$-alkylthio-$C_1$-$C_6$-haloalkyl)carbonyl-$C_1$-$C_6$-alkoxy, ($C_1$-$C_6$-alkylthio-$C_1$-$C_6$-alkyl)carbonyl-$C_1$-$C_6$-haloalkoxy, ($C_1$-$C_6$-haloalkylthio-$C_1$-$C_6$-haloalkyl)carbonyl-$C_1$-$C_6$-alkoxy, ($C_1$-$C_6$-haloalkylthio-$C_1$-$C_6$-alkyl)carbonyl-$C_1$-$C_6$-haloalkoxy, ($C_1$-$C_6$-alkylthio-$C_1$-$C_6$-haloalkyl)carbonyl-$C_1$-$C_6$-haloalkoxy, ($C_1$-$C_6$-haloalkylthio-$C_1$-$C_6$-haloalkyl)carbonyl-$C_1$-$C_6$-haloalkoxy, $C_3$-$C_6$-cycloalkoxy, $C_3$-$C_6$-halocycloalkoxy, ($C_3$-$C_6$-cycloalkyl)$C_1$-$C_6$-alkoxy, ($C_3$-$C_6$-halocycloalkyl)$C_1$-$C_6$-alkoxy, ($C_3$-$C_6$-cycloalkyl)$C_1$-$C_6$-haloalkoxy, ($C_3$-$C_6$-halocycloalkyl)$C_1$-$C_6$-haloalkoxy, aminocarbonyl-$C_1$-$C_6$-alkoxy, aminocarbonyl-$C_1$-$C_6$-haloalkoxy, N—($C_1$-$C_6$-alkyl)-aminocarbonyl-$C_1$-$C_6$-alkoxy, N—($C_1$-$C_6$-alkyl)-aminocarbonyl-$C_1$-$C_6$-haloalkoxy, N,N-di($C_1$-$C_6$-alkyl)aminocarbonyl-$C_1$-$C_6$-alkoxy, N,N-di($C_1$-$C_6$-alkyl)-aminocarbonyl-$C_1$-$C_6$-haloalkoxy,
O—N=C(di(phenyl), O—N=C(phenyl)($C_1$-$C_6$-alkyl), O—N=C[di($C_1$-$C_6$-alkyl)], ($C_1$-$C_6$-alkyl)$_3$-silyl-$C_1$-$C_6$-alkoxy, $C_1$-$C_6$-alkylthio, $C_1$-$C_6$-haloalkylthio, $C_1$-$C_6$-alkoxy-$C_1$-$C_6$-alkylthio, $C_1$-$C_6$-haloalkoxy-$C_1$-$C_6$-alkylthio, $C_1$-$C_6$-alkoxy-$C_1$-$C_6$-haloalkylthio, $C_1$-$C_6$-haloalkoxy-$C_1$-$C_6$-haloalkylthio, $C_1$-$C_6$-alkoxy-$C_1$-$C_6$-alkoxy-$C_1$-$C_6$-alkylthio, $C_1$-$C_6$-cyanoalkylthio, $C_2$-$C_6$-alkenylthio, $C_2$-$C_6$-haloalkenylthio, $C_2$-$C_6$-alkenyloxy-$C_1$-$C_6$-alkylthio, $C_2$-$C_6$-haloalkenyloxy-$C_1$-$C_6$-alkylthio, $C_2$-$C_6$-alkenyloxy-$C_1$-$C_6$-haloalkylthio, $C_2$-$C_6$-haloalkenyloxy-$C_1$-$C_6$-haloalkylthio, $C_2$-$C_6$-alkynylthio, $C_2$-$C_6$-haloalkynylthio, $C_2$-$C_6$-alkynyloxy-$C_1$-$C_6$-alkylthio, $C_2$-$C_6$-haloalkynyloxy-$C_1$-$C_6$-haloalkylthio, $C_2$-$C_6$-alkynyloxy-$C_1$-$C_6$-haloalkylthio, $C_2$-$C_6$-alkynyloxy-$C_2$-$C_6$-alkenylthio, $C_2$-$C_6$-haloalkynyloxy-$C_2$-$C_6$-alkenylthio, $C_2$-$C_6$-alkynyloxy-$C_2$-$C_6$-haloalkenylthio, $C_2$-$C_6$-haloalkynyloxy-$C_2$-$C_6$-haloalkenylthio, $C_2$-$C_6$-alkynyloxy-$C_2$-$C_6$-alkynylthio, $C_2$-$C_6$-haloalkynyloxy-$C_2$-$C_6$-alkynylthio, $C_2$-$C_6$-alkynyloxy-$C_2$-$C_6$-haloalkynylthio, $C_2$-$C_6$-haloalkynyloxy-$C_2$-$C_6$-haloalkynylthio, ($C_1$-$C_6$-alkyl)carbonyl-$C_1$-$C_6$-alkylthio, ($C_1$-$C_6$-haloalkyl)carbonyl-$C_1$-$C_6$-alkylthio, ($C_1$-$C_6$-alkyl)carbonyl-$C_1$-$C_6$-haloalkylthio, ($C_1$-$C_6$-haloalkyl)carbonyl-$C_1$-$C_6$-haloalkylthio, ($C_1$-$C_6$-alkoxy)carbonyl-$C_1$-$C_6$-alkylthio, ($C_1$-$C_6$-haloalkoxy)carbonyl-$C_1$-$C_6$-alkylthio, ($C_1$-$C_6$-alkoxy)carbonyl-$C_1$-$C_6$-alkylthio, ($C_1$-$C_6$-haloalkoxy)carbonyl-$C_1$-$C_6$-haloalkylthio, ($C_1$-$C_6$-alkoxy-$C_1$-$C_6$-alkyl)carbonyl-$C_1$-$C_6$-alkylthio, ($C_1$-$C_6$-haloalkoxy-$C_1$-$C_6$-alkyl)carbonyl-$C_1$-$C_6$-alkylthio, ($C_1$-$C_6$-alkoxy-$C_1$-$C_6$-haloalkyl)carbonyl-$C_1$-$C_6$-alkylthio, ($C_1$-$C_6$-alkoxy-$C_1$-$C_6$-alkyl)carbonyl-$C_1$-$C_6$-haloalkylthio, ($C_1$-$C_6$-haloalkoxy-$C_1$-$C_6$-haloalkyl)carbonyl-$C_1$-$C_6$-alkylthio, ($C_1$-$C_6$-haloalkoxy-$C_1$-$C_6$-alkyl)carbonyl-$C_1$-$C_6$-haloalkylthio, ($C_1$-$C_6$-alkoxy-$C_1$-$C_6$-haloalkyl)carbonyl-$C_1$-$C_6$-haloalkylthio, ($C_1$-$C_6$-haloalkoxy-$C_1$-$C_6$-haloalkyl)carbonyl-$C_1$-$C_6$-haloalkylthio, ($C_1$-$C_6$-alkylthio)carbonyl-$C_1$-$C_6$-alkylthio, ($C_1$-$C_6$-haloalkylthio)carbonyl-$C_1$-$C_6$-alkylthio, ($C_1$-$C_6$-alkylthio)carbonyl-$C_1$-$C_6$-haloalkylthio, ($C_1$-$C_6$-haloalkylthio)carbonyl-$C_1$-$C_6$-haloalkylthio, ($C_1$-$C_6$-alkylthio-$C_1$-$C_6$-alkyl)carbonyl-$C_1$-$C_6$-alkylthio, ($C_1$-$C_6$-haloalkylthio-$C_1$-$C_6$-alkyl)carbonyl-$C_1$-$C_6$-alkylthio, ($C_1$-$C_6$-alkylthio-$C_1$-$C_6$-haloalkyl)carbonyl-$C_1$-$C_6$-alkylthio, ($C_1$-$C_6$-alkylthio-$C_1$-$C_6$-alkyl)carbonyl-$C_1$-$C_6$-haloalkylthio, ($C_1$-$C_6$-haloalkylthio-$C_1$-$C_6$-haloalkyl)carbonyl-$C_1$-$C_6$-alkylthio, ($C_1$-$C_6$-haloalkylthio-$C_1$-$C_6$-alkyl)carbonyl-$C_1$-$C_6$-haloalkylthio, ($C_1$-$C_6$-alkylthio-$C_1$-$C_6$-haloalkyl)carbonyl-$C_1$-$C_6$-haloalkylthio, ($C_1$-$C_6$-haloalkylthio-$C_1$-$C_6$-haloalkyl)carbonyl-$C_1$-$C_6$-haloalkylthio, $C_3$-$C_6$-cycloalkylthio, $C_3$-$C_6$-halocycloalkylthio, ($C_3$-$C_6$-cycloalkyl)$C_1$-$C_6$-alkylthio, ($C_3$-$C_6$-cycloalkyl)$C_1$-$C_6$-haloalkylthio, ($C_3$-$C_6$-halocycloalkyl)$C_1$-$C_6$-alkylthio, ($C_3$-$C_6$-halocycloalkyl)$C_1$-$C_6$-haloalkylthio, aminocarbonyl-$C_1$-$C_6$-alkylthio, aminocarbonyl-$C_1$-$C_6$-haloalkylthio, N—($C_1$-$C_6$-alkyl)-aminocarbonyl-$C_1$-$C_6$-alkylthio, N—($C_1$-$C_6$-haloalkyl)aminocarbonyl-$C_1$-$C_6$-alkylthio, N—($C_1$-$C_6$-alkyl)-aminocarbonyl-$C_1$-$C_6$-haloalkylthio, N—($C_1$-$C_6$-haloalkyl)-aminocarbonyl-$C_1$-$C_6$-haloalkylthio, N,N-di($C_1$-$C_6$-alkyl)-aminocarbonyl-$C_1$-$C_6$-alkylthio, N,N-di($C_1$-$C_6$-haloalkyl)-aminocarbonyl-$C_1$-$C_6$-alkylthio, N,N-di($C_1$-$C_6$-alkyl)aminocarbonyl-$C_1$-$C_6$-haloalkylthio, N,N-di($C_1$-$C_6$-haloalkyl)-aminocarbonyl-$C_1$-$C_6$-haloalkylthio, $NH_2$, ($C_1$-$C_6$-alkyl)amino, hydroxyamino, ($C_1$-$C_6$-alkoxy)amino, ($C_3$-$C_6$-cycloalkoxy)amino, ($C_1$-$C_6$-alkyl)sulfinylamino, ($C_1$-$C_6$-alkyl)sulfonylamino, (amino)sulfinylamino, [($C_1$-$C_6$-alkyl)amino]sulfinylamino, (amino)sulfonylamino, [($C_1$-$C_6$-alkyl)amino]sulfonylamino, [di($C_1$-$C_6$-alkyl)amino]sulfonylamino, di($C_1$-$C_6$-alkyl)amino, (hydroxy)($C_1$-$C_6$-alkyl)amino, (hydroxy)($C_1$-$C_6$-cycloalkyl)amino, ($C_1$-$C_6$-alkoxy)($C_1$-$C_6$-alkyl)amino, ($C_1$-$C_6$-alkoxy)($C_3$-$C_6$-cycloalkyl)amino, ($C_3$-$C_6$-cycloalkoxy)($C_1$-$C_6$-alkyl)amino, ($C_3$-$C_6$-cycloalkoxy)($C_3$-$C_6$-cycloalkyl)amino, [($C_1$-$C_6$-alkyl)sulfinyl]($C_1$-$C_6$-alkyl)amino, [($C_1$-$C_6$-alkyl)sulfonyl]($C_1$-$C_6$-alkyl)amino, [di($C_1$-$C_6$-alkyl)amino]sulfinylamino, [di($C_1$-$C_6$-alkyl)amino]sulfonylamino, phenyloxy, phenyl-$C_1$-$C_6$-alkoxy, phenylthio, phenyl-$C_1$-$C_6$-alkylthio, phenylamino, ($C_1$-$C_6$-alkyl)(phenyl)amino, (heteroaryl)oxy, heteroaryl-$C_1$-$C_6$-alkoxy, (heterocyclyl)oxy, heterocyclyl-$C_1$-$C_6$-alkoxy, wherein the phenyl, heteroaryl and heterocyclyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^3$ halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkinyl, $C_2$-$C_6$-haloalkinyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkinyloxy, $C_2$-$C_6$-haloalkinyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

and $R^4$, $R^5$, $R^6$ and $R^7$ independently of one another

H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkinyl, $C_2$-$C_6$-haloalkinyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkinyloxy, $C_2$-$C_6$-haloalkinyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy.

The present invention also provides agrochemical compositions comprising at least one phenylpyrimidine of formula (I) and auxiliaries customary for formulating crop protection agents.

The present invention furthermore provides a method for controlling unwanted vegetation where a herbicidal effective amount of at least one phenylpyrimidine of formula (I) is allowed to act on plants, their seeds and/or their habitat. Application can be done before, during and/or after, preferably during and/or after, the emergence of the undesirable plants.

The present invention also provides phenylpyrimidines of formula (I) as described herein.

Moreover, the invention relates to processes and intermediates for preparing phenylpyrimidines of formula (I).

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation" and "harmful plants" are synonyms.

If the phenylpyrimidines of formula (I) as described herein are capable of forming geometrical isomers, for example E/Z isomers, it is possible to use both, the pure isomers and mixtures thereof, in the compositions according to the invention.

If the phenylpyrimidines of formula (I) as described herein have one or more centres of chirality and, as a consequence, are present as enantiomers or diastereomers, it is possible to use both, the pure enantiomers and diastereomers and their mixtures, in the compositions according to the invention.

If the phenylpyrimidines of formula (I) as described herein have ionisable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Phenylpyrimidines of formula (I) as described herein having a carboxyl group can be employed, if applicable, in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl) methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

The organic moieties mentioned in the definition of the variables $R^1$ to $R^7$, are—like the term halogen—collective terms for individual enumerations of the individual group members. The term halogen denotes in each case fluorine, chlorine, bromine or iodine. All hydrocarbon chains, for example all alkyl, alkenyl, alkynyl, alkoxy chains can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: $C_1$-$C_4$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

C$_3$-C$_6$-cycloalkyl: monocyclic saturated hydrocarbons having 3 to 6 ring members, such as cyclopropyl, cyclobutyl, cyclopentyl and cyclohexyl;

C$_2$-C$_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

C$_2$-C$_6$-haloalkenyl: a C$_2$-C$_6$-alkenyl substituent as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

C$_3$-C$_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

C$_2$-C$_6$-alkynyl: C$_3$-C$_6$-alkynyl as mentioned above and also ethynyl;

C$_3$-C$_6$-haloalkynyl: a C$_3$-C$_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

C$_1$-C$_4$-alkoxy: for example methoxy, ethoxy, propoxy, 1-methylethoxy butoxy, 1-methylpropoxy, 2-methylpropoxy and 1,1-dimethylethoxy;

C$_1$-C$_6$-alkoxy: C$_1$-C$_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

C$_1$-C$_4$-haloalkoxy: a C$_1$-C$_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

C$_1$-C$_6$-haloalkoxy: a C$_1$-C$_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

C$_1$-C$_4$-alkylthio: for example methylthio, ethylthio, propylthio, 1-methylethylthio, butylthio, 1-methylpropylthio, 2-methylpropylthio and 1,1-dimethylethylthio;

C$_1$-C$_6$-alkylthio: C$_1$-C$_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

(C$_1$-C$_4$-alkyl)amino: for example methylamino, ethylamino, propylamino, 1-methylethylamino, butylamino, 1-methylpropylamino, 2-methylpropylamino or 1,1-dimethylethylamino;

(C$_1$-C$_6$-alkyl)amino: (C$_1$-C$_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

$C_1$-$C_6$-alkylsulfinyl ($C_1$-$C_6$-Alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentyl-sulfinyl, 1,1-dimethylbutylsulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_3$-$C_6$-cycloalkyl: a monocyclic saturated hydrocarbon having 3 to 6 ring members, such as cyclopropyl, cyclobutyl, cyclopentyl and cyclohexyl;

$C_3$-$C_6$-cycloalkenyl: 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl;

heterocyclyl: a 3- to 6-membered heterocyclyl: a saturated or partial unsaturated cycle having three to six ring members which comprises apart from carbon atoms one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, for example three- or four-membered heterocycles like 2-oxiranyl, 2-aziridinyl, 2-thiiranyl, 2-oxetanyl, 3-oxetanyl, 2-thietanyl, 3-thietanyl, 1-azetidinyl, 2-azetidinyl, 1-azetinyl, 2-azetinyl; five-membered saturated heterocycles like 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 3-oxazolidinyl, 1,2,4-oxadiazolidin-3-yl, 1,2,4-oxadiazolidin-5-yl, 3-thiazolidinyl, 1,2,4-thiadiazolidin-3-yl, 1,2,4-thiadiazolidin-5-yl, 1,2,4-triazolidin-3-yl, 1,2,4-oxadiazolidin-2-yl, 1,2,4-oxadiazolidin-4-yl, 1,3,4-oxadiazolidin-2-yl, 1,2,4-thiadiazolidin-2-yl, 1,2,4-thiadiazolidin-4-yl, 1,3,4-thiadiazolidin-2-yl, 1,2,4-triazolidin-1-yl, 1,3,4-triazolidin-2-yl; five-membered partial unsaturated heterocycles like 2,3-dihydrofur-2-yl, 2,3-dihydrofur-3-yl, 2,4-dihydrofur-2-yl, 2,4-dihydrofur-3-yl, dioxolan-2-yl, 1,3-dioxol-2-yl, 2,3-dihydrothien-2-yl, 2,3-dihydrothien-3-yl, 2,4-dihydrothien-2-yl, 2,4-dihydrothien-3-yl, 4,5-dihydropyrrol-1-yl, 4,5-dihydropyrrol-2-yl, 4,5-dihydropyrrol-3-yl, 2,5-dihydropyrrol-1-yl, 2,5-dihydropyrrol-2-yl, 2,5-dihydropyrrol-3-yl, 2,3-dihydroisoxazol-1-yl, 2,3-dihydroisoxazol-3-yl, 2,3-dihydroisoxazol-4-yl, 2,3-dihydroisoxazol-5-yl, 2,5-dihydroisoxazol-3-yl, 2,5-dihydroisoxazol-4-yl, 2,5-dihydroisoxazol-5-yl, 4,5-dihydroisoxazol-2-yl, 4,5-dihydroisoxazol-3-yl, 4,5-dihydroisoxazol-4-yl, 4,5-dihydroisoxazol-5-yl, 2,3-dihydroisothiazol-1-yl, 2,3-dihydroisothiazol-3-yl, 2,3-dihydroisothiazol-4-yl, 2,3-dihydroisothiazol-5-yl, 2,5-dihydroisothiazol-3-yl, 2,5-dihydroisothiazol-4-yl, 2,5-dihydroisothiazol-5-yl, 4,5-dihydroisothiazol-1-yl, 4,5-dihydroisothiazol-3-yl, 4,5-dihydroisothiazol-4-yl, 4,5-dihydroisothiazol-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydroimidazol-1-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-1-yl, 4,5-dihydroimidazol-2-yl, 4,5-dihydroimidazol-4-yl, 4,5-dihydroimidazol-5-yl, 2,5-dihydroimidazol-1-yl, 2,5-dihydroimidazol-2-yl, 2,5-dihydroimidazol-4-yl, 2,5-dihydroimidazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2,3-dihydrothiazol-2-yl, 2,3-dihydrothiazol-3-yl, 2,3-dihydrothiazol-4-yl, 2,3-dihydrothiazol-5-yl, 3,4-dihydrothiazol-2-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl;

six-membered saturated heterocycles like 1-piperidinyl, 2-piperidinyl, 3-piperidinyl, 4-piperidinyl, 1,3-dioxan-5-yl, 1,4-dioxanyl, 1,3-dithian-5-yl, 1,3-dithianyl, 1,3-oxathian-5-yl, 1,4-oxathianyl, 2-tetrahydropyranyl, 3-tetrahydopyranyl, 4-tetrahydropyranyl, 2-tetrahydrothiopyranyl, 3-tetrahydrothiopyranyl, 4-tetrahydrothiopyranyl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl, 1,3,5-hexahydrotriazin-1-yl, 1,3,5-hexahydrotriazin-2-yl, 1,2,4-hexahydrotriazin-1-yl, 1,2,4-hexahydrotriazin-3-yl, tetrahydro-1,3-oxazin-1-yl, tetrahydro-1,3-oxazin-2-yl, tetrahydro-1,3-oxazin-6-yl, 1-morpholinyl, 2-morpholinyl, 3-morpholinyl;

six-membered partial unsaturated heterocycles like 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl.

heteroaryl: a 5- or 6-membered heteroaryl: monocyclic aromatic heteroaryl having 5 to 6 ring members which, in addition to carbon atoms, contains 1 to 4 nitrogen atoms, or 1 to 3 nitrogen atoms and an oxygen or sulfur atom, or an oxygen or a sulfur atom, for example 5-membered aromatic rings like furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazole-2-yl, imidazole-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl); 1-tetrazolyl; 6-membered aromatic rings like pyridyl (for example pyridine-2-yl, pyridine-3-yl, pyridine-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl);

The preferred embodiments of the invention mentioned herein below have to be understood as being preferred either independently from each other or in combination with one another.

In general, phenylpyrimidines of formula (I) are suitable as herbicides.

According to a preferred embodiment of the invention preference is given to the use as herbicides of those phenylpyrimidines of formula (I), wherein the variables, either independently of one another or in combination with one another, have the following meanings:

Preferred is the use as herbicides of the phenylpyrimidines of formula (I), wherein the variables have the following meanings:

$R^1$ $C_1$-$C_6$-alkyl, $C_1$-$C_6$-haloalkyl, hydroxy-$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_1$-$C_6$-haloalkoxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, phenyl, 5- or 6-membered heteroaryl, or 3- to 6-membered heterocyclyl wherein the cycloalkyl, phenyl, heteroaryl and heterocyclyl substituents independently of one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^2$ H, halogen, $C_1$-$C_6$-alkyl, $C_1$-$C_6$-haloalkyl,

OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy, $C_1$-$C_6$-haloalkoxy, $C_1$-$C_6$-cyanoalkoxy, $C_1$-$C_6$-hydroxyalkoxy, $C_2$-$C_6$-alkenyloxy, $C_2$-$C_6$-alkenyloxy-$C_1$-$C_6$-alkoxy, $C_2$-$C_6$-haloalkenyloxy-$C_1$-$C_6$-haloalkoxy, $C_2$-$C_6$-alkenyloxy-$C_1$-$C_6$-haloalkoxy, $C_2$-$C_6$-haloalkenyloxy, $C_2$-$C_6$-alkynyloxy, $C_2$-$C_6$-haloalkynyloxy, $C_2$-$C_6$-alkynyloxy-$C_1$-$C_6$-alkoxy, $C_2$-$C_6$-haloalkynyloxy-$C_1$-$C_6$-haloalkoxy, $C_2$-$C_6$-alkynyloxy-$C_1$-$C_6$-haloalkoxy, $C_2$-$C_6$-alkynyloxy-$C_2$-$C_6$-alkenyloxy, $C_2$-$C_6$-haloalkynyloxy-$C_2$-$C_6$-alkenyloxy, $C_2$-$C_6$-alkynyloxy-$C_2$-$C_6$-haloalkenyloxy, $C_2$-$C_6$-haloalkynyloxy-$C_2$-$C_6$-haloalkenyloxy, $C_2$-$C_6$-alkynyloxy-$C_2$-$C_6$-alkynyloxy, $C_2$-$C_6$-haloalkynyloxy-$C_2$-$C_6$-alkynyloxy, $C_2$-$C_6$-alkynyloxy-$C_2$-$C_6$-haloalkynyloxy, $C_2$-$C_6$-haloalkynyloxy-$C_2$-$C_6$-haloalkynyloxy, ($C_1$-$C_6$-alkyl)carbonyl-$C_1$-$C_6$-alkoxy, ($C_1$-$C_6$-haloalkyl)carbonyl-$C_1$-$C_6$-haloalkoxy, ($C_1$-$C_6$-haloalkyl)carbonyl-$C_1$-$C_6$-alkoxy, ($C_1$-$C_6$-alkyl)carbonyl-$C_1$-$C_6$-haloalkoxy, ($C_1$-$C_6$-alkoxy)carbonyl-$C_1$-$C_6$-alkoxy, ($C_1$-$C_6$-haloalkoxy)carbonyl-$C_1$-$C_6$-alkoxy, ($C_1$-$C_6$-alkoxy)carbonyl-$C_1$-$C_6$-haloalkoxy, ($C_1$-$C_6$-haloalkoxy)carbonyl-$C_1$-$C_6$-haloalkoxy, ($C_1$-$C_6$-alkoxy-$C_1$-$C_6$-alkyl)carbonyl-$C_1$-$C_6$-alkoxy, ($C_1$-$C_6$-haloalkoxy-$C_1$-$C_6$-alkyl)carbonyl-$C_1$-$C_6$-alkoxy, ($C_1$-$C_6$-alkoxy-$C_1$-$C_6$-haloalkyl)carbonyl-$C_1$-$C_6$-alkoxy, ($C_1$-$C_6$-alkoxy-$C_1$-$C_6$-alkyl)carbonyl-$C_1$-$C_6$-haloalkoxy, ($C_1$-$C_6$-haloalkoxy-$C_1$-$C_6$-haloalkyl)carbonyl-$C_1$-$C_6$-alkoxy, ($C_1$-$C_6$-haloalkoxy-$C_1$-$C_6$-alkyl)carbonyl-$C_1$-$C_6$-haloalkoxy, ($C_1$-$C_6$-alkoxy-$C_1$-$C_6$-haloalkyl)carbonyl-$C_1$-$C_6$-haloalkoxy, ($C_1$-$C_6$-haloalkoxy-$C_1$-$C_6$-haloalkyl)carbonyl-$C_1$-$C_6$-haloalkoxy, ($C_1$-$C_6$-alkylthio)carbonyl-$C_1$-$C_6$-alkoxy, ($C_1$-$C_6$-haloalkylthio)carbonyl-$C_1$-$C_6$-alkoxy, ($C_1$-$C_6$-alkylthio)carbonyl-$C_1$-$C_6$-haloalkoxy, ($C_1$-$C_6$-haloalkylthio)carbonyl-$C_1$-$C_6$-haloalkoxy, ($C_1$-$C_6$-alkylthio-$C_1$-$C_6$-alkyl)carbonyl-$C_1$-$C_6$-alkoxy, ($C_1$-$C_6$-haloalkylthio-$C_1$-$C_6$-alkyl)carbonyl-$C_1$-$C_6$-alkoxy, ($C_1$-$C_6$-alkylthio-$C_1$-$C_6$-haloalkyl)carbonyl-$C_1$-$C_6$-alkoxy, ($C_1$-$C_6$-alkylthio-$C_1$-$C_6$-alkyl)carbonyl-$C_1$-$C_6$-haloalkoxy, ($C_1$-$C_6$-haloalkylthio-$C_1$-$C_6$-haloalkyl)carbonyl-$C_1$-$C_6$-alkoxy, ($C_1$-$C_6$-haloalkylthio-$C_1$-$C_6$-alkyl)carbonyl-$C_1$-$C_6$-haloalkoxy, ($C_1$-$C_6$-alkylthio-$C_1$-$C_6$-haloalkyl)carbonyl-$C_1$-$C_6$-haloalkoxy, ($C_1$-$C_6$-haloalkylthio-$C_1$-$C_6$-haloalkyl)carbonyl-$C_1$-$C_6$-haloalkoxy, $C_3$-$C_6$-cycloalkoxy, ($C_3$-$C_6$-cycloalkyl)$C_1$-$C_6$-alkoxy, ($C_3$-$C_6$-cycloalkyl)$C_1$-$C_6$-haloalkoxy, aminocarbonyl-$C_1$-$C_6$-alkoxy, aminocarbonyl-$C_1$-$C_6$-haloalkoxy, N—($C_1$-$C_6$-alkyl)-aminocarbonyl-$C_1$-$C_6$-alkoxy, N—($C_1$-$C_6$-alkyl)-aminocarbonyl-$C_1$-$C_6$-haloalkoxy, N,N-di($C_1$-$C_6$-alkyl)-aminocarbonyl-$C_1$-$C_6$-alkoxy, N,N-di($C_1$-$C_6$-alkyl)-aminocarbonyl-$C_1$-$C_6$-haloalkoxy, O—N=C(di(phenyl), O—N=C(phenyl)($C_1$-$C_6$-alkyl), O—N=C[di($C_1$-$C_6$-alkyl)], ($C_1$-$C_6$-alkyl)$_3$-silyl-$C_1$-$C_6$-alkoxy, $C_1$-$C_6$-alkylthio, $C_1$-$C_6$-haloalkylthio, $C_1$-$C_6$-alkoxy-$C_1$-$C_6$-alkylthio, $C_1$-$C_6$-haloalkoxy-$C_1$-$C_6$-alkylthio, $C_1$-$C_6$-alkoxy-$C_1$-$C_6$-haloalkylthio, $C_1$-$C_6$-haloalkoxy-$C_1$-$C_6$-alkoxy-$C_1$-$C_6$-alkylthio, $C_1$-$C_6$-cyanoalkylthio, $C_2$-$C_6$-alkenylthio, $C_2$-$C_6$-haloalkenylthio, $C_2$-$C_6$-alkenyloxy-$C_1$-$C_6$-alkylthio, $C_2$-$C_6$-haloalkenyloxy-$C_1$-$C_6$-alkylthio, $C_2$-$C_6$-alkenyloxy-$C_1$-$C_6$-haloalkylthio, $C_2$-$C_6$-haloalkenyloxy-$C_1$-$C_6$-haloalkylthio, $C_2$-$C_6$-alkynylthio, $C_2$-$C_6$-haloalkynylthio, $C_2$-$C_6$-alkynyloxy-$C_1$-$C_6$-alkylthio, $C_2$-$C_6$-haloalkynyloxy-$C_1$-$C_6$-haloalkylthio, $C_2$-$C_6$-alkynyloxy-$C_1$-$C_6$-haloalkylthio, $C_2$-$C_6$-alkynyloxy-$C_2$-$C_6$-alkenylthio, $C_2$-$C_6$-haloalkynyloxy-$C_2$-$C_6$-alkenylthio, $C_2$-$C_6$-alkynyloxy-$C_2$-$C_6$-haloalkenylthio, $C_2$-$C_6$-haloalkynyloxy-$C_2$-$C_6$-haloalkenylthio, $C_2$-$C_6$-alkynyloxy-$C_2$-$C_6$-alkynylthio, $C_2$-$C_6$-haloalkynyloxy-$C_2$-$C_6$-alkynylthio, $C_2$-$C_6$-alkynyloxy-$C_2$-$C_6$-haloalkynylthio, $C_2$-$C_6$-haloalkynyloxy-$C_2$-$C_6$-haloalkynylthio, ($C_1$-$C_6$-alkyl)carbonyl-$C_1$-$C_6$-alkylthio, ($C_1$-$C_6$-haloalkyl)carbonyl-$C_1$-$C_6$-alkylthio, ($C_1$-$C_6$-alkyl)carbonyl-$C_1$-$C_6$-haloalkylthio, ($C_1$-$C_6$-haloalkyl)carbonyl-$C_1$-$C_6$-haloalkylthio, ($C_1$-$C_6$-alkoxy)carbonyl-$C_1$-$C_6$-alkylthio, ($C_1$-$C_6$-haloalkoxy)carbonyl-$C_1$-$C_6$-alkylthio, ($C_1$-$C_6$-alkoxy)carbonyl-$C_1$-$C_6$-haloalkylthio, ($C_1$-$C_6$-haloalkoxy)carbonyl-$C_1$-$C_6$-haloalkylthio, ($C_1$-$C_6$-alkoxy-$C_1$-$C_6$-alkyl)carbonyl-$C_1$-$C_6$-alkylthio, ($C_1$-$C_6$-haloalkoxy-$C_1$-$C_6$-alkyl)carbonyl-$C_1$-$C_6$-alkylthio, ($C_1$-$C_6$-alkoxy-$C_1$-$C_6$-haloalkyl)carbonyl-$C_1$-$C_6$-alkylthio, ($C_1$-$C_6$-alkoxy-$C_1$-$C_6$-alkyl)carbonyl-$C_1$-$C_6$-haloalkylthio, ($C_1$-$C_6$-haloalkoxy-$C_1$-$C_6$-haloalkyl)carbonyl-$C_1$-$C_6$-alkylthio, ($C_1$-$C_6$-haloalkoxy-$C_1$-$C_6$-alkyl)carbonyl-$C_1$-$C_6$-haloalkylthio, ($C_1$-$C_6$-alkoxy-$C_1$-$C_6$-haloalkyl)carbonyl-$C_1$-$C_6$-haloalkylthio, ($C_1$-$C_6$-haloalkoxy-$C_1$-$C_6$-haloalkyl)carbonyl-$C_1$-$C_6$-haloalkylthio, ($C_1$-$C_6$-alkylthio)carbonyl-$C_1$-$C_6$-alkylthio, ($C_1$-$C_6$-haloalkylthio)carbonyl-$C_1$-$C_6$-alkylthio, ($C_1$-$C_6$-alkylthio)carbonyl-$C_1$-$C_6$-haloalkylthio, ($C_1$-$C_6$-haloalkylthio)carbonyl-$C_1$-$C_6$-haloalkylthio, ($C_1$-$C_6$-alkylthio-$C_1$-$C_6$-alkyl)carbonyl-$C_1$-$C_6$-alkylthio, ($C_1$-$C_6$-haloalkylthio-$C_1$-$C_6$-alkyl)carbonyl-$C_1$-$C_6$-alkylthio, ($C_1$-$C_6$-alkylthio-$C_1$-$C_6$-haloalkyl)carbonyl-$C_1$-$C_6$-alkylthio, ($C_1$-$C_6$-alkylthio-$C_1$-$C_6$-alkyl)carbonyl-$C_1$-$C_6$-haloalkylthio, ($C_1$-$C_6$-haloalkylthio-$C_1$-$C_6$-alkyl)carbonyl-$C_1$-$C_6$-haloalkylthio, ($C_1$-$C_6$-alkylthio-$C_1$-$C_6$-haloalkyl)carbonyl-$C_1$-$C_6$-haloalkylthio, ($C_1$-$C_6$-alkylthio-$C_1$-$C_6$-haloalkyl)carbonyl-$C_1$-$C_6$-alkylthio, ($C_1$-$C_6$-haloalkylthio-$C_1$-$C_6$-haloalkyl)carbonyl-$C_1$-$C_6$-haloalkylthio, $C_3$-$C_6$-cycloalkylthio, ($C_3$-$C_6$-cycloalkyl)$C_1$-$C_6$-alkylthio, ($C_3$-$C_6$-cycloalkyl)$C_1$-$C_6$-haloalkylthio, aminocarbonyl-$C_1$-$C_6$-alkylthio, aminocarbonyl-$C_1$-$C_6$-haloalkylthio, N—($C_1$-$C_6$-alkyl)-aminocarbonyl-$C_1$-$C_6$-alkylthio, N—($C_1$-$C_6$-haloalkyl)-aminocarbonyl-$C_1$-$C_6$-alkylthio, N—($C_1$-$C_6$-alkyl)aminocarbonyl-$C_1$-$C_6$-haloalkylthio, N—($C_1$-$C_6$-haloalkyl)-aminocarbonyl-$C_1$-$C_6$-haloalkylthio, N,N-di($C_1$-$C_6$-alkyl)-aminocarbonyl-$C_1$-$C_6$-alkylthio, N,N-di($C_1$-$C_6$-haloalkyl)-aminocarbonyl-$C_1$-$C_6$-alkylthio, N,N-di($C_1$-$C_6$-alkyl)-aminocarbonyl-$C_1$-$C_6$-haloalkylthio, N,N-di($C_1$-$C_6$-haloalkyl)-aminocarbonyl-$C_1$-$C_6$-haloalkylthio, $NH_2$, ($C_1$-$C_6$-alkyl)amino, hydroxyamino, ($C_1$-$C_6$-alkoxy)amino, ($C_3$-$C_6$-cycloalkoxy)amino, ($C_1$-$C_6$-alkyl)sulfinylamino, ($C_1$-$C_6$-alkyl)sulfonylamino, (amino)sulfinylamino, [($C_1$-$C_6$-alkyl)amino]sulfinylamino, (amino)sulfonylamino, [($C_1$-$C_6$-alkyl)amino]sulfonylamino, [di($C_1$-$C_6$-alkyl)amino]sulfonylamino, di($C_1$-$C_6$-alkyl)amino, (hydroxy)($C_1$-$C_6$-alkyl)amino, (hydroxy)($C_1$-$C_6$-cycloalkyl)amino, ($C_1$-$C_6$-alkoxy)($C_1$-$C_6$-alkyl)amino, ($C_1$-$C_6$-alkoxy) ($C_3$-$C_6$-cycloalkyl)amino, ($C_3$-$C_6$-cycloalkoxy)($C_1$-$C_6$-alkyl)amino, ($C_3$-$C_6$-cycloalkoxy)($C_3$-$C_6$-cycloalkyl)amino, [($C_1$-$C_6$-alkyl)sulfinyl]($C_1$-$C_6$-alkyl)amino, [($C_1$-$C_6$-alkyl)sulfonyl]($C_1$-$C_6$-alkyl) amino, [di($C_1$-$C_6$-alkyl)amino]sulfinylamino, [di($C_1$-$C_6$-alkyl)amino]sulfonylamino, phenyloxy, phenyl-$C_1$-$C_6$-alkoxy, phenylthio, phenyl-$C_1$-$C_6$-alkylthio, phenylamino, ($C_1$-$C_6$-alkyl)(phenyl) amino, (heteroaryl)oxy, heteroaryl-$C_1$-$C_6$-alkoxy, (heterocyclyl)oxy, heterocyclyl-$C_1$-$C_6$-alkoxy,
  wherein the phenyl, heteroaryl and heterocyclyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^3$ halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_1$-$C_6$-alkoxy, $C_1$-$C_6$-haloalkoxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl) oxy or phenyl;
  wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

and $R^4$, $R^5$, $R^6$ and $R^7$ independently of one another
  halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_1$-$C_6$-alkoxy, $C_1$-$C_6$-haloalkoxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl) amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;
  wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy.

Also preferred is the use as herbicides of the phenylpyrimidines of formula (I), wherein $R^1$ is $C_1$-$C_6$-alkyl, $C_1$-$C_6$-alkoxy, $C_1$-$C_6$-haloalkoxy, $C_2$-$C_6$-alkenyloxy, $C_2$-$C_6$-haloalkenyloxy $C_2$-$C_6$-alkinyloxy, $C_2$-$C_6$-haloalkinyloxy, $C_1$-$C_6$-alkylthio, $C_3$-$C_6$-cycloalkyl or phenyl,
  wherein the cycloalkyl or phenyl substituent is unsubstituted;
  particularly preferred $C_1$-$C_6$-alkyl, $C_1$-$C_6$-alkoxy or $C_3$-$C_6$-cycloalkyl,
  wherein the cycloalkyl substituent is unsubstituted;
  especially preferred $C_3$-$C_6$-cycloalkyl,
  wherein the cycloalkyl substituent is unsubstituted;
  also especially preferred $C_2H_5$, i-$C_3H_7$, i-$C_4H_9$, $OCH_3$, c-$C_3H_5$ or c-$C_4H_9$;
  more preferred $C_2H_5$, $OCH_3$ or c-$C_3H_5$;
  most preferred c-$C_3H_5$.

Also preferred is the use as herbicides of the phenylpyrimidines of formula (I), wherein $R^1$ is $C_1$-$C_6$-alkyl, $C_1$-$C_6$-alkoxy, $C_1$-$C_6$-haloalkoxy, $C_1$-$C_6$-alkylthio, $C_3$-$C_6$-cycloalkyl or phenyl,
  wherein the cycloalkyl or phenyl substituent is unsubstituted;
  particularly preferred $C_1$-$C_6$-alkyl, $C_1$-$C_6$-alkoxy or $C_3$-$C_6$-cycloalkyl,
  wherein the cycloalkyl substituent is unsubstituted;
  especially preferred $C_3$-$C_6$-cycloalkyl,
  wherein the cycloalkyl substituent is unsubstituted;
  also especially preferred $C_2H_5$, i-$C_3H_7$, i-$C_4H_9$, $OCH_3$, c-$C_3H_5$ or c-$C_4H_9$;
  more preferred $C_2H_5$, $OCH_3$ or c-$C_3H_5$;
  most preferred c-$C_3H_5$.

Also preferred is the use as herbicides of the phenylpyrimidines of formula (I), wherein $R^2$ is OH, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, ($C_1$-$C_6$-alkoxy)carbonyl-$C_1$-$C_6$-alkoxy, $C_1$-$C_6$-alkylthio, ($C_1$-$C_6$-alkoxy)carbonyl-$C_1$-$C_6$-alkylthio, $NH_2$, ($C_1$-$C_6$-alkyl)amino, ($C_1$-$C_6$-alkyl)sulfonylamino, [di($C_1$-$C_6$-alkyl)amino]sulfonylamino, phenyloxy, phenyl-$C_1$-$C_6$-alkoxy or phenyl-$C_1$-$C_6$-alkylthio,
  wherein the phenyl substituent is unsubstituted;
  preferably OH, $C_1$-$C_6$-alkoxy, $C_1$-$C_6$-haloalkoxy, $C_2$-$C_6$-alkynyloxy, ($C_1$-$C_6$-alkoxy)carbonyl-$C_1$-$C_6$-alkoxy, $C_1$-$C_6$-alkylthio, ($C_1$-$C_6$-alkoxy)carbonyl-$C_1$-$C_6$-alkylthio, $NH_2$, ($C_1$-$C_6$-alkyl)amino, ($C_1$-$C_6$-alkyl)sulfonylamino, [di($C_1$-$C_6$-alkyl)amino]sulfonylamino, phenyloxy, phenyl-$C_1$-$C_6$-alkoxy or phenyl-$C_1$-$C_6$-alkylthio,
  wherein the phenyl substituent is unsubstituted;
  particularly preferred OH, $C_1$-$C_6$-alkoxy, $C_1$-$C_6$-haloalkoxy, $C_2$-$C_6$-alkynyloxy, $C_1$-$C_6$-alkylthio, phenyloxy or phenyl-$C_1$-$C_6$-alkoxy,
  wherein the phenyl substituent is unsubstituted;
  also particularly preferred OH, $C_1$-$C_6$-alkoxy, $C_2$-$C_6$-alkynyloxy or $C_1$-$C_6$-haloalkoxy;
  especially preferred $C_1$-$C_6$-alkoxy, $C_2$-$C_6$-alkynyloxy or $C_1$-$C_6$-haloalkoxy;
  also especially preferred OH, $C_1$-$C_6$-alkoxy or $C_1$-$C_6$-haloalkoxy;
  more preferred OH or $C_1$-$C_6$-alkoxy,
  most preferred OH,
  also most preferred $C_1$-$C_6$-alkoxy.

Also preferred is the use as herbicides of the phenylpyrimidines of formula (I), wherein $R^3$ is halogen, CN, $NO_2$, $C_1$-$C_6$-alkyl, $C_1$-$C_6$-haloalkyl, $C_1$-$C_6$-alkoxy or $C_3$-$C_6$-cycloalkyl; also preferred halogen, CN, $C_1$-$C_6$-alkyl, $C_1$-$C_6$-haloalkyl or $C_1$-$C_6$-alkoxy, particularly preferred halogen, CN, $C_1$-$C_6$-alkyl or $C_1$-$C_6$-alkoxy;
  especially preferred halogen or $CH_3$;
  also especially preferred halogen;
  more preferred Cl, Br or I;
  most preferred Br or I.

Also preferred is the use as herbicides of the phenylpyrimidines of formula (I), wherein $R^4$, $R^5$, $R^6$ and $R^7$ independently of one another are
  H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_1$-$C_6$-alkoxy, $C_1$-$C_6$-haloalkoxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, NO$_2$, C$_1$-C$_6$-alkyl, C$_1$-C$_6$-haloalkyl, C$_1$-C$_6$-alkoxy or C$_1$-C$_6$-haloalkoxy.

Also preferred is the use as herbicides of the phenylpyrimidines of formula (I), wherein R$^4$ is H, halogen, CN, C$_1$-C$_6$-alkyl, C$_1$-C$_6$-haloalkyl or C$_1$-C$_6$-alkoxy;
particularly preferred H, halogen or C$_1$-C$_6$-alkyl,
especially preferred H or halogen;
more preferred H or F;
most preferred H;
also most preferred F.

Also preferred is the use as herbicides of the phenylpyrimidines of formula (I), wherein R$^5$ is H, halogen, CN, C$_1$-C$_6$-alkyl, C$_1$-C$_6$-haloalkyl or C$_1$-C$_6$-alkoxy;
particularly preferred H, halogen, C$_1$-C$_6$-alkyl C$_1$-C$_6$-haloalkyl or C$_1$-C$_6$-alkoxy;
especially preferred H, halogen, C$_1$-C$_6$-alkyl or C$_1$-C$_6$-alkoxy;
more preferred H, F, Cl, CH$_3$ or OCH$_3$;
also more preferred H or halogen;
most preferred H or F;
also most preferred H;
also most preferred F.

Also preferred is the use as herbicides of the phenylpyrimidines of formula (I), wherein R$^6$ is H, halogen, C$_1$-C$_6$-alkyl or C$_1$-C$_6$-alkoxy;
particularly preferred H, halogen or C$_1$-C$_6$-alkyl;
especially preferred H, halogen or CH$_3$;
more preferred H or halogen;
most preferred H or F;
also most preferred H;
also most preferred F.

Also preferred is the use as herbicides of the phenylpyrimidines of formula (I), wherein R$^7$ is H, halogen, CN, C$_1$-C$_6$-alkyl or C$_1$-C$_6$-alkoxy;
particularly preferred H, halogen, C$_1$-C$_6$-alkyl or C$_1$-C$_6$-alkoxy;
especially preferred H, halogen or C$_1$-C$_6$-alkyl;
more preferred H, F, Cl or CH$_3$;
most preferred H, F or Cl;
also most preferred CH$_3$;
also most preferred H.

Also preferred is the use as herbicides of the phenylpyrimidines of formula (I), wherein R$^1$ is preferably C$_1$-C$_6$-alkyl, C$_1$-C$_6$-alkoxy or C$_3$-C$_6$-cycloalkyl,
wherein the cycloalkyl substituent is unsubstituted;
particularly preferred C$_3$-C$_6$-cycloalkyl,
wherein the cycloalkyl substituent is unsubstituted;

R$^2$ is preferably OH, C$_1$-C$_6$-alkoxy, C$_2$-C$_6$-alkynyloxy or C$_1$-C$_6$-haloalkoxy;
particularly preferred C$_1$-C$_6$-alkoxy, C$_2$-C$_6$-alkynyloxy or C$_1$-C$_6$-haloalkoxy also particularly preferred OH or C$_1$-C$_6$-alkoxy,
more preferred OH;
also more preferred C$_1$-C$_6$-alkoxy;

R$^3$ is preferably halogen, CN, C$_1$-C$_6$-alkyl, C$_1$-C$_6$-haloalkyl or C$_1$-C$_6$-alkoxy; particularly preferred halogen or CH$_3$;

R$^4$ is preferably H;

R$^5$ is preferably H or halogen;

R$^6$ is preferably H or halogen;

R$^7$ is H, halogen, C$_1$-C$_6$-alkyl, C$_1$-C$_6$-alkoxy.

Particular preference is given to the use of phenylpyrimidines of formula (I.a) (corresponds to phenylpyrimidines of formula (I) wherein R$^2$ is OH and R$^4$ is H),

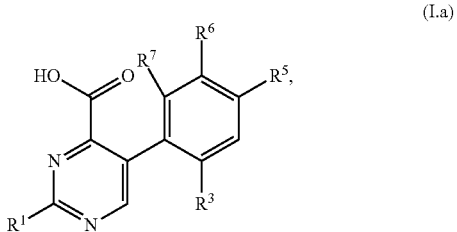

(I.a)

wherein the variables R$^1$, R$^3$, R$^5$, R$^6$ and R$^7$ have the meanings, in particular the preferred meanings, as defined above.

Special preference is given to the use of the phenylpyrimidines of the formulae (I.a.1) to (I.a.672) of Table (I), where the definitions of the variables R$^1$, R$^2$, R$^3$, R$^5$, R$^6$ and R$^7$ are of particular importance for the compounds according to the invention not only in combination with one another but in each case also on their own:

TABLE (I)

| No. | R$^1$ | R$^3$ | R$^5$ | R$^6$ | R$^7$ |
|---|---|---|---|---|---|
| I.a.1. | c-C$_3$H$_5$ | F | H | H | H |
| I.a.2. | c-C$_3$H$_5$ | F | H | H | F |
| I.a.3. | c-C$_3$H$_5$ | F | H | H | Cl |
| I.a.4. | c-C$_3$H$_5$ | F | H | H | Br |
| I.a.5. | c-C$_3$H$_5$ | F | H | H | CH$_3$ |
| I.a.6. | c-C$_3$H$_5$ | F | H | H | OCH$_3$ |
| I.a.7. | c-C$_3$H$_5$ | F | H | F | H |
| I.a.8. | c-C$_3$H$_5$ | F | H | F | F |
| I.a.9. | c-C$_3$H$_5$ | F | H | F | Cl |
| I.a.10. | c-C$_3$H$_5$ | F | H | F | Br |
| I.a.11. | c-C$_3$H$_5$ | F | H | F | CH$_3$ |
| I.a.12. | c-C$_3$H$_5$ | F | H | F | OCH$_3$ |
| I.a.13. | c-C$_3$H$_5$ | F | F | H | H |
| I.a.14. | c-C$_3$H$_5$ | F | F | H | F |
| I.a.15. | c-C$_3$H$_5$ | F | F | H | Cl |
| I.a.16. | c-C$_3$H$_5$ | F | F | H | Br |
| I.a.17. | c-C$_3$H$_5$ | F | F | H | CH$_3$ |
| I.a.18. | c-C$_3$H$_5$ | F | F | H | OCH$_3$ |
| I.a.19. | c-C$_3$H$_5$ | F | F | F | H |
| I.a.20. | c-C$_3$H$_5$ | F | F | F | F |
| I.a.21. | c-C$_3$H$_5$ | F | F | F | Cl |
| I.a.22. | c-C$_3$H$_5$ | F | F | F | Br |
| I.a.23. | c-C$_3$H$_5$ | F | F | F | CH$_3$ |
| I.a.24. | c-C$_3$H$_5$ | F | F | F | OCH$_3$ |
| I.a.25. | c-C$_3$H$_5$ | Cl | H | H | H |
| I.a.26. | c-C$_3$H$_5$ | Cl | H | H | F |
| I.a.27. | c-C$_3$H$_5$ | Cl | H | H | Cl |
| I.a.28. | c-C$_3$H$_5$ | Cl | H | H | Br |
| I.a.29. | c-C$_3$H$_5$ | Cl | H | H | CH$_3$ |
| I.a.30. | c-C$_3$H$_5$ | Cl | H | H | OCH$_3$ |
| I.a.31. | c-C$_3$H$_5$ | Cl | H | F | H |
| I.a.32. | c-C$_3$H$_5$ | Cl | H | F | F |
| I.a.33. | c-C$_3$H$_5$ | Cl | H | F | Cl |
| I.a.34. | c-C$_3$H$_5$ | Cl | H | F | Br |
| I.a.35. | c-C$_3$H$_5$ | Cl | H | F | CH$_3$ |
| I.a.36. | c-C$_3$H$_5$ | Cl | H | F | OCH$_3$ |
| I.a.37. | c-C$_3$H$_5$ | Cl | F | H | H |
| I.a.38. | c-C$_3$H$_5$ | Cl | F | H | F |
| I.a.39. | c-C$_3$H$_5$ | Cl | F | H | Cl |
| I.a.40. | c-C$_3$H$_5$ | Cl | F | H | Br |
| I.a.41. | c-C$_3$H$_5$ | Cl | F | H | CH$_3$ |
| I.a.42. | c-C$_3$H$_5$ | Cl | F | H | OCH$_3$ |
| I.a.43. | c-C$_3$H$_5$ | Cl | F | F | H |
| I.a.44. | c-C$_3$H$_5$ | Cl | F | F | F |
| I.a.45. | c-C$_3$H$_5$ | Cl | F | F | Cl |
| I.a.46. | c-C$_3$H$_5$ | Cl | F | F | Br |

TABLE (I)-continued

| No. | R¹ | R³ | R⁵ | R⁶ | R⁷ |
|---|---|---|---|---|---|
| I.a.47. | c-C₃H₅ | Cl | F | F | CH₃ |
| I.a.48. | c-C₃H₅ | Cl | F | F | OCH₃ |
| I.a.49. | c-C₃H₅ | Br | H | H | H |
| I.a.50. | c-C₃H₅ | Br | H | H | F |
| I.a.51. | c-C₃H₅ | Br | H | H | Cl |
| I.a.52. | c-C₃H₅ | Br | H | H | Br |
| I.a.53. | c-C₃H₅ | Br | H | H | CH₃ |
| I.a.54. | c-C₃H₅ | Br | H | H | OCH₃ |
| I.a.55. | c-C₃H₅ | Br | H | F | H |
| I.a.56. | c-C₃H₅ | Br | H | F | F |
| I.a.57. | c-C₃H₅ | Br | H | F | Cl |
| I.a.58. | c-C₃H₅ | Br | H | F | Br |
| I.a.59. | c-C₃H₅ | Br | H | F | CH₃ |
| I.a.60. | c-C₃H₅ | Br | H | F | OCH₃ |
| I.a.61. | c-C₃H₅ | Br | F | H | H |
| I.a.62. | c-C₃H₅ | Br | F | H | F |
| I.a.63. | c-C₃H₅ | Br | F | H | Cl |
| I.a.64. | c-C₃H₅ | Br | F | H | Br |
| I.a.65. | c-C₃H₅ | Br | F | H | CH₃ |
| I.a.66. | c-C₃H₅ | Br | F | H | OCH₃ |
| I.a.67. | c-C₃H₅ | Br | F | F | H |
| I.a.68. | c-C₃H₅ | Br | F | F | F |
| I.a.69. | c-C₃H₅ | Br | F | F | Cl |
| I.a.70. | c-C₃H₅ | Br | F | F | Br |
| I.a.71. | c-C₃H₅ | Br | F | F | CH₃ |
| I.a.72. | c-C₃H₅ | Br | F | F | OCH₃ |
| I.a.73. | c-C₃H₅ | I | H | H | H |
| I.a.74. | c-C₃H₅ | I | H | H | F |
| I.a.75. | c-C₃H₅ | I | H | H | Cl |
| I.a.76. | c-C₃H₅ | I | H | H | Br |
| I.a.77. | c-C₃H₅ | I | H | H | CH₃ |
| I.a.78. | c-C₃H₅ | I | H | H | OCH₃ |
| I.a.79. | c-C₃H₅ | I | H | F | H |
| I.a.80. | c-C₃H₅ | I | H | F | F |
| I.a.81. | c-C₃H₅ | I | H | F | Cl |
| I.a.82. | c-C₃H₅ | I | H | F | Br |
| I.a.83. | c-C₃H₅ | I | H | F | CH₃ |
| I.a.84. | c-C₃H₅ | I | H | F | OCH₃ |
| I.a.85. | c-C₃H₅ | I | F | H | H |
| I.a.86. | c-C₃H₅ | I | F | H | F |
| I.a.87. | c-C₃H₅ | I | F | H | Cl |
| I.a.88. | c-C₃H₅ | I | F | H | Br |
| I.a.89. | c-C₃H₅ | I | F | H | CH₃ |
| I.a.90. | c-C₃H₅ | I | F | H | OCH₃ |
| I.a.91. | c-C₃H₅ | I | F | F | H |
| I.a.92. | c-C₃H₅ | I | F | F | F |
| I.a.93. | c-C₃H₅ | I | F | F | Cl |
| I.a.94. | c-C₃H₅ | I | F | F | Br |
| I.a.95. | c-C₃H₅ | I | F | F | CH₃ |
| I.a.96. | c-C₃H₅ | I | F | F | OCH₃ |
| I.a.97. | c-C₃H₅ | CH₃ | H | H | H |
| I.a.98. | c-C₃H₅ | CH₃ | H | H | F |
| I.a.99. | c-C₃H₅ | CH₃ | H | H | Cl |
| I.a.100. | c-C₃H₅ | CH₃ | H | H | Br |
| I.a.101. | c-C₃H₅ | CH₃ | H | H | CH₃ |
| I.a.102. | c-C₃H₅ | CH₃ | H | H | OCH₃ |
| I.a.103. | c-C₃H₅ | CH₃ | H | F | H |
| I.a.104. | c-C₃H₅ | CH₃ | H | F | F |
| I.a.105. | c-C₃H₅ | CH₃ | H | F | Cl |
| I.a.106. | c-C₃H₅ | CH₃ | H | F | Br |
| I.a.107. | c-C₃H₅ | CH₃ | H | F | CH₃ |
| I.a.108. | c-C₃H₅ | CH₃ | H | F | OCH₃ |
| I.a.109. | c-C₃H₅ | CH₃ | F | H | H |
| I.a.110. | c-C₃H₅ | CH₃ | F | H | F |
| I.a.111. | c-C₃H₅ | CH₃ | F | H | Cl |
| I.a.112. | c-C₃H₅ | CH₃ | F | H | Br |
| I.a.113. | c-C₃H₅ | CH₃ | F | H | CH₃ |
| I.a.114. | c-C₃H₅ | CH₃ | F | H | OCH₃ |
| I.a.115. | c-C₃H₅ | CH₃ | F | F | H |
| I.a.116. | c-C₃H₅ | CH₃ | F | F | F |
| I.a.117. | c-C₃H₅ | CH₃ | F | F | Cl |
| I.a.118. | c-C₃H₅ | CH₃ | F | F | Br |
| I.a.119. | c-C₃H₅ | CH₃ | F | F | CH₃ |
| I.a.120. | c-C₃H₅ | CH₃ | F | F | OCH₃ |
| I.a.121. | c-C₃H₅ | OCH₃ | H | H | H |
| I.a.122. | c-C₃H₅ | OCH₃ | H | H | F |
| I.a.123. | c-C₃H₅ | OCH₃ | H | H | Cl |
| I.a.124. | c-C₃H₅ | OCH₃ | H | H | Br |
| I.a.125. | c-C₃H₅ | OCH₃ | H | H | CH₃ |
| I.a.126. | c-C₃H₅ | OCH₃ | H | H | OCH₃ |
| I.a.127. | c-C₃H₅ | OCH₃ | H | F | H |
| I.a.128. | c-C₃H₅ | OCH₃ | H | F | F |
| I.a.129. | c-C₃H₅ | OCH₃ | H | F | Cl |
| I.a.130. | c-C₃H₅ | OCH₃ | H | F | Br |
| I.a.131. | c-C₃H₅ | OCH₃ | H | F | CH₃ |
| I.a.132. | c-C₃H₅ | OCH₃ | H | F | OCH₃ |
| I.a.133. | c-C₃H₅ | OCH₃ | F | H | H |
| I.a.134. | c-C₃H₅ | OCH₃ | F | H | F |
| I.a.135. | c-C₃H₅ | OCH₃ | F | H | Cl |
| I.a.136. | c-C₃H₅ | OCH₃ | F | H | Br |
| I.a.137. | c-C₃H₅ | OCH₃ | F | H | CH₃ |
| I.a.138. | c-C₃H₅ | OCH₃ | F | H | OCH₃ |
| I.a.139. | c-C₃H₅ | OCH₃ | F | F | H |
| I.a.140. | c-C₃H₅ | OCH₃ | F | F | F |
| I.a.141. | c-C₃H₅ | OCH₃ | F | F | Cl |
| I.a.142. | c-C₃H₅ | OCH₃ | F | F | Br |
| I.a.143. | c-C₃H₅ | OCH₃ | F | F | CH₃ |
| I.a.144. | c-C₃H₅ | OCH₃ | F | F | OCH₃ |
| I.a.145. | c-C₃H₅ | CF₃ | H | H | H |
| I.a.146. | c-C₃H₅ | CF₃ | H | H | F |
| I.a.147. | c-C₃H₅ | CF₃ | H | H | Cl |
| I.a.148. | c-C₃H₅ | CF₃ | H | H | Br |
| I.a.149. | c-C₃H₅ | CF₃ | H | H | CH₃ |
| I.a.150. | c-C₃H₅ | CF₃ | H | H | OCH₃ |
| I.a.151. | c-C₃H₅ | CF₃ | H | F | H |
| I.a.152. | c-C₃H₅ | CF₃ | H | F | F |
| I.a.153. | c-C₃H₅ | CF₃ | H | F | Cl |
| I.a.154. | c-C₃H₅ | CF₃ | H | F | Br |
| I.a.155. | c-C₃H₅ | CF₃ | H | F | CH₃ |
| I.a.156. | c-C₃H₅ | CF₃ | H | F | OCH₃ |
| I.a.157. | c-C₃H₅ | CF₃ | F | H | H |
| I.a.158. | c-C₃H₅ | CF₃ | F | H | F |
| I.a.159. | c-C₃H₅ | CF₃ | F | H | Cl |
| I.a.160. | c-C₃H₅ | CF₃ | F | H | Br |
| I.a.161. | c-C₃H₅ | CF₃ | F | H | CH₃ |
| I.a.162. | c-C₃H₅ | CF₃ | F | H | OCH₃ |
| I.a.163. | c-C₃H₅ | CF₃ | F | F | H |
| I.a.164. | c-C₃H₅ | CF₃ | F | F | F |
| I.a.165. | c-C₃H₅ | CF₃ | F | F | Cl |
| I.a.166. | c-C₃H₅ | CF₃ | F | F | Br |
| I.a.167. | c-C₃H₅ | CF₃ | F | F | CH₃ |
| I.a.168. | c-C₃H₅ | CF₃ | F | F | OCH₃ |
| I.a.169. | c-C₄H₇ | F | H | H | H |
| I.a.170. | c-C₄H₇ | F | H | H | F |
| I.a.171. | c-C₄H₇ | F | H | H | Cl |
| I.a.172. | c-C₄H₇ | F | H | H | Br |
| I.a.173. | c-C₄H₇ | F | H | H | CH₃ |
| I.a.174. | c-C₄H₇ | F | H | H | OCH₃ |
| I.a.175. | c-C₄H₇ | F | H | F | H |
| I.a.176. | c-C₄H₇ | F | H | F | F |
| I.a.177. | c-C₄H₇ | F | H | F | Cl |
| I.a.178. | c-C₄H₇ | F | H | F | Br |
| I.a.179. | c-C₄H₇ | F | H | F | CH₃ |
| I.a.180. | c-C₄H₇ | F | H | F | OCH₃ |
| I.a.181. | c-C₄H₇ | F | F | H | H |
| I.a.182. | c-C₄H₇ | F | F | H | F |
| I.a.183. | c-C₄H₇ | F | F | H | Cl |
| I.a.184. | c-C₄H₇ | F | F | H | Br |
| I.a.185. | c-C₄H₇ | F | F | H | CH₃ |
| I.a.186. | c-C₄H₇ | F | F | H | OCH₃ |
| I.a.187. | c-C₄H₇ | F | F | F | H |
| I.a.188. | c-C₄H₇ | F | F | F | F |
| I.a.189. | c-C₄H₇ | F | F | F | Cl |
| I.a.190. | c-C₄H₇ | F | F | F | Br |
| I.a.191. | c-C₄H₇ | F | F | F | CH₃ |
| I.a.192. | c-C₄H₇ | F | F | F | OCH₃ |
| I.a.193. | c-C₄H₇ | Cl | H | H | H |
| I.a.194. | c-C₄H₇ | Cl | H | H | F |
| I.a.195. | c-C₄H₇ | Cl | H | H | Cl |
| I.a.196. | c-C₄H₇ | Cl | H | H | Br |
| I.a.197. | c-C₄H₇ | Cl | H | H | CH₃ |
| I.a.198. | c-C₄H₇ | Cl | H | H | OCH₃ |
| I.a.199. | c-C₄H₇ | Cl | H | F | H |
| I.a.200. | c-C₄H₇ | Cl | H | F | F |
| I.a.201. | c-C₄H₇ | Cl | H | F | Cl |
| I.a.202. | c-C₄H₇ | Cl | H | F | Br |

TABLE (I)-continued

| No. | R¹ | R³ | R⁵ | R⁶ | R⁷ |
|---|---|---|---|---|---|
| I.a.203. | c-C₄H₇ | Cl | H | F | CH₃ |
| I.a.204. | c-C₄H₇ | Cl | H | F | OCH₃ |
| I.a.205. | c-C₄H₇ | Cl | F | H | H |
| I.a.206. | c-C₄H₇ | Cl | F | H | F |
| I.a.207. | c-C₄H₇ | Cl | F | H | Cl |
| I.a.208. | c-C₄H₇ | Cl | F | H | Br |
| I.a.209. | c-C₄H₇ | Cl | F | H | CH₃ |
| I.a.210. | c-C₄H₇ | Cl | F | H | OCH₃ |
| I.a.211. | c-C₄H₇ | Cl | F | F | H |
| I.a.212. | c-C₄H₇ | Cl | F | F | F |
| I.a.213. | c-C₄H₇ | Cl | F | F | Cl |
| I.a.214. | c-C₄H₇ | Cl | F | F | Br |
| I.a.215. | c-C₄H₇ | Cl | F | F | CH₃ |
| I.a.216. | c-C₄H₇ | Cl | F | F | OCH₃ |
| I.a.217. | c-C₄H₇ | Br | H | H | H |
| I.a.218. | c-C₄H₇ | Br | H | H | F |
| I.a.219. | c-C₄H₇ | Br | H | H | Cl |
| I.a.220. | c-C₄H₇ | Br | H | H | Br |
| I.a.221. | c-C₄H₇ | Br | H | H | CH₃ |
| I.a.222. | c-C₄H₇ | Br | H | H | OCH₃ |
| I.a.223. | c-C₄H₇ | Br | H | F | H |
| I.a.224. | c-C₄H₇ | Br | H | F | F |
| I.a.225. | c-C₄H₇ | Br | H | F | Cl |
| I.a.226. | c-C₄H₇ | Br | H | F | Br |
| I.a.227. | c-C₄H₇ | Br | H | F | CH₃ |
| I.a.228. | c-C₄H₇ | Br | H | F | OCH₃ |
| I.a.229. | c-C₄H₇ | Br | F | H | H |
| I.a.230. | c-C₄H₇ | Br | F | H | F |
| I.a.231. | c-C₄H₇ | Br | F | H | Cl |
| I.a.232. | c-C₄H₇ | Br | F | H | Br |
| I.a.233. | c-C₄H₇ | Br | F | H | CH₃ |
| I.a.234. | c-C₄H₇ | Br | F | H | OCH₃ |
| I.a.235. | c-C₄H₇ | Br | F | F | H |
| I.a.236. | c-C₄H₇ | Br | F | F | F |
| I.a.237. | c-C₄H₇ | Br | F | F | Cl |
| I.a.238. | c-C₄H₇ | Br | F | F | Br |
| I.a.239. | c-C₄H₇ | Br | F | F | CH₃ |
| I.a.240. | c-C₄H₇ | Br | F | F | OCH₃ |
| I.a.241. | c-C₄H₇ | I | H | H | H |
| I.a.242. | c-C₄H₇ | I | H | H | F |
| I.a.243. | c-C₄H₇ | I | H | H | Cl |
| I.a.244. | c-C₄H₇ | I | H | H | Br |
| I.a.245. | c-C₄H₇ | I | H | H | CH₃ |
| I.a.246. | c-C₄H₇ | I | H | H | OCH₃ |
| I.a.247. | c-C₄H₇ | I | H | F | H |
| I.a.248. | c-C₄H₇ | I | H | F | F |
| I.a.249. | c-C₄H₇ | I | H | F | Cl |
| I.a.250. | c-C₄H₇ | I | H | F | Br |
| I.a.251. | c-C₄H₇ | I | H | F | CH₃ |
| I.a.252. | c-C₄H₇ | I | H | F | OCH₃ |
| I.a.253. | c-C₄H₇ | I | F | H | H |
| I.a.254. | c-C₄H₇ | I | F | H | F |
| I.a.255. | c-C₄H₇ | I | F | H | Cl |
| I.a.256. | c-C₄H₇ | I | F | H | Br |
| I.a.257. | c-C₄H₇ | I | F | H | CH₃ |
| I.a.258. | c-C₄H₇ | I | F | H | OCH₃ |
| I.a.259. | c-C₄H₇ | I | F | F | H |
| I.a.260. | c-C₄H₇ | I | F | F | F |
| I.a.261. | c-C₄H₇ | I | F | F | Cl |
| I.a.262. | c-C₄H₇ | I | F | F | Br |
| I.a.263. | c-C₄H₇ | I | F | F | CH₃ |
| I.a.264. | c-C₄H₇ | I | F | F | OCH₃ |
| I.a.265. | c-C₄H₇ | CH₃ | H | H | H |
| I.a.266. | c-C₄H₇ | CH₃ | H | H | F |
| I.a.267. | c-C₄H₇ | CH₃ | H | H | Cl |
| I.a.268. | c-C₄H₇ | CH₃ | H | H | Br |
| I.a.269. | c-C₄H₇ | CH₃ | H | H | CH₃ |
| I.a.270. | c-C₄H₇ | CH₃ | H | H | OCH₃ |
| I.a.271. | c-C₄H₇ | CH₃ | H | F | H |
| I.a.272. | c-C₄H₇ | CH₃ | H | F | F |
| I.a.273. | c-C₄H₇ | CH₃ | H | F | Cl |
| I.a.274. | c-C₄H₇ | CH₃ | H | F | Br |
| I.a.275. | c-C₄H₇ | CH₃ | H | F | CH₃ |
| I.a.276. | c-C₄H₇ | CH₃ | H | F | OCH₃ |
| I.a.277. | c-C₄H₇ | CH₃ | F | H | H |
| I.a.278. | c-C₄H₇ | CH₃ | F | H | F |
| I.a.279. | c-C₄H₇ | CH₃ | F | H | Cl |
| I.a.280. | c-C₄H₇ | CH₃ | F | H | Br |
| I.a.281. | c-C₄H₇ | CH₃ | F | H | CH₃ |
| I.a.282. | c-C₄H₇ | CH₃ | F | H | OCH₃ |
| I.a.283. | c-C₄H₇ | CH₃ | F | F | H |
| I.a.284. | c-C₄H₇ | CH₃ | F | F | F |
| I.a.285. | c-C₄H₇ | CH₃ | F | F | Cl |
| I.a.286. | c-C₄H₇ | CH₃ | F | F | Br |
| I.a.287. | c-C₄H₇ | CH₃ | F | F | CH₃ |
| I.a.288. | c-C₄H₇ | CH₃ | F | F | OCH₃ |
| I.a.289. | c-C₄H₇ | OCH₃ | H | H | H |
| I.a.290. | c-C₄H₇ | OCH₃ | H | H | F |
| I.a.291. | c-C₄H₇ | OCH₃ | H | H | Cl |
| I.a.292. | c-C₄H₇ | OCH₃ | H | H | Br |
| I.a.293. | c-C₄H₇ | OCH₃ | H | H | CH₃ |
| I.a.294. | c-C₄H₇ | OCH₃ | H | H | OCH₃ |
| I.a.295. | c-C₄H₇ | OCH₃ | H | F | H |
| I.a.296. | c-C₄H₇ | OCH₃ | H | F | F |
| I.a.297. | c-C₄H₇ | OCH₃ | H | F | Cl |
| I.a.298. | c-C₄H₇ | OCH₃ | H | F | Br |
| I.a.299. | c-C₄H₇ | OCH₃ | H | F | CH₃ |
| I.a.300. | c-C₄H₇ | OCH₃ | H | F | OCH₃ |
| I.a.301. | c-C₄H₇ | OCH₃ | F | H | H |
| I.a.302. | c-C₄H₇ | OCH₃ | F | H | F |
| I.a.303. | c-C₄H₇ | OCH₃ | F | H | Cl |
| I.a.304. | c-C₄H₇ | OCH₃ | F | H | Br |
| I.a.305. | c-C₄H₇ | OCH₃ | F | H | CH₃ |
| I.a.306. | c-C₄H₇ | OCH₃ | F | H | OCH₃ |
| I.a.307. | c-C₄H₇ | OCH₃ | F | F | H |
| I.a.308. | c-C₄H₇ | OCH₃ | F | F | F |
| I.a.309. | c-C₄H₇ | OCH₃ | F | F | Cl |
| I.a.310. | c-C₄H₇ | OCH₃ | F | F | Br |
| I.a.311. | c-C₄H₇ | OCH₃ | F | F | CH₃ |
| I.a.312. | c-C₄H₇ | OCH₃ | F | F | OCH₃ |
| I.a.313. | c-C₄H₇ | CF₃ | H | H | H |
| I.a.314. | c-C₄H₇ | CF₃ | H | H | F |
| I.a.315. | c-C₄H₇ | CF₃ | H | H | Cl |
| I.a.316. | c-C₄H₇ | CF₃ | H | H | Br |
| I.a.317. | c-C₄H₇ | CF₃ | H | H | CH₃ |
| I.a.318. | c-C₄H₇ | CF₃ | H | H | OCH₃ |
| I.a.319. | c-C₄H₇ | CF₃ | H | F | H |
| I.a.320. | c-C₄H₇ | CF₃ | H | F | F |
| I.a.321. | c-C₄H₇ | CF₃ | H | F | Cl |
| I.a.322. | c-C₄H₇ | CF₃ | H | F | Br |
| I.a.323. | c-C₄H₇ | CF₃ | H | F | CH₃ |
| I.a.324. | c-C₄H₇ | CF₃ | H | F | OCH₃ |
| I.a.325. | c-C₄H₇ | CF₃ | F | H | H |
| I.a.326. | c-C₄H₇ | CF₃ | F | H | F |
| I.a.327. | c-C₄H₇ | CF₃ | F | H | Cl |
| I.a.328. | c-C₄H₇ | CF₃ | F | H | Br |
| I.a.329. | c-C₄H₇ | CF₃ | F | H | CH₃ |
| I.a.330. | c-C₄H₇ | CF₃ | F | H | OCH₃ |
| I.a.331. | c-C₄H₇ | CF₃ | F | F | H |
| I.a.332. | c-C₄H₇ | CF₃ | F | F | F |
| I.a.333. | c-C₄H₇ | CF₃ | F | F | Cl |
| I.a.334. | c-C₄H₇ | CF₃ | F | F | Br |
| I.a.335. | c-C₄H₇ | CF₃ | F | F | CH₃ |
| I.a.336. | c-C₄H₇ | CF₃ | F | F | OCH₃ |
| I.a.337. | C₂H₅ | F | H | H | H |
| I.a.338. | C₂H₅ | F | H | H | F |
| I.a.339. | C₂H₅ | F | H | H | Cl |
| I.a.340. | C₂H₅ | F | H | H | Br |
| I.a.341. | C₂H₅ | F | H | H | CH₃ |
| I.a.342. | C₂H₅ | F | H | H | OCH₃ |
| I.a.343. | C₂H₅ | F | H | F | H |
| I.a.344. | C₂H₅ | F | H | F | F |
| I.a.345. | C₂H₅ | F | H | F | Cl |
| I.a.346. | C₂H₅ | F | H | F | Br |
| I.a.347. | C₂H₅ | F | H | F | CH₃ |
| I.a.348. | C₂H₅ | F | H | F | OCH₃ |
| I.a.349. | C₂H₅ | F | F | H | H |
| I.a.350. | C₂H₅ | F | F | H | F |
| I.a.351. | C₂H₅ | F | F | H | Cl |
| I.a.352. | C₂H₅ | F | F | H | Br |
| I.a.353. | C₂H₅ | F | F | H | CH₃ |
| I.a.354. | C₂H₅ | F | F | H | OCH₃ |
| I.a.355. | C₂H₅ | F | F | F | H |
| I.a.356. | C₂H₅ | F | F | F | F |
| I.a.357. | C₂H₅ | F | F | F | Cl |
| I.a.358. | C₂H₅ | F | F | F | Br |

TABLE (I)-continued

| No. | $R^1$ | $R^3$ | $R^5$ | $R^6$ | $R^7$ |
|---|---|---|---|---|---|
| I.a.359. | $C_2H_5$ | F | F | F | $CH_3$ |
| I.a.360. | $C_2H_5$ | F | F | F | $OCH_3$ |
| I.a.361. | $C_2H_5$ | Cl | H | H | H |
| I.a.362. | $C_2H_5$ | Cl | H | H | F |
| I.a.363. | $C_2H_5$ | Cl | H | H | Cl |
| I.a.364. | $C_2H_5$ | Cl | H | H | Br |
| I.a.365. | $C_2H_5$ | Cl | H | H | $CH_3$ |
| I.a.366. | $C_2H_5$ | Cl | H | H | $OCH_3$ |
| I.a.367. | $C_2H_5$ | Cl | H | F | H |
| I.a.368. | $C_2H_5$ | Cl | H | F | F |
| I.a.369. | $C_2H_5$ | Cl | H | F | Cl |
| I.a.370. | $C_2H_5$ | Cl | H | F | Br |
| I.a.371. | $C_2H_5$ | Cl | H | F | $CH_3$ |
| I.a.372. | $C_2H_5$ | Cl | H | F | $OCH_3$ |
| I.a.373. | $C_2H_5$ | Cl | F | H | H |
| I.a.374. | $C_2H_5$ | Cl | F | H | F |
| I.a.375. | $C_2H_5$ | Cl | F | H | Cl |
| I.a.376. | $C_2H_5$ | Cl | F | H | Br |
| I.a.377. | $C_2H_5$ | Cl | F | H | $CH_3$ |
| I.a.378. | $C_2H_5$ | Cl | F | H | $OCH_3$ |
| I.a.379. | $C_2H_5$ | Cl | F | F | H |
| I.a.380. | $C_2H_5$ | Cl | F | F | F |
| I.a.381. | $C_2H_5$ | Cl | F | F | Cl |
| I.a.382. | $C_2H_5$ | Cl | F | F | Br |
| I.a.383. | $C_2H_5$ | Cl | F | F | $CH_3$ |
| I.a.384. | $C_2H_5$ | Cl | F | F | $OCH_3$ |
| I.a.385. | $C_2H_5$ | Br | H | H | H |
| I.a.386. | $C_2H_5$ | Br | H | H | F |
| I.a.387. | $C_2H_5$ | Br | H | H | Cl |
| I.a.388. | $C_2H_5$ | Br | H | H | Br |
| I.a.389. | $C_2H_5$ | Br | H | H | $CH_3$ |
| I.a.390. | $C_2H_5$ | Br | H | H | $OCH_3$ |
| I.a.391. | $C_2H_5$ | Br | H | F | H |
| I.a.392. | $C_2H_5$ | Br | H | F | F |
| I.a.393. | $C_2H_5$ | Br | H | F | Cl |
| I.a.394. | $C_2H_5$ | Br | H | F | Br |
| I.a.395. | $C_2H_5$ | Br | H | F | $CH_3$ |
| I.a.396. | $C_2H_5$ | Br | H | F | $OCH_3$ |
| I.a.397. | $C_2H_5$ | Br | F | H | H |
| I.a.398. | $C_2H_5$ | Br | F | H | F |
| I.a.399. | $C_2H_5$ | Br | F | H | Cl |
| I.a.400. | $C_2H_5$ | Br | F | H | Br |
| I.a.401. | $C_2H_5$ | Br | F | H | $CH_3$ |
| I.a.402. | $C_2H_5$ | Br | F | H | $OCH_3$ |
| I.a.403. | $C_2H_5$ | Br | F | F | H |
| I.a.404. | $C_2H_5$ | Br | F | F | F |
| I.a.405. | $C_2H_5$ | Br | F | F | Cl |
| I.a.406. | $C_2H_5$ | Br | F | F | Br |
| I.a.407. | $C_2H_5$ | Br | F | F | $CH_3$ |
| I.a.408. | $C_2H_5$ | Br | F | F | $OCH_3$ |
| I.a.409. | $C_2H_5$ | I | H | H | H |
| I.a.410. | $C_2H_5$ | I | H | H | F |
| I.a.411. | $C_2H_5$ | I | H | H | Cl |
| I.a.412. | $C_2H_5$ | I | H | H | Br |
| I.a.413. | $C_2H_5$ | I | H | H | $CH_3$ |
| I.a.414. | $C_2H_5$ | I | H | H | $OCH_3$ |
| I.a.415. | $C_2H_5$ | I | H | F | H |
| I.a.416. | $C_2H_5$ | I | H | F | F |
| I.a.417. | $C_2H_5$ | I | H | F | Cl |
| I.a.418. | $C_2H_5$ | I | H | F | Br |
| I.a.419. | $C_2H_5$ | I | H | F | $CH_3$ |
| I.a.420. | $C_2H_5$ | I | H | F | $OCH_3$ |
| I.a.421. | $C_2H_5$ | I | F | H | H |
| I.a.422. | $C_2H_5$ | I | F | H | F |
| I.a.423. | $C_2H_5$ | I | F | H | Cl |
| I.a.424. | $C_2H_5$ | I | F | H | Br |
| I.a.425. | $C_2H_5$ | I | F | H | $CH_3$ |
| I.a.426. | $C_2H_5$ | I | F | H | $OCH_3$ |
| I.a.427. | $C_2H_5$ | I | F | F | H |
| I.a.428. | $C_2H_5$ | I | F | F | F |
| I.a.429. | $C_2H_5$ | I | F | F | Cl |
| I.a.430. | $C_2H_5$ | I | F | F | Br |
| I.a.431. | $C_2H_5$ | I | F | F | $CH_3$ |
| I.a.432. | $C_2H_5$ | I | F | F | $OCH_3$ |
| I.a.433. | $C_2H_5$ | $CH_3$ | H | H | H |
| I.a.434. | $C_2H_5$ | $CH_3$ | H | H | F |
| I.a.435. | $C_2H_5$ | $CH_3$ | H | H | Cl |
| I.a.436. | $C_2H_5$ | $CH_3$ | H | H | Br |
| I.a.437. | $C_2H_5$ | $CH_3$ | H | H | $CH_3$ |
| I.a.438. | $C_2H_5$ | $CH_3$ | H | H | $OCH_3$ |
| I.a.439. | $C_2H_5$ | $CH_3$ | H | F | H |
| I.a.440. | $C_2H_5$ | $CH_3$ | H | F | F |
| I.a.441. | $C_2H_5$ | $CH_3$ | H | F | Cl |
| I.a.442. | $C_2H_5$ | $CH_3$ | H | F | Br |
| I.a.443. | $C_2H_5$ | $CH_3$ | H | F | $CH_3$ |
| I.a.444. | $C_2H_5$ | $CH_3$ | H | F | $OCH_3$ |
| I.a.445. | $C_2H_5$ | $CH_3$ | F | H | H |
| I.a.446. | $C_2H_5$ | $CH_3$ | F | H | F |
| I.a.447. | $C_2H_5$ | $CH_3$ | F | H | Cl |
| I.a.448. | $C_2H_5$ | $CH_3$ | F | H | Br |
| I.a.449. | $C_2H_5$ | $CH_3$ | F | H | $CH_3$ |
| I.a.450. | $C_2H_5$ | $CH_3$ | F | H | $OCH_3$ |
| I.a.451. | $C_2H_5$ | $CH_3$ | F | F | H |
| I.a.452. | $C_2H_5$ | $CH_3$ | F | F | F |
| I.a.453. | $C_2H_5$ | $CH_3$ | F | F | Cl |
| I.a.454. | $C_2H_5$ | $CH_3$ | F | F | Br |
| I.a.455. | $C_2H_5$ | $CH_3$ | F | F | $CH_3$ |
| I.a.456. | $C_2H_5$ | $CH_3$ | F | F | $OCH_3$ |
| I.a.457. | $C_2H_5$ | $OCH_3$ | H | H | H |
| I.a.458. | $C_2H_5$ | $OCH_3$ | H | H | F |
| I.a.459. | $C_2H_5$ | $OCH_3$ | H | H | Cl |
| I.a.460. | $C_2H_5$ | $OCH_3$ | H | H | Br |
| I.a.461. | $C_2H_5$ | $OCH_3$ | H | H | $CH_3$ |
| I.a.462. | $C_2H_5$ | $OCH_3$ | H | H | $OCH_3$ |
| I.a.463. | $C_2H_5$ | $OCH_3$ | H | F | H |
| I.a.464. | $C_2H_5$ | $OCH_3$ | H | F | F |
| I.a.465. | $C_2H_5$ | $OCH_3$ | H | F | Cl |
| I.a.466. | $C_2H_5$ | $OCH_3$ | H | F | Br |
| I.a.467. | $C_2H_5$ | $OCH_3$ | H | F | $CH_3$ |
| I.a.468. | $C_2H_5$ | $OCH_3$ | H | F | $OCH_3$ |
| I.a.469. | $C_2H_5$ | $OCH_3$ | F | H | H |
| I.a.470. | $C_2H_5$ | $OCH_3$ | F | H | F |
| I.a.471. | $C_2H_5$ | $OCH_3$ | F | H | Cl |
| I.a.472. | $C_2H_5$ | $OCH_3$ | F | H | Br |
| I.a.473. | $C_2H_5$ | $OCH_3$ | F | H | $CH_3$ |
| I.a.474. | $C_2H_5$ | $OCH_3$ | F | H | $OCH_3$ |
| I.a.475. | $C_2H_5$ | $OCH_3$ | F | F | H |
| I.a.476. | $C_2H_5$ | $OCH_3$ | F | F | F |
| I.a.477. | $C_2H_5$ | $OCH_3$ | F | F | Cl |
| I.a.478. | $C_2H_5$ | $OCH_3$ | F | F | Br |
| I.a.479. | $C_2H_5$ | $OCH_3$ | F | F | $CH_3$ |
| I.a.480. | $C_2H_5$ | $OCH_3$ | F | F | $OCH_3$ |
| I.a.481. | $C_2H_5$ | $CF_3$ | H | H | H |
| I.a.482. | $C_2H_5$ | $CF_3$ | H | H | F |
| I.a.483. | $C_2H_5$ | $CF_3$ | H | H | Cl |
| I.a.484. | $C_2H_5$ | $CF_3$ | H | H | Br |
| I.a.485. | $C_2H_5$ | $CF_3$ | H | H | $CH_3$ |
| I.a.486. | $C_2H_5$ | $CF_3$ | H | H | $OCH_3$ |
| I.a.487. | $C_2H_5$ | $CF_3$ | H | F | H |
| I.a.488. | $C_2H_5$ | $CF_3$ | H | F | F |
| I.a.489. | $C_2H_5$ | $CF_3$ | H | F | Cl |
| I.a.490. | $C_2H_5$ | $CF_3$ | H | F | Br |
| I.a.491. | $C_2H_5$ | $CF_3$ | H | F | $CH_3$ |
| I.a.492. | $C_2H_5$ | $CF_3$ | H | F | $OCH_3$ |
| I.a.493. | $C_2H_5$ | $CF_3$ | F | H | H |
| I.a.494. | $C_2H_5$ | $CF_3$ | F | H | F |
| I.a.495. | $C_2H_5$ | $CF_3$ | F | H | Cl |
| I.a.496. | $C_2H_5$ | $CF_3$ | F | H | Br |
| I.a.497. | $C_2H_5$ | $CF_3$ | F | H | $CH_3$ |
| I.a.498. | $C_2H_5$ | $CF_3$ | F | H | $OCH_3$ |
| I.a.499. | $C_2H_5$ | $CF_3$ | F | F | H |
| I.a.500. | $C_2H_5$ | $CF_3$ | F | F | F |
| I.a.501. | $C_2H_5$ | $CF_3$ | F | F | Cl |
| I.a.502. | $C_2H_5$ | $CF_3$ | F | F | Br |
| I.a.503. | $C_2H_5$ | $CF_3$ | F | F | $CH_3$ |
| I.a.504. | $C_2H_5$ | $CF_3$ | F | F | $OCH_3$ |
| I.a.505. | $OCH_3$ | F | H | H | H |
| I.a.506. | $OCH_3$ | F | H | H | F |
| I.a.507. | $OCH_3$ | F | H | H | Cl |
| I.a.508. | $OCH_3$ | F | H | H | Br |
| I.a.509. | $OCH_3$ | F | H | H | $CH_3$ |
| I.a.510. | $OCH_3$ | F | H | H | $OCH_3$ |
| I.a.511. | $OCH_3$ | F | H | F | H |
| I.a.512. | $OCH_3$ | F | H | F | F |
| I.a.513. | $OCH_3$ | F | H | F | Cl |
| I.a.514. | $OCH_3$ | F | H | F | Br |

TABLE (I)-continued

| No. | R$^1$ | R$^3$ | R$^5$ | R$^6$ | R$^7$ |
|---|---|---|---|---|---|
| I.a.515. | OCH$_3$ | F | H | F | CH$_3$ |
| I.a.516. | OCH$_3$ | F | H | F | OCH$_3$ |
| I.a.517. | OCH$_3$ | F | F | H | H |
| I.a.518. | OCH$_3$ | F | F | H | F |
| I.a.519. | OCH$_3$ | F | F | H | Cl |
| I.a.520. | OCH$_3$ | F | F | H | Br |
| I.a.521. | OCH$_3$ | F | F | H | CH$_3$ |
| I.a.522. | OCH$_3$ | F | F | H | OCH$_3$ |
| I.a.523. | OCH$_3$ | F | F | F | H |
| I.a.524. | OCH$_3$ | F | F | F | F |
| I.a.525. | OCH$_3$ | F | F | F | Cl |
| I.a.526. | OCH$_3$ | F | F | F | Br |
| I.a.527. | OCH$_3$ | F | F | F | CH$_3$ |
| I.a.528. | OCH$_3$ | F | F | F | OCH$_3$ |
| I.a.529. | OCH$_3$ | Cl | H | H | H |
| I.a.530. | OCH$_3$ | Cl | H | H | F |
| I.a.531. | OCH$_3$ | Cl | H | H | Cl |
| I.a.532. | OCH$_3$ | Cl | H | H | Br |
| I.a.533. | OCH$_3$ | Cl | H | H | CH$_3$ |
| I.a.534. | OCH$_3$ | Cl | H | H | OCH$_3$ |
| I.a.535. | OCH$_3$ | Cl | H | F | H |
| I.a.536. | OCH$_3$ | Cl | H | F | F |
| I.a.537. | OCH$_3$ | Cl | H | F | Cl |
| I.a.538. | OCH$_3$ | Cl | H | F | Br |
| I.a.539. | OCH$_3$ | Cl | H | F | CH$_3$ |
| I.a.540. | OCH$_3$ | Cl | H | F | OCH$_3$ |
| I.a.541. | OCH$_3$ | Cl | F | H | H |
| I.a.542. | OCH$_3$ | Cl | F | H | F |
| I.a.543. | OCH$_3$ | Cl | F | H | Cl |
| I.a.544. | OCH$_3$ | Cl | F | H | Br |
| I.a.545. | OCH$_3$ | Cl | F | H | CH$_3$ |
| I.a.546. | OCH$_3$ | Cl | F | H | OCH$_3$ |
| I.a.547. | OCH$_3$ | Cl | F | F | H |
| I.a.548. | OCH$_3$ | Cl | F | F | F |
| I.a.549. | OCH$_3$ | Cl | F | F | Cl |
| I.a.550. | OCH$_3$ | Cl | F | F | Br |
| I.a.551. | OCH$_3$ | Cl | F | F | CH$_3$ |
| I.a.552. | OCH$_3$ | Cl | F | F | OCH$_3$ |
| I.a.553. | OCH$_3$ | Br | H | H | H |
| I.a.554. | OCH$_3$ | Br | H | H | F |
| I.a.555. | OCH$_3$ | Br | H | H | Cl |
| I.a.556. | OCH$_3$ | Br | H | H | Br |
| I.a.557. | OCH$_3$ | Br | H | H | CH$_3$ |
| I.a.558. | OCH$_3$ | Br | H | H | OCH$_3$ |
| I.a.559. | OCH$_3$ | Br | H | F | H |
| I.a.560. | OCH$_3$ | Br | H | F | F |
| I.a.561. | OCH$_3$ | Br | H | F | Cl |
| I.a.562. | OCH$_3$ | Br | H | F | Br |
| I.a.563. | OCH$_3$ | Br | H | F | CH$_3$ |
| I.a.564. | OCH$_3$ | Br | H | F | OCH$_3$ |
| I.a.565. | OCH$_3$ | Br | F | H | H |
| I.a.566. | OCH$_3$ | Br | F | H | F |
| I.a.567. | OCH$_3$ | Br | F | H | Cl |
| I.a.568. | OCH$_3$ | Br | F | H | Br |
| I.a.569. | OCH$_3$ | Br | F | H | CH$_3$ |
| I.a.570. | OCH$_3$ | Br | F | H | OCH$_3$ |
| I.a.571. | OCH$_3$ | Br | F | F | H |
| I.a.572. | OCH$_3$ | Br | F | F | F |
| I.a.573. | OCH$_3$ | Br | F | F | Cl |
| I.a.574. | OCH$_3$ | Br | F | F | Br |
| I.a.575. | OCH$_3$ | Br | F | F | CH$_3$ |
| I.a.576. | OCH$_3$ | Br | F | F | OCH$_3$ |
| I.a.577. | OCH$_3$ | I | H | H | H |
| I.a.578. | OCH$_3$ | I | H | H | F |
| I.a.579. | OCH$_3$ | I | H | H | Cl |
| I.a.580. | OCH$_3$ | I | H | H | Br |
| I.a.581. | OCH$_3$ | I | H | H | CH$_3$ |
| I.a.582. | OCH$_3$ | I | H | H | OCH$_3$ |
| I.a.583. | OCH$_3$ | I | H | F | H |
| I.a.584. | OCH$_3$ | I | H | F | F |
| I.a.585. | OCH$_3$ | I | H | F | Cl |
| I.a.586. | OCH$_3$ | I | H | F | Br |
| I.a.587. | OCH$_3$ | I | H | F | CH$_3$ |
| I.a.588. | OCH$_3$ | I | H | F | OCH$_3$ |
| I.a.589. | OCH$_3$ | I | F | H | H |
| I.a.590. | OCH$_3$ | I | F | H | F |
| I.a.591. | OCH$_3$ | I | F | H | Cl |
| I.a.592. | OCH$_3$ | I | F | H | Br |
| I.a.593. | OCH$_3$ | I | F | H | CH$_3$ |
| I.a.594. | OCH$_3$ | I | F | H | OCH$_3$ |
| I.a.595. | OCH$_3$ | I | F | F | H |
| I.a.596. | OCH$_3$ | I | F | F | F |
| I.a.597. | OCH$_3$ | I | F | F | Cl |
| I.a.598. | OCH$_3$ | I | F | F | Br |
| I.a.599. | OCH$_3$ | I | F | F | CH$_3$ |
| I.a.600. | OCH$_3$ | I | F | F | OCH$_3$ |
| I.a.601. | OCH$_3$ | CH$_3$ | H | H | H |
| I.a.602. | OCH$_3$ | CH$_3$ | H | H | F |
| I.a.603. | OCH$_3$ | CH$_3$ | H | H | Cl |
| I.a.604. | OCH$_3$ | CH$_3$ | H | H | Br |
| I.a.605. | OCH$_3$ | CH$_3$ | H | H | CH$_3$ |
| I.a.606. | OCH$_3$ | CH$_3$ | H | H | OCH$_3$ |
| I.a.607. | OCH$_3$ | CH$_3$ | H | F | H |
| I.a.608. | OCH$_3$ | CH$_3$ | H | F | F |
| I.a.609. | OCH$_3$ | CH$_3$ | H | F | Cl |
| I.a.610. | OCH$_3$ | CH$_3$ | H | F | Br |
| I.a.611. | OCH$_3$ | CH$_3$ | H | F | CH$_3$ |
| I.a.612. | OCH$_3$ | CH$_3$ | H | F | OCH$_3$ |
| I.a.613. | OCH$_3$ | CH$_3$ | F | H | H |
| I.a.614. | OCH$_3$ | CH$_3$ | F | H | F |
| I.a.615. | OCH$_3$ | CH$_3$ | F | H | Cl |
| I.a.616. | OCH$_3$ | CH$_3$ | F | H | Br |
| I.a.617. | OCH$_3$ | CH$_3$ | F | H | CH$_3$ |
| I.a.618. | OCH$_3$ | CH$_3$ | F | H | OCH$_3$ |
| I.a.619. | OCH$_3$ | CH$_3$ | F | F | H |
| I.a.620. | OCH$_3$ | CH$_3$ | F | F | F |
| I.a.621. | OCH$_3$ | CH$_3$ | F | F | Cl |
| I.a.622. | OCH$_3$ | CH$_3$ | F | F | Br |
| I.a.623. | OCH$_3$ | CH$_3$ | F | F | CH$_3$ |
| I.a.624. | OCH$_3$ | CH$_3$ | F | F | OCH$_3$ |
| I.a.625. | OCH$_3$ | OCH$_3$ | H | H | H |
| I.a.626. | OCH$_3$ | OCH$_3$ | H | H | F |
| I.a.627. | OCH$_3$ | OCH$_3$ | H | H | Cl |
| I.a.628. | OCH$_3$ | OCH$_3$ | H | H | Br |
| I.a.629. | OCH$_3$ | OCH$_3$ | H | H | CH$_3$ |
| I.a.630. | OCH$_3$ | OCH$_3$ | H | H | OCH$_3$ |
| I.a.631. | OCH$_3$ | OCH$_3$ | H | F | H |
| I.a.632. | OCH$_3$ | OCH$_3$ | H | F | F |
| I.a.633. | OCH$_3$ | OCH$_3$ | H | F | Cl |
| I.a.634. | OCH$_3$ | OCH$_3$ | H | F | Br |
| I.a.635. | OCH$_3$ | OCH$_3$ | H | F | CH$_3$ |
| I.a.636. | OCH$_3$ | OCH$_3$ | H | F | OCH$_3$ |
| I.a.637. | OCH$_3$ | OCH$_3$ | F | H | H |
| I.a.638. | OCH$_3$ | OCH$_3$ | F | H | F |
| I.a.639. | OCH$_3$ | OCH$_3$ | F | H | Cl |
| I.a.640. | OCH$_3$ | OCH$_3$ | F | H | Br |
| I.a.641. | OCH$_3$ | OCH$_3$ | F | H | CH$_3$ |
| I.a.642. | OCH$_3$ | OCH$_3$ | F | H | OCH$_3$ |
| I.a.643. | OCH$_3$ | OCH$_3$ | F | F | H |
| I.a.644. | OCH$_3$ | OCH$_3$ | F | F | F |
| I.a.645. | OCH$_3$ | OCH$_3$ | F | F | Cl |
| I.a.646. | OCH$_3$ | OCH$_3$ | F | F | Br |
| I.a.647. | OCH$_3$ | OCH$_3$ | F | F | CH$_3$ |
| I.a.648. | OCH$_3$ | OCH$_3$ | F | F | OCH$_3$ |
| I.a.649. | OCH$_3$ | CF$_3$ | H | H | H |
| I.a.650. | OCH$_3$ | CF$_3$ | H | H | F |
| I.a.651. | OCH$_3$ | CF$_3$ | H | H | Cl |
| I.a.652. | OCH$_3$ | CF$_3$ | H | H | Br |
| I.a.653. | OCH$_3$ | CF$_3$ | H | H | CH$_3$ |
| I.a.654. | OCH$_3$ | CF$_3$ | H | H | OCH$_3$ |
| I.a.655. | OCH$_3$ | CF$_3$ | H | F | H |
| I.a.656. | OCH$_3$ | CF$_3$ | H | F | F |
| I.a.657. | OCH$_3$ | CF$_3$ | H | F | Cl |
| I.a.658. | OCH$_3$ | CF$_3$ | H | F | Br |
| I.a.659. | OCH$_3$ | CF$_3$ | H | F | CH$_3$ |
| I.a.660. | OCH$_3$ | CF$_3$ | H | F | OCH$_3$ |
| I.a.661. | OCH$_3$ | CF$_3$ | F | H | H |
| I.a.662. | OCH$_3$ | CF$_3$ | F | H | F |
| I.a.663. | OCH$_3$ | CF$_3$ | F | H | Cl |
| I.a.664. | OCH$_3$ | CF$_3$ | F | H | Br |
| I.a.665. | OCH$_3$ | CF$_3$ | F | H | CH$_3$ |
| I.a.666. | OCH$_3$ | CF$_3$ | F | H | OCH$_3$ |
| I.a.667. | OCH$_3$ | CF$_3$ | F | F | H |
| I.a.668. | OCH$_3$ | CF$_3$ | F | F | F |
| I.a.669. | OCH$_3$ | CF$_3$ | F | F | Cl |
| I.a.670. | OCH$_3$ | CF$_3$ | F | F | Br |

TABLE (I)-continued

| No. | $R^1$ | $R^3$ | $R^5$ | $R^6$ | $R^7$ |
|---|---|---|---|---|---|
| I.a.671. | $OCH_3$ | $CF_3$ | F | F | $CH_3$ |
| I.a.672. | $OCH_3$ | $CF_3$ | F | F | $OCH_3$ |

Also preferred is the use of the phenylpyrimidines of formula (I.b), particularly preferred the phenylpyrimidines of formulae (I.b.1) to (I.b.672), which differ from the corresponding phenylpyrimidines of formula (I.a) as well as formulae (I.a.1) to (I.a.672) only in that $R^2$ is $OCH_3$:

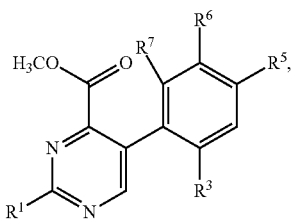
(I.b)

Also preferred is the use of the phenylpyrimidines of formula (I.c), particularly preferred the phenylpyrimidines of formulae (I.c.1) to (I.c.672), which differ from the corresponding phenylpyrimidines of formula (I.a) as well as formulae (I.a.1) to (I.a.672) only in that $R^2$ is $OC_2H_5$:

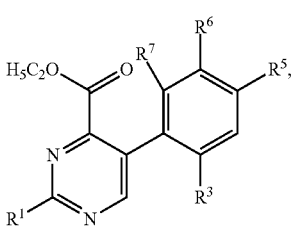
(I.c)

Also preferred is the use of the phenylpyrimidines of formula (I.d), particularly preferred the phenylpyrimidines of formulae (I.d.1) to (I.d.672, which differ from the corresponding phenylpyrimidines of formula (I.a) as well as formulae (I.a.1) to (I.a.672) only in that $R^2$ is $OCH_2C\equiv CH$:

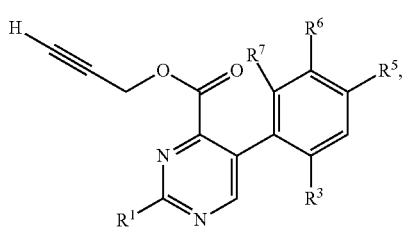
(I.d)

Also preferred is the use of the phenylpyrimidines of formula (I.e), particularly preferred the phenylpyrimidines of formulae (I.e.1) to (I.e.672), which differ from the corresponding phenylpyrimidines of formula (I.a) as well as formulae (I.a.1) to (I.a.672) only in that $R^2$ is $OCH_2CHF_2$:

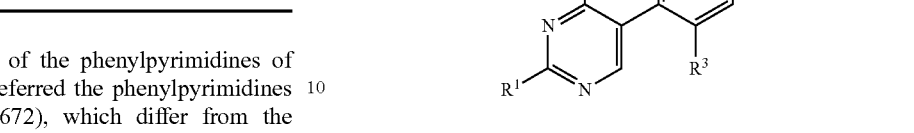
(I.e)

Particular preference is also given to the use of phenylpyrimidines of formula (I.1) (correspond to phenylpyrimidines of formula (I) wherein $R^4$ is H and $R^1$, $R^2$, $R^3$ $R^5$, $R^6$ and $R^7$ are as defined below),

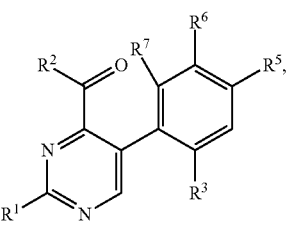
(I.1)

wherein $R^1$ is $C_3$-$C_6$-cycloalkyl, $C_1$-$C_6$-alkyl or $C_1$-$C_6$-alkoxy;
$R^2$ is OH, $C_1$-$C_6$-alkoxy, $C_2$-$C_6$-alkynyloxy or $C_1$-$C_6$-haloalkoxy;
$R^3$ is halogen, $C_1$-$C_6$-alkyl, $C_1$-$C_6$-haloalkyl or $C_1$-$C_6$-alkoxy;
$R^5$ is H or halogen;
$R^6$ is H or halogen; and
$R^7$ is H, halogen, $C_1$-$C_6$-alkyl or $C_1$-$C_6$-alkoxy.

Particular preference is also given to the use of phenylpyrimidines of formula (I.A) (correspond to phenylpyrimidines of formula (I.1) wherein $R^2$ is OH; correspond also to phenylpyrimidines of formula (I) wherein $R^2$ is OH, $R^4$ is H and $R^1$, $R^3$ $R^5$, $R^6$ and $R^7$ are as defined below),

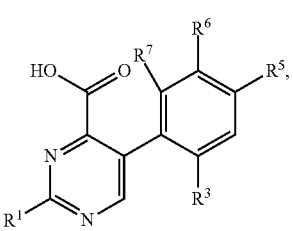
(I.A)

wherein $R^1$ is $C_3$-$C_6$-cycloalkyl, $C_1$-$C_6$-alkyl or $C_1$-$C_6$-alkoxy;
$R^3$ is halogen, $C_1$-$C_6$-alkyl, $C_1$-$C_6$-haloalkyl or $C_1$-$C_6$-alkoxy;
$R^5$ is H or halogen;
$R^6$ is H or halogen; and
$R^7$ is H, halogen, $C_1$-$C_6$-alkyl or $C_1$-$C_6$-alkoxy.

Also preferred is the use of phenylpyrimidines of formula (I.A.1) (correspond to phenylpyrimidines of formula (I.A) wherein $R^1$ is $C_3$-$C_6$-cycloalkyl; correspond also to phenylpyrimidines of formula (I.1) wherein $R^1$ is $C_3$-$C_6$-cycloalkyl and $R^2$ is OH; correspond also to phenylpyrimidines of formula (I) wherein $R^1$ is $C_3$-$C_6$-cycloalkyl, $R^2$ is OH, $R^4$ is H and $R^1$, $R^3$ $R^5$, $R^6$ and $R^7$ are as defined below),

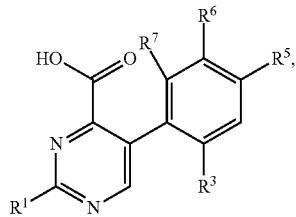

(I.A.1)

wherein $R^1$ is $C_3$-$C_6$-cycloalkyl;
$R^3$ is halogen, $C_1$-$C_6$-alkyl, $C_1$-$C_6$-haloalkyl or $C_1$-$C_6$-alkoxy;
$R^5$ is H or halogen;
$R^6$ is H or halogen; and
$R^7$ is H, halogen, $C_1$-$C_6$-alkyl or $C_1$-$C_6$-alkoxy;

particularly preferred the phenylpyrimidines of formulae (I.A.1.1) to (I.A.1.336), which correspond to the phenylpyrimidines of formulae (I.a.1) to (I.a.336) as defined above.

Particular preference is also given to the use of phenylpyrimidines of formula (I.B) (correspond to phenylpyrimidines of formula (I.1) wherein $R^2$ is $C_1$-$C_6$-alkoxy, $C_2$-$C_6$-alkynyloxy or $C_1$-$C_6$-haloalkoxy; correspond also to phenylpyrimidines of formula (I) wherein $R^2$ is $C_1$-$C_6$-alkoxy, $C_2$-$C_6$-alkynyloxy or $C_1$-$C_6$-haloalkoxy, $R^4$ is H and $R^1$, $R^3$ $R^5$, $R^6$ and $R^7$ are as defined below),

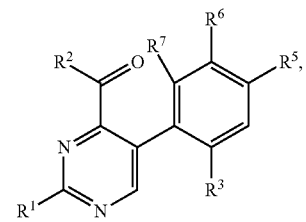

(I.B)

wherein $R^1$ is $C_3$-$C_6$-cycloalkyl, $C_1$-$C_6$-alkyl or $C_1$-$C_6$-alkoxy;
$R^2$ is $C_1$-$C_6$-alkoxy, $C_2$-$C_6$-alkynyloxy or $C_1$-$C_6$-haloalkoxy;
$R^3$ is halogen, $C_1$-$C_6$-alkyl, $C_1$-$C_6$-haloalkyl or $C_1$-$C_6$-alkoxy;
$R^5$ is H or halogen;
$R^6$ is H or halogen; and
$R^7$ is H, halogen, $C_1$-$C_6$-alkyl or $C_1$-$C_6$-alkoxy.

Also preferred is the use of phenylpyrimidines of formula (I.B.1) (correspond to phenylpyrimidines of formula (I.B) wherein $R^2$ is $OCH_3$, correspond also to phenylpyrimidines of formula (I.1) wherein $R^2$ is $OCH_3$; correspond also to phenylpyrimidines of formula (I) wherein $R^2$ is $OCH_3$, $R^4$ is H and $R^1$, $R^3$ $R^5$, $R^6$ and $R^7$ are as defined below),

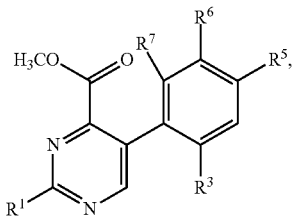

(I.B.1)

wherein $R^1$ is $C_3$-$C_6$-cycloalkyl, $C_1$-$C_6$-alkyl or $C_1$-$C_6$-alkoxy;
$R^3$ is halogen, $C_1$-$C_6$-alkyl, $C_1$-$C_6$-haloalkyl or $C_1$-$C_6$-alkoxy;
$R^5$ is H or halogen;
$R^6$ is H or halogen; and
$R^7$ is H, halogen, $C_1$-$C_6$-alkyl or $C_1$-$C_6$-alkoxy;

particularly preferred the phenylpyrimidines of formulae (I.B.1.1) to (I.B.1.672), which correspond to the phenylpyrimidines of formulae (I.b.1) to (I.b.672) as defined above.

Also preferred is the use of phenylpyrimidines of formula (I.B.2) (correspond to phenylpyrimidines of formula (I.B) wherein $R^2$ is $OC_2H_5$, correspond also to phenylpyrimidines of formula (I.1) wherein $R^2$ is $OC_2H_5$; correspond also to phenylpyrimidines of formula (I) wherein $R^2$ is $OC_2H_5$, $R^4$ is H and $R^1$, $R^3$ $R^5$, $R^6$ and $R^7$ are as defined below),

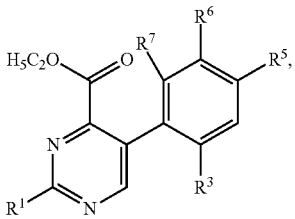

(I.B.2)

wherein $R^1$ is $C_3$-$C_6$-cycloalkyl, $C_1$-$C_6$-alkyl or $C_1$-$C_6$-alkoxy;
$R^3$ is halogen, $C_1$-$C_6$-alkyl, $C_1$-$C_6$-haloalkyl or $C_1$-$C_6$-alkoxy;
$R^5$ is H or halogen;
$R^6$ is H or halogen; and
$R^7$ is H, halogen, $C_1$-$C_6$-alkyl or $C_1$-$C_6$-alkoxy;

particularly preferred the phenylpyrimidines of formulae (I.B.2.1) to (I.B.2.672), which correspond to the phenylpyrimidines of formulae (I.c.1) to (I.c.672) as defined above.

Also preferred is the use of phenylpyrimidines of formula (I.B.3) (correspond to phenylpyrimidines of formula (I.B) wherein $R^2$ is $OCH_2C\equiv CH$, correspond also to phenylpyrimidines of formula (I.1) wherein $R^2$ is $OCH_2C\equiv CH$; correspond also to phenylpyrimidines of formula (I) wherein $R^2$ is $OCH_2C\equiv CH$, $R^4$ is H and $R^1$, $R^3$ $R^5$, $R^6$ and $R^7$ are as defined below),

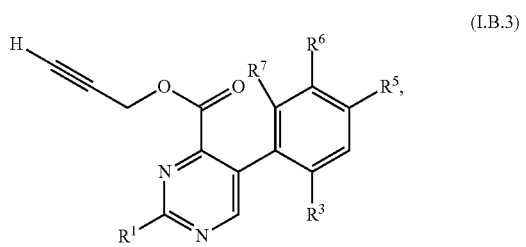

(I.B.3)

wherein R¹ is $C_3$-$C_6$-cycloalkyl, $C_1$-$C_6$-alkyl or $C_1$-$C_6$-alkoxy;

R³ is halogen, $C_1$-$C_6$-alkyl, $C_1$-$C_6$-haloalkyl or $C_1$-$C_6$-alkoxy;

R⁵ is H or halogen;

R⁶ is H or halogen; and

R⁷ is H, halogen, $C_1$-$C_6$-alkyl or $C_1$-$C_6$-alkoxy;

particularly preferred the phenylpyrimidines of formulae (I.B.3.1) to (I.B.3.672), which correspond to the phenylpyrimidines of formulae (I.d.1) to (I.d.672) as defined above.

Also preferred is the use of phenylpyrimidines of formula (I.B.4) (correspond to phenylpyrimidines of formula (I.B) wherein R² is $OCH_2CHF_2$, correspond also to phenylpyrimidines of formula (I.1) wherein R² is $OCH_2CHF_2$; correspond also to phenylpyrimidines of formula (I) wherein R² is $OCH_2CHF_2$, R⁴ is H and R¹, R³ R⁵, R⁶ and R⁷ are as defined below),

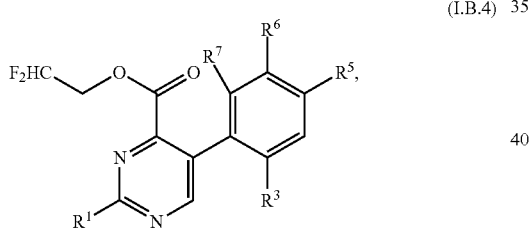

(I.B.4)

wherein R¹ is $C_3$-$C_6$-cycloalkyl, $C_1$-$C_6$-alkyl or $C_1$-$C_6$-alkoxy;

R³ is halogen, $C_1$-$C_6$-alkyl, $C_1$-$C_6$-haloalkyl or $C_1$-$C_6$-alkoxy;

R⁵ is H or halogen;

R⁶ is H or halogen; and

R⁷ is H, halogen, $C_1$-$C_6$-alkyl or $C_1$-$C_6$-alkoxy;

particularly preferred the phenylpyrimidines of formulae (I.B.4.1) to (I.B.4.672), which correspond to the phenylpyrimidines of formulae (I.e.1) to (I.e.672) as defined above.

The preferred embodiments of the invention mentioned herein below have to be understood as being preferred either independently from each other or in combination with one another.

While some phenylpyrimidine compounds are known in the art, particular phenylpyrimidines of formula (I) are novel. Accordingly, subject matter of the present invention are also phenylpyrimidines of formula (I)

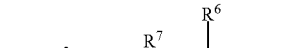

(I)

wherein in formula (I) the variables have the following meanings:

R¹ $C_1$-$C_6$-alkyl, $C_1$-$C_6$-haloalkyl, hydroxy-$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkinyloxy, $C_3$-$C_6$-haloalkinyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, phenyl, 5- or 6-membered heteroaryl, or 3- to 6-membered heterocyclyl wherein the cycloalkyl, phenyl, heteroaryl and heterocyclyl substituents independently of one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

R² H, halogen, $C_1$-$C_6$-alkyl, $C_1$-$C_6$-haloalkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkylcarbonyl-$C_1$-$C_6$-alkyl, $C_1$-$C_6$-haloalkoxycarbonyl-$C_1$-$C_6$-alkyl, $C_1$-$C_6$-alkylcarbonyl-$C_1$-$C_6$-haloalkyl, $C_1$-$C_6$-alkoxycarbonyl-$C_1$-$C_6$-haloalkyl, $C_1$-$C_6$-haloalkylcarbonyl-$C_1$-$C_6$-haloalkyl, $C_1$-$C_6$-haloalkoxycarbonyl-$C_1$-$C_6$-haloalkyl, OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy,
$C_1$-$C_6$-haloalkoxy, $C_1$-$C_6$-cyanoalkoxy, $C_1$-$C_6$-hydroxyalkoxy, $C_2$-$C_6$-alkenyloxy, $C_2$-$C_6$-alkenyloxy-$C_1$-$C_6$-alkoxy, $C_2$-$C_6$-haloalkenyloxy-$C_1$-$C_6$-haloalkoxy, $C_2$-$C_6$-alkenyloxy-$C_1$-$C_6$-haloalkoxy, $C_2$-$C_6$-haloalkenyloxy, $C_2$-$C_6$-alkynyloxy, $C_2$-$C_6$-haloalkynyloxy, $C_2$-$C_6$-alkynyloxy-$C_1$-$C_6$-alkoxy, $C_2$-$C_6$-haloalkynyloxy-$C_1$-$C_6$-haloalkoxy, $C_2$-$C_6$-alkynyloxy-$C_1$-$C_6$-haloalkoxy, $C_2$-$C_6$-alkynyloxy-$C_2$-$C_6$-alkenyloxy, $C_2$-$C_6$-haloalkynyloxy-$C_2$-$C_6$-alkenyloxy, $C_2$-$C_6$-alkynyloxy-$C_2$-$C_6$-haloalkenyloxy, $C_2$-$C_6$-haloalkynyloxy-$C_2$-$C_6$-haloalkenyloxy, $C_2$-$C_6$-alkynyloxy-$C_2$-$C_6$-alkynyloxy, $C_2$-$C_6$-haloalkynyloxy-$C_2$-$C_6$-alkynyloxy, $C_2$-$C_6$-alkynyloxy-$C_2$-$C_6$-haloalkynyloxy, $C_2$-$C_6$-haloalkynyloxy-$C_2$-$C_6$-haloalkynyloxy, ($C_1$-$C_6$-alkyl)carbonyl-$C_1$-$C_6$-alkoxy, ($C_1$-$C_6$-haloalkyl)carbonyl-$C_1$-$C_6$-haloalkoxy, ($C_1$-$C_6$-haloalkyl)carbonyl-$C_1$-$C_6$-alkoxy, ($C_1$-$C_6$- alkyl)carbonyl-C$_1$-C$_6$-haloalkoxy, (C$_1$-C$_6$-alkoxy)carbonyl-C$_1$-C$_6$-alkoxy, (C$_1$-C$_6$-haloalkoxy)carbonyl-C$_1$-C$_6$-alkoxy, (C$_1$-C$_6$-alkoxy)carbonyl-C$_1$-C$_6$-haloalkoxy, (C$_1$-C$_6$-haloalkoxy)carbonyl-C$_1$-C$_6$-haloalkoxy, (C$_1$-C$_6$-alkoxy-C$_1$-C$_6$-alkyl)carbonyl-C$_1$-C$_6$-alkoxy, (C$_1$-C$_6$-haloalkoxy-C$_1$-C$_6$-alkyl)carbonyl-C$_1$-C$_6$ (C$_1$-C$_6$-alkoxy-C$_1$-C$_6$-haloalkyl)carbonyl-C$_1$-C$_6$-alkoxy, (C$_1$-C$_6$-alkoxy-C$_1$-C$_6$-alkyl)carbonyl-C$_1$-C$_6$-haloalkoxy, (C$_1$-C$_6$-haloalkoxy-C$_1$-C$_6$-haloalkyl)carbonyl-C$_1$-C$_6$-alkoxy, (C$_1$-C$_6$-haloalkoxy-C$_1$-C$_6$-alkyl)carbonyl-C$_1$-C$_6$-haloalkoxy, (C$_1$-C$_6$-alkoxy-C$_1$-C$_6$-haloalkyl)carbonyl-C$_1$-C$_6$-haloalkoxy, (C$_1$-C$_6$-haloalkoxy-C$_1$-C$_6$-haloalkyl)carbonyl-C$_1$-C$_6$-haloalkoxy, (C$_1$-C$_6$-alkylthio)carbonyl-C$_1$-C$_6$-alkoxy, (C$_1$-C$_6$-haloalkylthio)carbonyl-C$_1$-C$_6$-alkoxy, (C$_1$-C$_6$-alkylthio)carbonyl-C$_1$-C$_6$-haloalkoxy, (C$_1$-C$_6$-haloalkylthio)carbonyl-C$_1$-C$_6$-haloalkoxy, (C$_1$-C$_6$-alkylthio-C$_1$-C$_6$-alkyl)carbonyl-C$_1$-C$_6$-alkoxy, (C$_1$-C$_6$-haloalkylthio-C$_1$-C$_6$-alkyl)carbonyl-C$_1$-C$_6$-alkoxy, (C$_1$-C$_6$-alkylthio-C$_1$-C$_6$-haloalkyl)carbonyl-C$_1$-C$_6$-alkoxy, (C$_1$-C$_6$-alkylthio-C$_1$-C$_6$-alkyl)carbonyl-C$_1$-C$_6$-haloalkoxy, (C$_1$-C$_6$-haloalkylthio-C$_1$-C$_6$-haloalkyl)carbonyl-C$_1$-C$_6$-alkoxy, (C$_1$-C$_6$-haloalkylthio-C$_1$-C$_6$-alkyl)carbonyl-C$_1$-C$_6$-haloalkoxy, (C$_1$-C$_6$-alkylthio-C$_1$-C$_6$-haloalkyl)carbonyl-C$_1$-C$_6$-haloalkoxy, (C$_1$-C$_6$-haloalkylthio-C$_1$-C$_6$-haloalkyl)carbonyl-C$_1$-C$_6$-haloalkoxy, C$_3$-C$_6$-cycloalkoxy, C$_3$-C$_6$-halocycloalkoxy, (C$_3$-C$_6$-cycloalkyl)C$_1$-C$_6$-alkoxy, (C$_3$-C$_6$-halocycloalkyl)C$_1$-C$_6$-alkoxy, (C$_3$-C$_6$-cycloalkyl)C$_1$-C$_6$-haloalkoxy, (C$_3$-C$_6$-halocycloalkyl)C$_1$-C$_6$-haloalkoxy, aminocarbonyl-C$_1$-C$_6$-alkoxy, aminocarbonyl-C$_1$-C$_6$-haloalkoxy, N—(C$_1$-C$_6$-alkyl)-aminocarbonyl-C$_1$-C$_6$-alkoxy, N—(C$_1$-C$_6$-alkyl)-aminocarbonyl-C$_1$-C$_6$-haloalkoxy, N,N-di(C$_1$-C$_6$-alkyl)-aminocarbonyl-C$_1$-C$_6$-alkoxy, N,N-di(C$_1$-C$_6$-alkyl)aminocarbonyl-C$_1$-C$_6$-haloalkoxy, O—N=C(di(phenyl), O—N=C(phenyl)(C$_1$-C$_6$-alkyl), O—N=C[di(C$_1$-C$_6$-alkyl)], (C$_1$-C$_6$-alkyl)$_3$-silyl-C$_1$-C$_6$-alkoxy, C$_1$-C$_6$-alkylthio, C$_1$-C$_6$-haloalkylthio, C$_1$-C$_6$-alkoxy-C$_1$-C$_6$-alkylthio, C$_1$-C$_6$-haloalkoxy-C$_1$-C$_6$-alkylthio, C$_1$-C$_6$-alkoxy-C$_1$-C$_6$-haloalkylthio, C$_1$-C$_6$-haloalkoxy-C$_1$-C$_6$-haloalkylthio, C$_1$-C$_6$-alkoxy-C$_1$-C$_6$-alkoxy-C$_1$-C$_6$-alkylthio, C$_1$-C$_6$-cyanoalkylthio, C$_2$-C$_6$-alkenylthio, C$_2$-C$_6$-haloalkenylthio, C$_2$-C$_6$-alkenyloxy-C$_1$-C$_6$-alkylthio, C$_2$-C$_6$-haloalkenyloxy-C$_1$-C$_6$-alkylthio, C$_2$-C$_6$-alkenyloxy-C$_1$-C$_6$-haloalkylthio, C$_2$-C$_6$-haloalkenyloxy-C$_1$-C$_6$-haloalkylthio, C$_2$-C$_6$-alkynylthio, C$_2$-C$_6$-haloalkynylthio, C$_2$-C$_6$-alkynyloxy-C$_1$-C$_6$-alkylthio, C$_2$-C$_6$-haloalkynyloxy-C$_1$-C$_6$-haloalkylthio, C$_2$-C$_6$-alkynyloxy-C$_1$-C$_6$-haloalkylthio, C$_2$-C$_6$-alkynyloxy-C$_2$-C$_6$-alkenylthio, C$_2$-C$_6$-haloalkynyloxy-C$_2$-C$_6$-alkenylthio, C$_2$-C$_6$-alkynyloxy-C$_2$-C$_6$-haloalkenylthio, C$_2$-C$_6$-haloalkynyloxy-C$_2$-C$_6$-haloalkenylthio, C$_2$-C$_6$-alkynyloxy-C$_2$-C$_6$-alkynylthio, C$_2$-C$_6$-haloalkynyloxy-C$_2$-C$_6$-alkynylthio, C$_2$-C$_6$-alkynyloxy-C$_2$-C$_6$-haloalkynylthio, C$_2$-C$_6$-haloalkynyloxy-C$_2$-C$_6$-haloalkynylthio, (C$_1$-C$_6$-alkyl)carbonyl-C$_1$-C$_6$-alkylthio, (C$_1$-C$_6$-haloalkyl)carbonyl-C$_1$-C$_6$-alkylthio, (C$_1$-C$_6$-alkyl)carbonyl-C$_1$-C$_6$-haloalkylthio, (C$_1$-C$_6$-haloalkyl)carbonyl-C$_1$-C$_6$-haloalkylthio, (C$_1$-C$_6$-alkoxy)carbonyl-C$_1$-C$_6$-alkylthio, (C$_1$-C$_6$-haloalkoxy)carbonyl-C$_1$-C$_6$-alkylthio, (C$_1$-C$_6$-alkoxy)carbonyl-C$_1$-C$_6$-haloalkylthio, (C$_1$-C$_6$-haloalkoxy)carbonyl-C$_1$-C$_6$-haloalkylthio, (C$_1$-C$_6$-alkoxy-C$_1$-C$_6$-alkyl)carbonyl-C$_1$-C$_6$-alkylthio, (C$_1$-C$_6$-alkoxy-C$_1$-C$_6$-haloalkyl)carbonyl-C$_1$-C$_6$-alkylthio, (C$_1$-C$_6$-alkoxy-C$_1$-C$_6$-alkyl)carbonyl-C$_1$-C$_6$-haloalkylthio, (C$_1$-C$_6$-haloalkoxy-C$_1$-C$_6$-alkyl)carbonyl-C$_1$-C$_6$-alkylthio, (C$_1$-C$_6$-alkoxy-C$_1$-C$_6$-haloalkyl)carbonyl-C$_1$-C$_6$-haloalkylthio, (C$_1$-C$_6$-haloalkoxy-C$_1$-C$_6$-alkyl)carbonyl-C$_1$-C$_6$-haloalkylthio, (C$_1$-C$_6$-haloalkoxy-C$_1$-C$_6$-haloalkyl)carbonyl-C$_1$-C$_6$-haloalkylthio, (C$_1$-C$_6$-alkylthio)carbonyl-C$_1$-C$_6$-alkylthio, (C$_1$-C$_6$-haloalkylthio)carbonyl-C$_1$-C$_6$-alkylthio, (C$_1$-C$_6$-alkylthio)carbonyl-C$_1$-C$_6$-haloalkylthio, (C$_1$-C$_6$-haloalkylthio)carbonyl-C$_1$-C$_6$-haloalkylthio, (C$_1$-C$_6$-alkylthio-C$_1$-C$_6$-alkyl)carbonyl-C$_1$-C$_6$-alkylthio, (C$_1$-C$_6$-haloalkylthio-C$_1$-C$_6$-alkyl)carbonyl-C$_1$-C$_6$-alkylthio, (C$_1$-C$_6$-alkylthio-C$_1$-C$_6$-haloalkyl)carbonyl-C$_1$-C$_6$-alkylthio, (C$_1$-C$_6$-alkylthio-C$_1$-C$_6$-alkyl)carbonyl-C$_1$-C$_6$-haloalkylthio, (C$_1$-C$_6$-haloalkylthio-C$_1$-C$_6$-haloalkyl)carbonyl-C$_1$-C$_6$-alkylthio, (C$_1$-C$_6$-haloalkylthio-C$_1$-C$_6$-alkyl)carbonyl-C$_1$-C$_6$-haloalkylthio, (C$_1$-C$_6$-alkylthio-C$_1$-C$_6$-haloalkyl)carbonyl-C$_1$-C$_6$-haloalkylthio, (C$_1$-C$_6$-haloalkylthio-C$_1$-C$_6$-haloalkyl)carbonyl-C$_1$-C$_6$-haloalkylthio, C$_3$-C$_6$-cycloalkylthio, C$_3$-C$_6$-halocycloalkylthio, (C$_3$-C$_6$-cycloalkyl)C$_1$-C$_6$-alkylthio, (C$_3$-C$_6$-cycloalkyl)C$_1$-C$_6$-haloalkylthio, (C$_3$-C$_6$-halocycloalkyl)C$_1$-C$_6$-alkylthio, (C$_3$-C$_6$-halocycloalkyl)C$_1$-C$_6$-haloalkylthio, aminocarbonyl-C$_1$-C$_6$-alkylthio, aminocarbonyl-C$_1$-C$_6$-haloalkylthio, N—(C$_1$-C$_6$-alkyl)-aminocarbonyl-C$_1$-C$_6$-alkylthio, N—(C$_1$-C$_6$-haloalkyl)aminocarbonyl-C$_1$-C$_6$-alkylthio, N—(C$_1$-C$_6$-alkyl)-aminocarbonyl-C$_1$-C$_6$-haloalkylthio, N—(C$_1$-C$_6$-haloalkyl)-aminocarbonyl-C$_1$-C$_6$-haloalkylthio, N,N-di(C$_1$-C$_6$-alkyl)-aminocarbonyl-C$_1$-C$_6$-alkylthio, N,N-di(C$_1$-C$_6$-haloalkyl)-aminocarbonyl-C$_1$-C$_6$-alkylthio, N,N-di(C$_1$-C$_6$-alkyl)aminocarbonyl-C$_1$-C$_6$-haloalkylthio, N,N-di(C$_1$-C$_6$-haloalkyl)-aminocarbonyl-C$_1$-C$_6$-haloalkylthio, NH$_2$, (C$_1$-C$_6$-alkyl)amino, hydroxyamino, (C$_1$-C$_6$-alkoxy)amino, (C$_3$-C$_6$-cycloalkoxy)amino, (C$_1$-C$_6$-alkyl)sulfinylamino, (C$_1$-C$_6$-alkyl)sulfonylamino, (amino)sulfinylamino, [(C$_1$-C$_6$-alkyl)amino]sulfinylamino, (amino)sulfonylamino, [(C$_1$-C$_6$-alkyl)amino]sulfonylamino, [di(C$_1$-C$_6$-alkyl)amino]sulfonylamino, di(C$_1$-C$_6$-alkyl)amino, (hydroxy)(C$_1$-C$_6$-alkyl)amino, (hydroxy)(C$_1$-C$_6$-cycloalkyl)amino, (C$_1$-C$_6$-alkoxy)(C$_1$-C$_6$-alkyl)amino, (C$_1$-C$_6$-alkoxy)(C$_3$-C$_6$-cycloalkyl)amino, (C$_3$-C$_6$-cycloalkoxy)(C$_1$-C$_6$-alkyl)amino, (C$_3$-C$_6$-cycloalkoxy)(C$_3$-C$_6$-cycloalkyl)amino, [(C$_1$-C$_6$-alkyl)sulfinyl](C$_1$-C$_6$-alkyl)amino, [(C$_1$-C$_6$-alkyl)sulfonyl](C$_1$-C$_6$-alkyl)amino, [di(C$_1$-C$_6$-alkyl)amino]sulfinylamino, [di(C$_1$-C$_6$-alkyl)amino]sulfonylamino, phenyloxy, phenyl-C$_1$-C$_6$-alkoxy, phenylthio, phenyl-C$_1$-C$_6$-alkylthio, phenylamino, (C$_1$-C$_6$-alkyl)(phenyl)amino, (heteroaryl)oxy, heteroaryl-C$_1$-C$_6$-alkoxy, (heterocyclyl)oxy, heterocyclyl-C$_1$-C$_6$-alkoxy, wherein the phenyl, heteroaryl and heterocyclyl substituents independently from one another are unsubstituted or substituted by one to five substituents selected from the group consisting of halogen, CN, NO$_2$, C$_1$-C$_6$-alkyl, C$_1$-C$_6$-haloalkyl, C$_1$-C$_6$-alkoxy or C$_1$-C$_6$-haloalkoxy;

R$^3$ halogen, CN, NO$_2$, C$_1$-C$_6$-alkyl, C$_1$-C$_6$-haloalkyl, C$_1$-C$_6$-alkylcarbonyl, C$_2$-C$_6$-alkenyl, C$_2$-C$_6$-haloalkenyl, C$_2$-C$_6$-alkinyl, C$_2$-C$_6$-haloalkinyl, C$_1$-C$_6$-alkoxy, C$_1$-C$_6$-haloalkoxy, C$_2$-C$_6$-alkenyloxy, C$_2$-C$_6$-haloalkenyloxy, C$_2$-C$_6$-alkinyloxy, C$_2$-C$_6$-haloalkinyloxy, C$_1$-C$_6$-alkoxy- $C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

and $R^4$, $R^5$, $R^6$ and $R^7$ independently of one another

H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkinyl, $C_2$-$C_6$-haloalkinyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkinyloxy, $C_2$-$C_6$-haloalkinyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

including their agriculturally acceptable salts or derivatives, provided the phenylpyrimidines of formula (I) have a carboxyl group;

provided that in case $R^2$ is OH, $R^1$ is not $C_1$-$C_6$-alkyl, hydroxy-$C_1$-$C_6$-alkyl, $C_1$-$C_6$-alkoxy or $C_1$-$C_6$-alkylthio, and with the exception of 5-(2-chloro-phenyl)-2-methylsulfanyl-pyrimidine-4-carboxylic acid ethyl ester;

2-methylsulfanyl-5-o-tolyl-pyrimidine-4-carboxylic acid ethyl ester;

5-(2-methoxy-phenyl)-2-methylsulfanyl-pyrimidine-4-carboxylic acid ethyl ester;

5-(4-fluoro-2-methyl-phenyl)-2-methylsulfanyl-pyrimidine-4-carboxylic acid ethyl ester;

5-(2-chloro-phenyl)-2-hydroxymethyl-pyrimidine-4-carboxylic acid ethyl ester.

According to a preferred embodiment of the invention preference is given to those phenylpyrimidines of formula (I), wherein the variables, either independently of one another or in combination with one another, have the following meanings:

Preferred are the phenylpyrimidines of formula (I), wherein in formula (I) the variables have the following meanings:

$R^1$ $C_1$-$C_6$-alkyl, $C_1$-$C_6$-haloalkyl, hydroxy-$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_1$-$C_6$-haloalkoxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, phenyl, 5- or 6-membered heteroaryl, or 3- to 6-membered heterocyclyl wherein the cycloalkyl, phenyl, heteroaryl and heterocyclyl substituents independently of one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^2$ H, halogen, $C_1$-$C_6$-alkyl, $C_1$-$C_6$-haloalkyl, OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy, $C_1$-$C_6$-haloalkoxy, $C_1$-$C_6$-cyanoalkoxy, $C_1$-$C_6$-hydroxyalkoxy, $C_2$-$C_6$-alkenyloxy, $C_2$-$C_6$-alkenyloxy-$C_1$-$C_6$-alkoxy, $C_2$-$C_6$-haloalkenyloxy-$C_1$-$C_6$-haloalkoxy, $C_2$-$C_6$-alkenyloxy-$C_1$-$C_6$-haloalkoxy, $C_2$-$C_6$-haloalkenyloxy, $C_2$-$C_6$-alkynyloxy, $C_2$-$C_6$-haloalkynyloxy, $C_2$-$C_6$-alkynyloxy-$C_1$-$C_6$-alkoxy, $C_2$-$C_6$-haloalkynyloxy-$C_1$-$C_6$-haloalkoxy, $C_2$-$C_6$-alkynyloxy-$C_1$-$C_6$-haloalkoxy, $C_2$-$C_6$-alkynyloxy-$C_2$-$C_6$-alkenyloxy, $C_2$-$C_6$-haloalkynyloxy-$C_2$-$C_6$-alkenyloxy, $C_2$-$C_6$-alkynyloxy-$C_2$-$C_6$-haloalkenyloxy, $C_2$-$C_6$-haloalkynyloxy-$C_2$-$C_6$-haloalkenyloxy, $C_2$-$C_6$-alkynyloxy-$C_2$-$C_6$-alkynyloxy, $C_2$-$C_6$-haloalkynyloxy-$C_2$-$C_6$-alkynyloxy, $C_2$-$C_6$-alkynyloxy-$C_2$-$C_6$-haloalkynyloxy, $C_2$-$C_6$-haloalkynyloxy-$C_2$-$C_6$-haloalkynyloxy, ($C_1$-$C_6$-alkyl)carbonyl-$C_1$-$C_6$-alkoxy, ($C_1$-$C_6$-haloalkyl)carbonyl-$C_1$-$C_6$-haloalkoxy, ($C_1$-$C_6$-haloalkyl)carbonyl-$C_1$-$C_6$-alkoxy, ($C_1$-$C_6$-alkyl)carbonyl-$C_1$-$C_6$-haloalkoxy, ($C_1$-$C_6$-alkoxy)carbonyl-$C_1$-$C_6$-alkoxy, ($C_1$-$C_6$-haloalkoxy)carbonyl-$C_1$-$C_6$-alkoxy, ($C_1$-$C_6$-alkoxy)carbonyl-$C_1$-$C_6$-haloalkoxy, ($C_1$-$C_6$-haloalkoxy)carbonyl-$C_1$-$C_6$-haloalkoxy, ($C_1$-$C_6$-alkoxy-$C_1$-$C_6$-alkyl)carbonyl-$C_1$-$C_6$-alkoxy, ($C_1$-$C_6$-haloalkoxy-$C_1$-$C_6$-alkyl)carbonyl-$C_1$-$C_6$-alkoxy, ($C_1$-$C_6$-alkoxy-$C_1$-$C_6$-haloalkyl)carbonyl-$C_1$-$C_6$-alkoxy, ($C_1$-$C_6$-alkoxy-$C_1$-$C_6$-alkyl)carbonyl-$C_1$-$C_6$-haloalkoxy, ($C_1$-$C_6$-haloalkoxy-$C_1$-$C_6$-haloalkyl)carbonyl-$C_1$-$C_6$-alkoxy, ($C_1$-$C_6$-haloalkoxy-$C_1$-$C_6$-alkyl)carbonyl-$C_1$-$C_6$-haloalkoxy, ($C_1$-$C_6$-alkoxy-$C_1$-$C_6$-haloalkyl)carbonyl-$C_1$-$C_6$-haloalkoxy, ($C_1$-$C_6$-haloalkoxy-$C_1$-$C_6$-haloalkyl)carbonyl-$C_1$-$C_6$-haloalkoxy, ($C_1$-$C_6$-alkylthio)carbonyl-$C_1$-$C_6$-alkoxy, ($C_1$-$C_6$-haloalkylthio)carbonyl-$C_1$-$C_6$-alkoxy, ($C_1$-$C_6$-alkylthio)carbonyl-$C_1$-$C_6$-haloalkoxy, ($C_1$-$C_6$-haloalkylthio)carbonyl-$C_1$-$C_6$-haloalkoxy, ($C_1$-$C_6$-alkylthio-$C_1$-$C_6$-alkyl)carbonyl-$C_1$-$C_6$-alkoxy, ($C_1$-$C_6$-haloalkylthio-$C_1$-$C_6$-alkyl)carbonyl-$C_1$-$C_6$-alkoxy, ($C_1$-$C_6$-alkylthio-$C_1$-$C_6$-haloalkyl)carbonyl-$C_1$-$C_6$-alkoxy, ($C_1$-$C_6$-alkylthio-$C_1$-$C_6$-alkyl)carbonyl-$C_1$-$C_6$-haloalkoxy, ($C_1$-$C_6$-haloalkylthio-$C_1$-$C_6$-haloalkyl)carbonyl-$C_1$-$C_6$-alkoxy, ($C_1$-$C_6$-haloalkylthio-$C_1$-$C_6$-alkyl)carbonyl-$C_1$-$C_6$-haloalkoxy, ($C_1$-$C_6$-alkylthio-$C_1$-$C_6$-haloalkyl)carbonyl-$C_1$-$C_6$-haloalkoxy, ($C_1$-$C_6$-haloalkylthio-$C_1$-$C_6$-haloalkyl)carbonyl-$C_1$-$C_6$-haloalkoxy, $C_3$-$C_6$-cycloalkoxy, ($C_3$-$C_6$-cycloalkyl)$C_1$-$C_6$-alkoxy, ($C_3$-$C_6$-cycloalkyl)$C_1$-$C_6$-haloalkoxy, aminocarbonyl-$C_1$-$C_6$-alkoxy, aminocarbonyl-$C_1$-$C_6$-haloalkoxy, N—($C_1$-$C_6$-alkyl)-aminocarbonyl-$C_1$-$C_6$-alkoxy, N—($C_1$-$C_6$-alkyl)-aminocarbonyl-$C_1$-$C_6$-haloalkoxy, N,N-di($C_1$-$C_6$-alkyl)-aminocarbonyl-$C_1$-$C_6$-alkoxy, N,N-di($C_1$-$C_6$-alkyl)-aminocarbonyl-$C_1$-$C_6$-haloalkoxy, O—N=C(di(phenyl), O—N=C(phenyl)($C_1$-$C_6$-alkyl), O—N=C[di($C_1$-$C_6$-alkyl)], ($C_1$-$C_6$-alkyl)$_3$-silyl-$C_1$-$C_6$-alkoxy, $C_1$-$C_6$-alkylthio, $C_1$-$C_6$-haloalkylthio, $C_1$-$C_6$-alkoxy-$C_1$-$C_6$-alkylthio, $C_1$-$C_6$-haloalkoxy-$C_1$-$C_6$-alkylthio, $C_1$-$C_6$-alkoxy-$C_1$-$C_6$-haloalkylthio, $C_1$-$C_6$-haloalkoxy-$C_1$-$C_6$-haloalkylthio, $C_1$-$C_6$-alkoxy-$C_1$-$C_6$-alkoxy-$C_1$-$C_6$-alkylthio, $C_1$-$C_6$-cyanoalkylthio, $C_2$-$C_6$-alkenylthio, $C_2$-$C_6$-haloalkenylthio, $C_2$-$C_6$-alkenyloxy-$C_1$-$C_6$-alkylthio, $C_2$-$C_6$-haloalkenyloxy-$C_1$-$C_6$-alkylthio, $C_2$-$C_6$-alkenyloxy-$C_1$-$C_6$-haloalkylthio, $C_2$-$C_6$-haloalkenyloxy-$C_1$-$C_6$-haloalkylthio, $C_2$-$C_6$-alkynylthio, $C_2$-$C_6$-haloalkynylthio, $C_2$-$C_6$-alkynyloxy-$C_1$-$C_6$-alkylthio, $C_2$-$C_6$-haloalkynyloxy-$C_1$-$C_6$-haloalkylthio, $C_2$-$C_6$-alkynyloxy-$C_1$-$C_6$-haloalkylthio, $C_2$-$C_6$-alkynyloxy-$C_2$-$C_6$-alkenylthio, $C_2$-$C_6$-haloalkynyloxy-$C_2$-$C_6$-alkenylthio, $C_2$-$C_6$-alkynyloxy-$C_2$-$C_6$-haloalkenylthio, $C_2$-$C_6$-haloalkynyloxy-$C_2$-$C_6$-haloalkenylthio, $C_2$-$C_6$-alkynyloxy-$C_2$-$C_6$-alkynylthio, $C_2$-$C_6$-haloalkynyloxy-$C_2$-$C_6$-alkynylthio, $C_2$-$C_6$-alkynyloxy-$C_2$-$C_6$-haloalkynylthio, $C_2$-$C_6$-haloalkynyloxy-$C_2$-$C_6$-haloalkynylthio, ($C_1$-$C_6$-alkyl)carbonyl-$C_1$-$C_6$-alkylthio, ($C_1$-$C_6$-haloalkyl)carbonyl-$C_1$-$C_6$-alkylthio, ($C_1$-$C_6$-alkyl)carbonyl-$C_1$-$C_6$-haloalkylthio, ($C_1$-$C_6$-haloalkyl)carbonyl-$C_1$-$C_6$-haloalkylthio, ($C_1$-$C_6$-alkoxy)carbonyl-$C_1$-$C_6$-alkylthio, ($C_1$-$C_6$-haloalkoxy)carbonyl-$C_1$-$C_6$-alkylthio, ($C_1$-$C_6$-alkoxy)carbonyl-$C_1$-$C_6$-haloalkylthio, ($C_1$-$C_6$-haloalkoxy)carbonyl-$C_1$-$C_6$-haloalkylthio, ($C_1$-$C_6$-alkoxy-$C_1$-$C_6$-alkyl)carbonyl-$C_1$-$C_6$-alkylthio, ($C_1$-$C_6$-haloalkoxy-$C_1$-$C_6$-alkyl)carbonyl-$C_1$-$C_6$-alkylthio, ($C_1$-$C_6$-alkoxy-$C_1$-$C_6$-haloalkyl)carbonyl-$C_1$-$C_6$-alkylthio, ($C_1$-$C_6$-alkoxy-$C_1$-$C_6$-alkyl)carbonyl-$C_1$-$C_6$-haloalkylthio, ($C_1$-$C_6$-haloalkoxy-$C_1$-$C_6$-haloalkyl)carbonyl-$C_1$-$C_6$-alkylthio, ($C_1$-$C_6$-haloalkoxy-$C_1$-$C_6$-alkyl)carbonyl-$C_1$-$C_6$-haloalkylthio, ($C_1$-$C_6$-alkoxy-$C_1$-$C_6$-haloalkyl)carbonyl-$C_1$-$C_6$-haloalkylthio, ($C_1$-$C_6$-haloalkoxy-$C_1$-$C_6$-haloalkyl)carbonyl-$C_1$-$C_6$-haloalkylthio, ($C_1$-$C_6$-alkylthio)carbonyl-$C_1$-$C_6$-alkylthio, ($C_1$-$C_6$-haloalkylthio)carbonyl-$C_1$-$C_6$-alkylthio, ($C_1$-$C_6$-alkylthio)carbonyl-$C_1$-$C_6$-haloalkylthio, ($C_1$-$C_6$-haloalkylthio)carbonyl-$C_1$-$C_6$-haloalkylthio, ($C_1$-$C_6$-alkylthio-$C_1$-$C_6$-alkyl)carbonyl-$C_1$-$C_6$-alkylthio, ($C_1$-$C_6$-haloalkylthio-$C_1$-$C_6$-alkyl)carbonyl-$C_1$-$C_6$-alkylthio, ($C_1$-$C_6$-alkylthio-$C_1$-$C_6$-haloalkyl)carbonyl-$C_1$-$C_6$-alkylthio, ($C_1$-$C_6$-alkylthio-$C_1$-$C_6$-alkyl)carbonyl-$C_1$-$C_6$-haloalkylthio, ($C_1$-$C_6$-haloalkylthio-$C_1$-$C_6$-haloalkyl)carbonyl-$C_1$-$C_6$-alkylthio, ($C_1$-$C_6$-haloalkylthio-$C_1$-$C_6$-alkyl)carbonyl-$C_1$-$C_6$-haloalkylthio, ($C_1$-$C_6$-alkylthio-$C_1$-$C_6$-haloalkyl)carbonyl-$C_1$-$C_6$-haloalkylthio, ($C_1$-$C_6$-haloalkylthio-$C_1$-$C_6$-haloalkyl)carbonyl-$C_1$-$C_6$-haloalkylthio, $C_3$-$C_6$-cycloalkylthio, ($C_3$-$C_6$-cycloalkyl)$C_1$-$C_6$-alkylthio, ($C_3$-$C_6$-cycloalkyl)$C_1$-$C_6$-haloalkylthio, aminocarbonyl-$C_1$-$C_6$-alkylthio, aminocarbonyl-$C_1$-$C_6$-haloalkylthio, N—($C_1$-$C_6$-alkyl)-aminocarbonyl-$C_1$-$C_6$-alkylthio, N—($C_1$-$C_6$-haloalkyl)-aminocarbonyl-$C_1$-$C_6$-alkylthio, N—($C_1$-$C_6$-alkyl)-aminocarbonyl-$C_1$-$C_6$-haloalkylthio, N—($C_1$-$C_6$-haloalkyl)-aminocarbonyl-$C_1$-$C_6$-haloalkylthio, N,N-di($C_1$-$C_6$-alkyl)-aminocarbonyl-$C_1$-$C_6$-alkylthio, N,N-di($C_1$-$C_6$-haloalkyl)-aminocarbonyl-$C_1$-$C_6$-alkylthio, N,N-di($C_1$-$C_6$-alkyl)aminocarbonyl-$C_1$-$C_6$-haloalkylthio, N,N-di($C_1$-$C_6$-haloalkyl)-aminocarbonyl-$C_1$-$C_6$-haloalkylthio, $NH_2$, ($C_1$-$C_6$-alkyl)amino, hydroxyamino, ($C_1$-$C_6$-alkoxy)amino, ($C_3$-$C_6$-cycloalkoxy)amino, ($C_1$-$C_6$-alkyl)sulfinylamino, ($C_1$-$C_6$-alkyl)sulfonylamino, (amino)sulfinylamino, [($C_1$-$C_6$-alkyl)amino]sulfinylamino, (amino)sulfonylamino, [($C_1$-$C_6$-alkyl) amino]sulfonylamino, [di($C_1$-$C_6$-alkyl)amino]sulfonylamino, di($C_1$-$C_6$-alkyl)amino, (hydroxy)($C_1$-$C_6$-alkyl)amino, (hydroxy)($C_1$-$C_6$-cycloalkyl)amino, ($C_1$-$C_6$-alkoxy)($C_1$-$C_6$-alkyl)amino, ($C_1$-$C_6$-alkoxy)($C_3$-$C_6$-cycloalkyl)amino, ($C_3$-$C_6$-cycloalkoxy)($C_1$-$C_6$-alkyl)amino, ($C_3$-$C_6$-cycloalkoxy)($C_3$-$C_6$-cycloalkyl)amino, [($C_1$-$C_6$-alkyl)sulfinyl]($C_1$-$C_6$-alkyl)amino, [($C_1$-$C_6$-alkyl)sulfonyl]($C_1$-$C_6$-alkyl)amino, [di($C_1$-$C_6$-alkyl)amino]sulfinylamino, [di($C_1$-$C_6$-alkyl)amino]sulfonylamino, phenyloxy, phenyl-$C_1$-$C_6$-alkoxy, phenylthio, phenyl-$C_1$-$C_6$-alkylthio, phenylamino, ($C_1$-$C_6$-alkyl)(phenyl)amino, (heteroaryl)oxy, heteroaryl-$C_1$-$C_6$-alkoxy, (heterocyclyl)oxy, heterocyclyl-$C_1$-$C_6$-alkoxy, wherein the phenyl, heteroaryl and heterocyclyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^3$ halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_1$-$C_6$-alkoxy, $C_1$-$C_6$-haloalkoxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

and $R^4$, $R^5$, $R^6$ and $R^7$ independently of one another
halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_1$-$C_6$-alkoxy, $C_1$-$C_6$-haloalkoxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

including their agriculturally acceptable salts or derivatives, provided the phenylpyrimidines of formula (I) have a carboxyl group;

provided that in case $R^2$ is OH, $R^1$ is not $C_1$-$C_6$-alkyl, hydroxy-$C_1$-$C_6$-alkyl, $C_1$-$C_6$-alkoxy or $C_1$-$C_6$-alkylthio, and with the exception of 5-(2-chloro-phenyl)-2-methylsulfanyl-pyrimidine-4-carboxylic acid ethyl ester;

2-methylsulfanyl-5-o-tolyl-pyrimidine-4-carboxylic acid ethyl ester;

5-(2-methoxy-phenyl)-2-methylsulfanyl-pyrimidine-4-carboxylic acid ethyl ester;

5-(4-fluoro-2-methyl-phenyl)-2-methylsulfanyl-pyrimidine-4-carboxylic acid ethyl ester;

5-(2-chloro-phenyl)-2-hydroxymethyl-pyrimidine-4-carboxylic acid ethyl ester.

Also preferred are the phenylpyrimidines of formula (I), wherein
$R^1$ is $C_1$-$C_6$-alkyl, $C_1$-$C_6$-alkoxy, $C_1$-$C_6$-haloalkoxy, $C_2$-$C_6$-alkenyloxy, $C_2$-$C_6$-haloalkenyloxy $C_2$-$C_6$-alkinyloxy, $C_2$-$C_6$-haloalkinyloxy, $C_1$-$C_6$-alkylthio, $C_3$-$C_6$-cycloalkyl or phenyl,
 wherein the cycloalkyl or phenyl substituent is unsubstituted;
 particularly preferred $C_1$-$C_6$-alkyl, $C_1$-$C_6$-alkoxy or $C_3$-$C_6$-cycloalkyl,
 wherein the cycloalkyl substituent is unsubstituted;
 especially preferred $C_3$-$C_6$-cycloalkyl,
 wherein the cycloalkyl substituent is unsubstituted;
 also especially preferred $C_2H_5$, i-$C_3H_7$, i-$C_4H_9$, $OCH_3$, c-$C_3H_5$ or c-$C_4H_9$;
 more preferred $C_2H_5$, $OCH_3$ or c-$C_3H_5$;
 most preferred c-$C_3H_5$.

Also preferred are the phenylpyrimidines of formula (I), wherein
$R^1$ is $C_1$-$C_6$-alkyl, $C_1$-$C_6$-alkoxy, $C_1$-$C_6$-haloalkoxy, $C_1$-$C_6$-alkylthio, $C_3$-$C_6$-cycloalkyl or phenyl,
 wherein the cycloalkyl or phenyl substituent is unsubstituted;
 particularly preferred $C_1$-$C_6$-alkyl, $C_1$-$C_6$-alkoxy or $C_3$-$C_6$-cycloalkyl,
 wherein the cycloalkyl substituent is unsubstituted;
 especially preferred $C_3$-$C_6$-cycloalkyl,
 wherein the cycloalkyl substituent is unsubstituted;
 also especially preferred $C_2H_5$, i-$C_3H_7$, i-$C_4Hg$, $OCH_3$, c-$C_3H_5$ or c-$C_4H_9$;
 more preferred $C_2H_5$, $OCH_3$ or c-$C_3H_5$;
 most preferred c-$C_3H_5$.

Also preferred are the phenylpyrimidines of formula (I), wherein
$R^2$ is OH, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, ($C_1$-$C_6$-alkoxy)carbonyl-$C_1$-$C_6$-alkoxy, $C_1$-$C_6$-alkylthio, ($C_1$-$C_6$-alkoxy)carbonyl-$C_1$-$C_6$-alkylthio, $NH_2$, ($C_1$-$C_6$-alkyl)amino, ($C_1$-$C_6$-alkyl)sulfonylamino, [di($C_1$-$C_6$-alkyl)amino]sulfonylamino, phenyloxy, phenyl-$C_1$-$C_6$-alkoxy or phenyl-$C_1$-$C_6$-alkylthio,
 wherein the phenyl substituent is unsubstituted;
 preferably OH, $C_1$-$C_6$-alkoxy, $C_1$-$C_6$-haloalkoxy, $C_2$-$C_6$-alkynyloxy, ($C_1$-$C_6$-alkoxy)carbonyl-$C_1$-$C_6$-alkoxy, $C_1$-$C_6$-alkylthio, ($C_1$-$C_6$-alkoxy)carbonyl-$C_1$-$C_6$-alkylthio, $NH_2$, ($C_1$-$C_6$-alkyl)amino, ($C_1$-$C_6$-alkyl)sulfonylamino, [di($C_1$-$C_6$-alkyl)amino]sulfonylamino, phenyloxy, phenyl-$C_1$-$C_6$-alkoxy or phenyl-$C_1$-$C_6$-alkylthio,
 wherein the phenyl substituent is unsubstituted;
 particularly preferred OH, $C_1$-$C_6$-alkoxy, $C_1$-$C_6$-haloalkoxy, $C_2$-$C_6$-alkynyloxy, $C_1$-$C_6$-alkylthio, phenyloxy or phenyl-$C_1$-$C_6$-alkoxy,
 wherein the phenyl substituent is unsubstituted;
 also particularly preferred OH, $C_1$-$C_6$-alkoxy, $C_2$-$C_6$-alkynyloxy or $C_1$-$C_6$-haloalkoxy;
 especially preferred $C_1$-$C_6$-alkoxy, $C_2$-$C_6$-alkynyloxy or $C_1$-$C_6$-haloalkoxy;
 also especially preferred OH, $C_1$-$C_6$-alkoxy or $C_1$-$C_6$-haloalkoxy;
 more preferred OH or $C_1$-$C_6$-alkoxy,
 most preferred OH,
 also most preferred $C_1$-$C_6$-alkoxy.

Also preferred are the phenylpyrimidines of formula (I), wherein
$R^3$ is halogen, CN, $NO_2$, $C_1$-$C_6$-alkyl, $C_1$-$C_6$-haloalkyl, $C_1$-$C_6$-alkoxy or $C_3$-$C_6$-cycloalkyl;

also preferred halogen, CN, $C_1$-$C_6$-alkyl, $C_1$-$C_6$-haloalkyl or $C_1$-$C_6$-alkoxy,
 particularly preferred halogen CN, $C_1$-$C_6$-alkyl or $C_1$-$C_6$-alkoxy;
 especially preferred halogen or $CH_3$;
 also especially preferred halogen;
 more preferred Cl, Br or I;
 most preferred Br or I.

Also preferred are the phenylpyrimidines of formula (I), wherein
$R^4$, $R^5$, $R^6$ and $R^7$ independently of one another are
 H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_1$-$C_6$-alkoxy, $C_1$-$C_6$-haloalkoxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl) oxy or phenyl;
 wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy.

Also preferred are the phenylpyrimidines of formula (I), wherein
$R^4$ is H, halogen, CN, $C_1$-$C_6$-alkyl, $C_1$-$C_6$-haloalkyl or $C_1$-$C_6$-alkoxy;
 particularly preferred H, halogen or $C_1$-$C_6$-alkyl,
 especially preferred H or halogen;
 more preferred H or F;
 most preferred H;
 also most preferred F.

Also preferred are the phenylpyrimidines of formula (I), wherein
$R^5$ is H, halogen, CN, $C_1$-$C_6$-alkyl, $C_1$-$C_6$-haloalkyl or $C_1$-$C_6$-alkoxy;
 particularly preferred H, halogen, $C_1$-$C_6$-alkyl $C_1$-$C_6$-haloalkyl or $C_1$-$C_6$-alkoxy;
 especially preferred H, halogen, $C_1$-$C_6$-alkyl or $C_1$-$C_6$-alkoxy;
 more preferred H, F, Cl, $CH_3$ or $OCH_3$;
 also more preferred H or halogen;
 most preferred H or F;
 also most preferred H;
 also most preferred F.

Also preferred are the phenylpyrimidines of formula (I), wherein
$R^6$ is H, halogen, $C_1$-$C_6$-alkyl or $C_1$-$C_6$-alkoxy;
 particularly preferred H, halogen or $C_1$-$C_6$-alkyl;
 especially preferred H, halogen or $CH_3$;
 more preferred H or halogen;
 most preferred H or F;
 also most preferred H;
 also most preferred F.

Also preferred are the phenylpyrimidines of formula (I), wherein
$R^7$ is H, halogen, CN, $C_1$-$C_6$-alkyl or $C_1$-$C_6$-alkoxy;
 particularly preferred H, halogen, $C_1$-$C_6$-alkyl or $C_1$-$C_6$-alkoxy;
 especially preferred H, halogen or $C_1$-$C_6$-alkyl;
 more preferred H, F, Cl or $CH_3$;
 most preferred H, F or Cl;
 also most preferred $CH_3$;
 also most preferred H.

Particular preference is also given to the phenylpyrimidines of formula (I.1) (correspond to phenylpyrimidines of formula (I) wherein $R^4$ is H and $R^1$, $R^2$, $R^3$ $R^5$, $R^6$ and $R^7$ are as defined below),

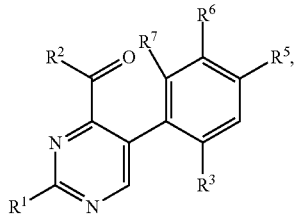

(I.1)

wherein $R^1$ is $C_3$-$C_6$-cycloalkyl, $C_1$-$C_6$-alkyl or $C_1$-$C_6$-alkoxy;

$R^2$ is OH, $C_1$-$C_6$-alkoxy, $C_2$-$C_6$-alkynyloxy or $C_1$-$C_6$-haloalkoxy;

$R^3$ is halogen, $C_1$-$C_6$-alkyl, $C_1$-$C_6$-haloalkyl or $C_1$-$C_6$-alkoxy;

$R^5$ is H or halogen;

$R^6$ is H or halogen; and $R^7$ is H, halogen, $C_1$-$C_6$-alkyl or $C_1$-$C_6$-alkoxy;

provided that in case $R^2$ is OH, $R^1$ is not $C_1$-$C_6$-alkyl or $C_1$-$C_6$-alkoxy.

Also preferred are the phenylpyrimidines of formula (I.A.1) (correspond to phenylpyrimidines of formula (I.A) wherein $R^1$ is $C_3$-$C_6$-cycloalkyl; correspond also to phenylpyrimidines of formula (I.1) wherein $R^1$ is $C_3$-$C_6$-cycloalkyl and $R^2$ is OH; correspond also to phenylpyrimidines of formula (I) wherein $R^1$ is $C_3$-$C_6$-cycloalkyl, $R^2$ is OH, $R^4$ is H and $R^1$, $R^3$ $R^5$, $R^6$ and $R^7$ are as defined below),

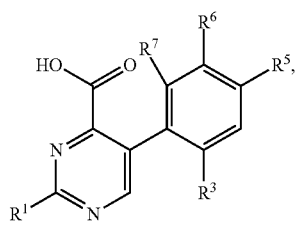

(I.A.1)

wherein $R^1$ is $C_3$-$C_6$-cycloalkyl;

$R^3$ is halogen, $C_1$-$C_6$-alkyl, $C_1$-$C_6$-haloalkyl or $C_1$-$C_6$-alkoxy;

$R^5$ is H or halogen;

$R^6$ is H or halogen; and $R^7$ is H, halogen, $C_1$-$C_6$-alkyl or $C_1$-$C_6$-alkoxy;

particularly preferred the phenylpyrimidines of formulae (I.A.1.1) to (I.A.1.336), which correspond to the phenylpyrimidines of formulae (I.a.1) to (I.a.336) as defined above.

Particular preference is also given to the phenylpyrimidines of formula (I.B) (correspond to phenylpyrimidines of formula (I.1) wherein $R^2$ is $C_1$-$C_6$-alkoxy, $C_2$-$C_6$-alkynyloxy or $C_1$-$C_6$-haloalkoxy; correspond also to phenylpyrimidines of formula (I) wherein $R^2$ is $C_1$-$C_6$-alkoxy, $C_2$-$C_6$-alkynyloxy or $C_1$-$C_6$-haloalkoxy, $R^4$ is H and $R^1$, $R^3$ $R^5$, $R^6$ and $R^7$ are as defined below),

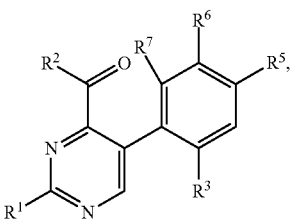

(I.B)

wherein $R^1$ is $C_3$-$C_6$-cycloalkyl, $C_1$-$C_6$-alkyl or $C_1$-$C_6$-alkoxy;

$R^2$ is $C_1$-$C_6$-alkoxy, $C_2$-$C_6$-alkynyloxy or $C_1$-$C_6$-haloalkoxy;

$R^3$ is halogen, $C_1$-$C_6$-alkyl, $C_1$-$C_6$-haloalkyl or $C_1$-$C_6$-alkoxy;

$R^5$ is H or halogen;

$R^6$ is H or halogen; and $R^7$ is H, halogen, $C_1$-$C_6$-alkyl or $C_1$-$C_6$-alkoxy.

Also preferred are the phenylpyrimidines of formula (I.B.1) (correspond to phenylpyrimidines of formula (I.B) wherein $R^2$ is $OCH_3$, correspond also to phenylpyrimidines of formula (I.1) wherein $R^2$ is $OCH_3$; correspond also to phenylpyrimidines of formula (I) wherein $R^2$ is $OCH_3$, $R^4$ is H and $R^1$, $R^3$ $R^5$, $R^6$ and $R^7$ are as defined below),

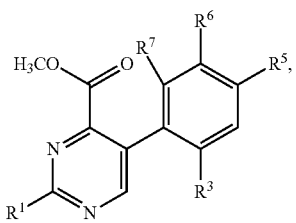

(I.B.1)

wherein $R^1$ is $C_3$-$C_6$-cycloalkyl, $C_1$-$C_6$-alkyl or $C_1$-$C_6$-alkoxy;

$R^3$ is halogen, $C_1$-$C_6$-alkyl, $C_1$-$C_6$-haloalkyl or $C_1$-$C_6$-alkoxy;

$R^5$ is H or halogen;

$R^6$ is H or halogen; and $R^7$ is H, halogen, $C_1$-$C_6$-alkyl or $C_1$-$C_6$-alkoxy;

particularly preferred the phenylpyrimidines of formulae (I.B.1.1) to (I.B.1.672), which correspond to the phenylpyrimidines of formulae (I.b.1) to (I.b.672) as defined above.

Also preferred are the phenylpyrimidines of formula (I.B.2) (correspond to phenylpyrimidines of formula (I.B) wherein $R^2$ is $OC_2H_5$, correspond also to phenylpyrimidines of formula (I.1) wherein $R^2$ is $OC_2H_5$; correspond also to phenylpyrimidines of formula (I) wherein $R^2$ is $OC_2H_5$, $R^4$ is H and $R^1$, $R^3$ $R^5$, $R^6$ and $R^7$ are as defined below),

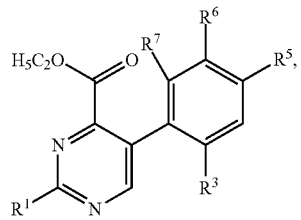

(I.B.2)

wherein $R^1$ is $C_3$-$C_6$-cycloalkyl, $C_1$-$C_6$-alkyl or $C_1$-$C_6$-alkoxy;
$R^3$ is halogen, $C_1$-$C_6$-alkyl, $C_1$-$C_6$-haloalkyl or $C_1$-$C_6$-alkoxy;
$R^5$ is H or halogen;
$R^6$ is H or halogen; and
$R^7$ is H, halogen, $C_1$-$C_6$-alkyl or $C_1$-$C_6$-alkoxy;
particularly preferred the phenylpyrimidines of formulae (I.B.2.1) to (I.B.2.672), which correspond to the phenylpyrimidines of formulae (I.c.1) to (I.c.672) as defined above.

Also preferred are the phenylpyrimidines of formula (I.B.3) (correspond to phenylpyrimidines of formula (I.B) wherein $R^2$ is $OCH_2C\equiv CH$, correspond also to phenylpyrimidines of formula (I.1) wherein $R^2$ is $OCH_2C\equiv CH$; correspond also to phenylpyrimidines of formula (I) wherein $R^2$ is $OCH_2C\equiv CH$, $R^4$ is H and $R^1$, $R^3$ $R^5$, $R^6$ and $R^7$ are as defined below),

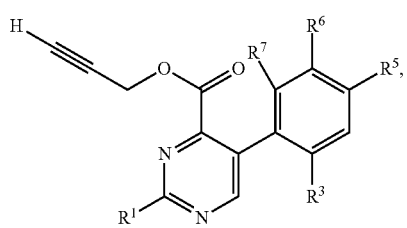

(I.B.3)

wherein $R^1$ is $C_3$-$C_6$-cycloalkyl, $C_1$-$C_6$-alkyl or $C_1$-$C_6$-alkoxy;
$R^3$ is halogen, $C_1$-$C_6$-alkyl, $C_1$-$C_6$-haloalkyl or $C_1$-$C_6$-alkoxy;
$R^5$ is H or halogen;
$R^6$ is H or halogen; and
$R^7$ is H, halogen, $C_1$-$C_6$-alkyl or $C_1$-$C_6$-alkoxy;
particularly preferred the phenylpyrimidines of formulae (I.B.3.1) to (I.B.3.672), which correspond to the phenylpyrimidines of formulae (I.d.1) to (I.d.672) as defined above.

Also preferred are the phenylpyrimidines of formula (I.B.4) (correspond to phenylpyrimidines of formula (I.B) wherein $R^2$ is $OCH_2CHF_2$, correspond also to phenylpyrimidines of formula (I.1) wherein $R^2$ is $OCH_2CHF_2$; correspond also to phenylpyrimidines of formula (I) wherein $R^2$ is $OCH_2CHF_2$, $R^4$ is H and $R^1$, $R^3$ $R^5$, $R^6$ and $R^7$ are as defined below),

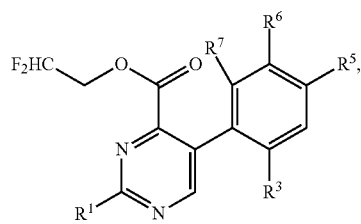

(I.B.4)

wherein $R^1$ is $C_3$-$C_6$-cycloalkyl, $C_1$-$C_6$-alkyl or $C_1$-$C_6$-alkoxy;
$R^3$ is halogen, $C_1$-$C_6$-alkyl, $C_1$-$C_6$-haloalkyl or $C_1$-$C_6$-alkoxy;
$R^5$ is H or halogen;
$R^6$ is H or halogen; and
$R^7$ is H, halogen, $C_1$-$C_6$-alkyl or $C_1$-$C_6$-alkoxy;

particularly preferred the phenylpyrimidines of formulae (I.B.4.1) to (I.B.4.672), which correspond to the phenylpyrimidines of formulae (I.e.1) to (I.e.672) as defined above.

The phenylpyrimidine of formula (I) according to the invention can be prepared by standard processes of organic chemistry, for example by the following processes:

Process A)

The phenylpyrimidines of formula (I) can be obtained by reacting respective pyrimidines of formula (II) with boronic acids of formula (III):

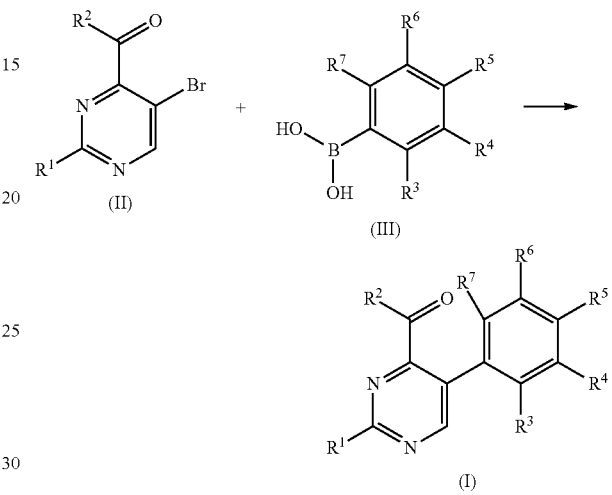

The reaction of the pyridine (II) with boronic acids (III) is usually carried out at from 0° C. to the boiling point of the reaction mixture, preferably at from 15° C. to 110° C., particularly preferably at from 20° C. to 60° C., in an inert organic solvent in the presence of a base and a catalyst.

The reaction may in principle be carried out in substance. However, preference is given to reacting the pyrimidines (II) with the boronic acids (III) in an organic solvent.

Suitable in principle are all solvents which are capable of dissolving the pyrimidines (II) and the boronic acids (III) at least partly and preferably fully under reaction conditions.

Examples of suitable solvents are aromatic hydrocarbons such as benzene, chlorobenzene, toluene, cresols, o-, m- and p-xylene, ethers such as diethyl ether, diisopropyl ether, tert.-butyl methylether (TBME), dioxane, anisole and tetrahydrofuran (THF), as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers such as diethyl ether, diisopropyl ether, tert.-butyl methylether (TBME), dioxane, anisole and tetrahydrofuran (THF) and dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethyl-propylene urea (DMPU), dimethyl sulfoxide (DMSO) and 1-methyl-2 pyrroli-dinone (NMP).

More preferred solvents are ethers such as diethyl ether, diisopropyl ether, tert.-butyl methylether (TBME), dioxane, anisole and tetrahydrofuran (THF).

It is also possible to use mixtures of the solvents mentioned.

Examples of suitable metal-containing bases are inorganic compounds including metal-containing bases such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal carbonates such as lithium carbonate, sodium carbonate, potassium carbonate, cesium carbonate magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate.

Preferred bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide and alkali metal and alkaline earth metal carbonates such as lithium carbonate, sodium carbonate, potassium carbonate, cesium carbonate, magnesium carbonate, and calcium carbonate.

Especially preferred bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide.

The term base as used herein also includes mixtures of two or more, preferably two of the above compounds. Particular preference is given to the use of one base.

The bases are used preferably at from 1 to 10 equivalents based on the pyrimidine (II), more preferably at from 1.0 to 5.0 equivalents based on the pyrimidine (II), most preferably from 1.2 to 2.5 equivalents based on the pyrimidine (II).

It may be advantageous to add the base offset over a period of time.

The reaction of the pyridines (II) with the boronic acids (II) is carried out in the presence of a catalyst. Examples of suitable catalysts include for example, palladium based catalysts like, for example, Palladium(II)acetate, tetrakis(triphenylphosphine)palladium(0), bis(triphenylphosphine)palladium(II)chloride or (1,1,-bis(diphenylphosphino)ferrocene)dichloropalladium(II), and optionally suitable additives such as, for example, phosphines like, for example, P(o-tolyl)3, tr phenylphosphine or BINAP (2,2'-Bis(diphenylphospino)-1,1'-binaphthyl).

The amount of catalyst is usually 10 to 20 mol % (0.1 to 0.2 equivalents) based on the pyrimidine (II).

As an alternative, phenylpyrimidines (I), wherein $R^2$ has any one of the above mentioned meanings except OH, can also be obtained by modifying phenylpyrimidines (I) wherein $R^2$ is OH by known methods (e.g. "oxy-substituents" except "OH" analogous to Arnab, P. et. al. Angew. Chem. Int. Ed. 2010, 49, 1492-1495; "thio-substituents" analogous to Silvestri, M. A. et. al. J. Med. Chem. 2004, 47, 3149-3162; "amino-substituents" analogous to Kuhn, B. et. al. J. Med. Chem. 2010, 53, 2601-2611).

The end of the reaction can easily be determined by the skilled worker by means of routine methods.

The reaction mixtures are worked up in a customary manner, for example by mixing with water, separation of the phases and, if appropriate, chromatographic purification of the crude product. Some of the intermediates and end products are obtained in the form of viscous oils, which can be purified or freed from volatile components under reduced pressure and at moderately elevated temperature.

If the intermediates and the end products are obtained as solid, purification can also be carried out by recrystallisation or digestion.

The pyrimidines (II) wherein $R^2$ is OH are known from the literature (e.g. WO 06/004532) or are commercially available.

To obtain the other pyrimidines (II), wherein $R^2$ has any one of the above mentioned meanings except OH, the pyrimidines (II) wherein $R^2$ is OH can easily be modified by known methods (e.g. "oxy-substituents" except "OH" analogous to Arnab, P. et. al. Angew. Chem. Int. Ed. 2010, 49, 1492-1495; "thio-substituents" analogous to Silvestri, M. A. et. al. J. Med. Chem. 2004, 47, 3149-3162; "amino-substituents" analogous to Kuhn, B. et. al. J. Med. Chem. 2010, 53, 2601-2611).

The boronic acids (Ill) required for the preparation of phenylpyrimidines of formula (I) are known from the literature or are commercially available.

Particular pyrimidines of formula (II) are novel compounds and as shown above suitable intermediates for the preparation of the phenylpyrimidines of formula (I) according to the present invention.

Therefore the present invention also provides pyrimidines of formula (II)

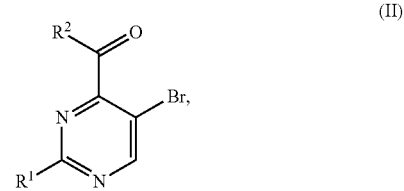

wherein the variables have the following meanings:
$R^1$ $C_1$-$C_6$-alkyl, $C_1$-$C_6$-haloalkyl, hydroxy-$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkinyloxy, $C_3$-$C_6$-haloalkinyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-halocycloalkyl, $C_3$-$C_6$-halocycloalkenyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, phenyl, 5- or 6-membered heteroaryl, or 3- to 6-membered heterocyclyl
wherein the cycloalkyl, phenyl, heteroaryl and heterocyclyl substituents independently of one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;
$R^2$ H, halogen, $C_1$-$C_6$-alkyl, $C_1$-$C_6$-haloalkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkylcarbonyl-$C_1$-$C_6$-alkyl, $C_1$-$C_6$-haloalkoxycarbonyl-$C_1$-$C_6$-alkyl, $C_1$-$C_6$-alkylcarbonyl-$C_1$-

C$_6$-haloalkyl, C$_1$-C$_6$-alkoxycarbonyl-C$_1$-C$_6$-haloalkyl, C$_1$-C$_6$-haloalkylcarbonyl-C$_1$-C$_6$-haloalkyl, C$_1$-C$_6$-haloalkoxycarbonyl-C$_1$-C$_6$-haloalkyl, OH, C$_1$-C$_6$-alkoxy, C$_1$-C$_6$-alkoxy-C$_1$-C$_6$-alkoxy, C$_1$-C$_6$-haloalkoxy-C$_1$-C$_6$-alkoxy, C$_1$-C$_6$-alkoxy-C$_1$-C$_6$-haloalkoxy, C$_1$-C$_6$-haloalkoxy-C$_1$-C$_6$-haloalkoxy, C$_1$-C$_6$-alkoxy-C$_1$-C$_6$-alkoxy-C$_1$-C$_6$-alkoxy, C$_1$-C$_6$-haloalkoxy, C$_1$-C$_6$-cyanoalkoxy, C$_1$-C$_6$-hydroxyalkoxy, C$_2$-C$_6$-alkenyloxy, C$_2$-C$_6$-alkenyloxy-C$_1$-C$_6$-alkoxy, C$_2$-C$_6$-haloalkenyloxy-C$_1$-C$_6$-haloalkoxy, C$_2$-C$_6$-alkenyloxy-C$_1$-C$_6$-haloalkoxy, C$_2$-C$_6$-haloalkenyloxy, C$_2$-C$_6$-alkynyloxy, C$_2$-C$_6$-haloalkynyloxy, C$_2$-C$_6$-alkynyloxy-C$_1$-C$_6$-alkoxy, C$_2$-C$_6$-haloalkynyloxy-C$_1$-C$_6$-haloalkoxy, C$_2$-C$_6$-alkynyloxy-C$_1$-C$_6$-haloalkoxy, C$_2$-C$_6$-alkynyloxy-C$_2$-C$_6$-alkenyloxy, C$_2$-C$_6$-haloalkynyloxy-C$_2$-C$_6$-alkenyloxy, C$_2$-C$_6$-alkynyloxy-C$_2$-C$_6$-haloalkenyloxy, C$_2$-C$_6$-haloalkynyloxy-C$_2$-C$_6$-haloalkenyloxy, C$_2$-C$_6$-alkynyloxy-C$_2$-C$_6$-alkynyloxy, C$_2$-C$_6$-haloalkynyloxy-C$_2$-C$_6$-alkynyloxy, C$_2$-C$_6$-alkynyloxy-C$_2$-C$_6$-haloalkynyloxy, C$_2$-C$_6$-haloalkynyloxy-C$_2$-C$_6$-haloalkynyloxy, (C$_1$-C$_6$-alkyl)carbonyl-C$_1$-C$_6$-alkoxy, (C$_1$-C$_6$-haloalkyl)carbonyl-C$_1$-C$_6$-haloalkoxy, (C$_1$-C$_6$-haloalkyl)carbonyl-C$_1$-C$_6$-alkoxy, (C$_1$-C$_6$-alkyl)carbonyl-C$_1$-C$_6$-haloalkoxy, (C$_1$-C$_6$-alkoxy)carbonyl-C$_1$-C$_6$-alkoxy, (C$_1$-C$_6$-alkoxy)carbonyl-C$_1$-C$_6$-haloalkoxy, (C$_1$-C$_6$-haloalkoxy)carbonyl-C$_1$-C$_6$-haloalkoxy, (C$_1$-C$_6$-alkoxy-C$_1$-C$_6$-alkyl)carbonyl-C$_1$-C$_6$-alkoxy, (C$_1$-C$_6$-haloalkoxy-C$_1$-C$_6$-alkyl)carbonyl-C$_1$-C$_6$-alkoxy, (C$_1$-C$_6$-alkoxy-C$_1$-C$_6$-haloalkyl)carbonyl-C$_6$-alkoxy, (C$_1$-C$_6$-alkoxy-C$_1$-C$_6$-alkyl)carbonyl-C$_1$-C$_6$-haloalkoxy, (C$_1$-C$_6$-haloalkoxy-C$_1$-C$_6$-haloalkyl)carbonyl-C$_1$-C$_6$-alkoxy, (C$_1$-C$_6$-haloalkoxy-C$_1$-C$_6$-alkyl)carbonyl-C$_1$-C$_6$-haloalkoxy, (C$_1$-C$_6$-alkoxy-C$_1$-C$_6$-haloalkyl)carbonyl-C$_1$-C$_6$-haloalkoxy, (C$_1$-C$_6$-haloalkoxy-C$_1$-C$_6$-haloalkyl)carbonyl-C$_1$-C$_6$-haloalkoxy, (C$_1$-C$_6$-alkylthio)carbonyl-C$_1$-C$_6$-alkoxy, (C$_1$-C$_6$-haloalkylthio)carbonyl-C$_1$-C$_6$-alkoxy, (C$_1$-C$_6$-alkylthio)carbonyl-C$_1$-C$_6$-haloalkoxy, (C$_1$-C$_6$-haloalkylthio)carbonyl-C$_1$-C$_6$-haloalkoxy, (C$_1$-C$_6$-alkylthio-C$_1$-C$_6$-alkyl)carbonyl-C$_1$-C$_6$-alkoxy, (C$_1$-C$_6$-haloalkylthio-C$_1$-C$_6$-alkyl)carbonyl-C$_1$-C$_6$-alkoxy, (C$_1$-C$_6$-alkylthio-C$_1$-C$_6$-haloalkyl)carbonyl-C$_1$-C$_6$-alkoxy, (C$_1$-C$_6$-alkylthio-C$_1$-C$_6$-alkyl)carbonyl-C$_1$-C$_6$-haloalkoxy, (C$_1$-C$_6$-haloalkylthio-C$_1$-C$_6$-haloalkyl)carbonyl-C$_1$-C$_6$-alkoxy, (C$_1$-C$_6$-haloalkylthio-C$_1$-C$_6$-alkyl)carbonyl-C$_1$-C$_6$-haloalkoxy, (C$_1$-C$_6$-alkylthio-C$_1$-C$_6$-haloalkyl)carbonyl-C$_1$-C$_6$-haloalkoxy, (C$_1$-C$_6$-haloalkylthio-C$_1$-C$_6$-haloalkyl)carbonyl-C$_1$-C$_6$-haloalkoxy, C$_3$-C$_6$-cycloalkoxy, C$_3$-C$_6$-halocycloalkoxy, (C$_3$-C$_6$-cycloalkyl)C$_1$-C$_6$-alkoxy, (C$_3$-C$_6$-halocycloalkyl)C$_1$-C$_6$-alkoxy, (C$_3$-C$_6$-cycloalkyl)C$_1$-C$_6$-haloalkoxy, (C$_3$-C$_6$-halocycloalkyl)C$_1$-C$_6$-haloalkoxy, aminocarbonyl-C$_1$-C$_6$-alkoxy, aminocarbonyl-C$_1$-C$_6$-haloalkoxy, N—(C$_1$-C$_6$-alkyl)-aminocarbonyl-C$_1$-C$_6$-alkoxy, N—(C$_1$-C$_6$-alkyl)-aminocarbonyl-C$_1$-C$_6$-haloalkoxy, N,N-di(C$_1$-C$_6$-alkyl)aminocarbonyl-C$_1$-C$_6$-alkoxy, N,N-di(C$_1$-C$_6$-alkyl)-aminocarbonyl-C$_1$-C$_6$-haloalkoxy, O—N=C(di(phenyl), O—N=C(phenyl)(C$_1$-C$_6$-alkyl), O—N=C[di(C$_1$-C$_6$-alkyl)], (C$_1$-C$_6$-alkyl)$_3$-silyl-C$_1$-C$_6$-alkoxy, C$_1$-C$_6$-alkylthio, C$_1$-C$_6$-haloalkylthio, C$_1$-C$_6$-alkoxy-C$_1$-C$_6$-alkylthio, C$_1$-C$_6$-haloalkoxy-C$_1$-C$_6$-alkylthio, C$_1$-C$_6$-alkoxy-C$_1$-C$_6$-haloalkylthio, C$_1$-C$_6$-haloalkoxy-C$_1$-C$_6$-haloalkylthio, C$_1$-C$_6$-alkoxy-C$_1$-C$_6$-alkoxy-C$_1$-C$_6$-alkylthio, C$_1$-C$_6$-cyanoalkylthio, C$_2$-C$_6$-alkenylthio, C$_2$-C$_6$-haloalkenylthio, C$_2$-C$_6$-alkenyloxy-C$_1$-C$_6$-alkylthio, C$_2$-C$_6$-haloalkenyloxy-C$_1$-C$_6$-alkylthio, C$_2$-C$_6$-alkenyloxy-C$_1$-C$_6$-haloalkylthio, C$_2$-C$_6$-haloalkenyloxy-C$_1$-C$_6$-haloalkylthio, C$_2$-C$_6$-alkynylthio, C$_2$-C$_6$-haloalkynylthio, C$_2$-C$_6$-alkynyloxy-C$_1$-C$_6$-alkylthio, C$_2$-C$_6$-haloalkynyloxy-C$_1$-C$_6$-alkylthio, C$_2$-C$_6$-alkynyloxy-C$_1$-C$_6$-haloalkylthio, C$_2$-C$_6$-haloalkynyloxy-C$_1$-C$_6$-haloalkylthio, C$_2$-C$_6$-alkynyloxy-C$_2$-C$_6$-alkenylthio, C$_2$-C$_6$-haloalkynyloxy-C$_2$-C$_6$-alkenylthio, C$_2$-C$_6$-alkynyloxy-C$_2$-C$_6$-haloalkenylthio, C$_2$-C$_6$-haloalkynyloxy-C$_2$-C$_6$-haloalkenylthio, C$_2$-C$_6$-alkynyloxy-C$_2$-C$_6$-alkynylthio, C$_2$-C$_6$-haloalkynyloxy-C$_2$-C$_6$-alkynylthio, C$_2$-C$_6$-alkynyloxy-C$_2$-C$_6$-haloalkynylthio, C$_2$-C$_6$-haloalkynyloxy-C$_2$-C$_6$-haloalkynylthio, (C$_1$-C$_6$-alkyl)carbonyl-C$_1$-C$_6$-alkylthio, (C$_1$-C$_6$-haloalkyl)carbonyl-C$_1$-C$_6$-alkylthio, (C$_1$-C$_6$-alkyl)carbonyl-C$_1$-C$_6$-haloalkylthio, (C$_1$-C$_6$-haloalkyl)carbonyl-C$_1$-C$_6$-haloalkylthio, (C$_1$-C$_6$-alkoxy)carbonyl-C$_1$-C$_6$-alkylthio, (C$_1$-C$_6$-haloalkoxy)carbonyl-C$_1$-C$_6$-alkylthio, (C$_1$-C$_6$-alkoxy)carbonyl-C$_1$-C$_6$-haloalkylthio, (C$_1$-C$_6$-haloalkoxy)carbonyl-C$_1$-C$_6$-haloalkylthio, (C$_1$-C$_6$-alkoxy-C$_1$-C$_6$-alkyl)carbonyl-C$_1$-C$_6$-alkylthio, (C$_1$-C$_6$-haloalkoxy-C$_1$-C$_6$-alkyl)carbonyl-C$_1$-C$_6$-alkylthio, (C$_1$-C$_6$-alkoxy-C$_1$-C$_6$-haloalkyl)carbonyl-C$_1$-C$_6$-alkylthio, (C$_1$-C$_6$-alkoxy-C$_1$-C$_6$-alkyl)carbonyl-C$_1$-C$_6$-haloalkylthio, (C$_1$-C$_6$-haloalkoxy-C$_1$-C$_6$-haloalkyl)carbonyl-C$_1$-C$_6$-alkylthio, (C$_1$-C$_6$-haloalkoxy-C$_1$-C$_6$-alkyl)carbonyl-C$_1$-C$_6$-haloalkylthio, (C$_1$-C$_6$-alkoxy-C$_1$-C$_6$-haloalkyl)carbonyl-C$_1$-C$_6$-haloalkylthio, (C$_1$-C$_6$-haloalkoxy-C$_1$-C$_6$-haloalkyl)carbonyl-C$_1$-C$_6$-haloalkylthio, (C$_1$-C$_6$-alkylthio)carbonyl-C$_1$-C$_6$-alkylthio, (C$_1$-C$_6$-haloalkylthio)carbonyl-C$_1$-C$_6$-alkylthio, (C$_1$-C$_6$-alkylthio)carbonyl-C$_1$-C$_6$-haloalkylthio, (C$_1$-C$_6$-haloalkylthio)carbonyl-C$_1$-C$_6$-haloalkylthio, (C$_1$-C$_6$-alkylthio-C$_1$-C$_6$-alkyl)carbonyl-C$_1$-C$_6$-alkylthio, (C$_1$-C$_6$-haloalkylthio-C$_1$-C$_6$-alkyl)carbonyl-C$_1$-C$_6$-alkylthio, (C$_1$-C$_6$-alkylthio-C$_1$-C$_6$-haloalkyl)carbonyl-C$_1$-C$_6$-alkylthio, (C$_1$-C$_6$-alkylthio-C$_1$-C$_6$-alkyl)carbonyl-C$_1$-C$_6$-haloalkylthio, (C$_1$-C$_6$-haloalkylthio-C$_1$-C$_6$-haloalkyl)carbonyl-C$_1$-C$_6$-alkylthio, (C$_1$-C$_6$-haloalkylthio-C$_1$-C$_6$-alkyl)carbonyl-C$_1$-C$_6$-haloalkylthio, (C$_1$-C$_6$-alkylthio-C$_1$-C$_6$-haloalkyl)carbonyl-C$_1$-C$_6$-haloalkylthio, (C$_1$-C$_6$-haloalkylthio-C$_1$-C$_6$-haloalkyl)carbonyl-C$_1$-C$_6$-haloalkylthio, C$_3$-C$_6$-cycloalkylthio, C$_3$-C$_6$-halocycloalkylthio, (C$_3$-C$_6$-cycloalkyl)C$_1$-C$_6$-alkylthio, (C$_3$-C$_6$-halocycloalkyl)C$_1$-C$_6$-alkylthio, (C$_3$-C$_6$-cycloalkyl)C$_1$-C$_6$-haloalkylthio, (C$_3$-C$_6$-halocycloalkyl)C$_1$-C$_6$-haloalkylthio, aminocarbonyl-C$_1$-C$_6$-alkylthio, aminocarbonyl-C$_1$-C$_6$-haloalkylthio, N—(C$_1$-C$_6$-alkyl)-aminocarbonyl-C$_1$-C$_6$-alkylthio, N—(C$_1$-C$_6$-haloalkyl)aminocarbonyl-C$_1$-C$_6$-alkylthio, N—(C$_1$-C$_6$-alkyl)-aminocarbonyl-C$_1$-C$_6$-haloalkylthio, N—(C$_1$-C$_6$-haloalkyl)-aminocarbonyl-C$_1$-C$_6$-haloalkylthio, N,N-di(C$_1$-C$_6$-alkyl)-aminocarbonyl-C$_1$-C$_6$-alkylthio, N,N-di(C$_1$-C$_6$-haloalkyl)-aminocarbonyl-C$_1$-C$_6$-alkylthio, N,N-di(C$_1$-C$_6$-alkyl)aminocarbonyl-C$_1$-C$_6$-haloalkylthio, N,N-di(C$_1$-C$_6$-haloalkyl)-aminocarbonyl-C$_1$-C$_6$-haloalkylthio, NH$_2$, (C$_1$-C$_6$-alkyl)amino, hydroxyamino, (C$_1$-C$_6$-alkoxy)amino, (C$_3$-C$_6$-cycloalkoxy)amino, (C$_1$-C$_6$-alkyl)sulfinylamino, (C$_1$-C$_6$-alkyl)sulfonylamino, (amino)sulfinylamino, [(C$_1$-C$_6$-alkyl)amino]sulfinylamino, (amino)sulfonylamino, [(C$_1$-C$_6$-alkyl)amino]sulfonylamino, [di(C$_1$-C$_6$-alkyl)amino]sulfonylamino, di(C$_1$-C$_6$-alkyl)amino, (hydroxy)(C$_1$-C$_6$-alkyl)amino, (hydroxy)(C$_1$-C$_6$-cycloalkyl)amino, (C$_1$-C$_6$-alkoxy)(C$_1$-C$_6$-alkyl)amino, (C$_1$-C$_6$-alkoxy)(C$_3$-C$_6$-cycloalkyl)amino, (C$_3$-C$_6$-cycloalkoxy)(C$_1$-C$_6$- alkyl)amino, ($C_3$-$C_6$-cycloalkoxy)($C_3$-$C_6$-cycloalkyl)amino, [($C_1$-$C_6$-alkyl)sulfinyl]($C_1$-$C_6$-alkyl)amino, [($C_1$-$C_6$-alkyl)sulfonyl]($C_1$-$C_6$-alkyl)amino, [di($C_1$-$C_6$-alkyl)amino]sulfinylamino, [di($C_1$-$C_6$-alkyl)amino]sulfonylamino, phenyloxy, phenyl-$C_1$-$C_6$-alkoxy, phenylthio, phenyl-$C_1$-$C_6$-alkylthio, phenylamino, ($C_1$-$C_6$-alkyl)(phenyl)amino, (heteroaryl)oxy, heteroaryl-$C_1$-$C_6$-alkoxy, (heterocyclyl)oxy, heterocyclyl-$C_1$-$C_6$-alkoxy,
  wherein the phenyl, heteroaryl and heterocyclyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;
provided that in case $R^2$ is OH, $R^1$ is not $C_1$-$C_6$-alkyl, hydroxy-$C_1$-$C_6$-alkyl, $C_1$-$C_6$-alkoxy or $C_1$-$C_6$-alkylthio.

Preferred are the pyrimidines of formula (II), wherein the variables have the following meanings:

$R^1$ $C_1$-$C_6$-alkyl, $C_1$-$C_6$-haloalkyl, hydroxy-$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_1$-$C_6$-haloalkoxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, phenyl, 5- or 6-membered heteroaryl, or 3- to 6-membered heterocyclyl
  wherein the cycloalkyl, phenyl, heteroaryl and heterocyclyl substituents independently of one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^2$ H, halogen, $C_1$-$C_6$-alkyl, $C_1$-$C_6$-haloalkyl, OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy, $C_1$-$C_6$-haloalkoxy, $C_1$-$C_6$-cyanoalkoxy, $C_1$-$C_6$-hydroxyalkoxy, $C_2$-$C_6$-alkenyloxy, $C_2$-$C_6$-alkenyloxy-$C_1$-$C_6$-alkoxy, $C_2$-$C_6$-haloalkenyloxy-$C_1$-$C_6$-haloalkoxy, $C_2$-$C_6$-alkenyloxy-$C_1$-$C_6$-haloalkoxy, $C_2$-$C_6$-haloalkenyloxy, $C_2$-$C_6$-alkynyloxy, $C_2$-$C_6$-haloalkynyloxy, $C_2$-$C_6$-alkynyloxy-$C_1$-$C_6$-alkoxy, $C_2$-$C_6$-haloalkynyloxy-$C_1$-$C_6$-haloalkoxy, $C_2$-$C_6$-alkynyloxy-$C_1$-$C_6$-haloalkoxy, $C_2$-$C_6$-alkynyloxy-$C_2$-$C_6$-alkenyloxy, $C_2$-$C_6$-haloalkynyloxy-$C_2$-$C_6$-alkenyloxy, $C_2$-$C_6$-alkynyloxy-$C_2$-$C_6$-haloalkenyloxy, $C_2$-$C_6$-haloalkynyloxy-$C_2$-$C_6$-haloalkenyloxy, $C_2$-$C_6$-alkynyloxy-$C_2$-$C_6$-alkynyloxy, $C_2$-$C_6$-alkynyloxy-$C_2$-$C_6$-haloalkynyloxy, $C_2$-$C_6$-haloalkynyloxy-$C_2$-$C_6$-haloalkynyloxy, ($C_1$-$C_6$-alkyl)carbonyl-$C_1$-$C_6$-alkoxy, ($C_1$-$C_6$-haloalkyl)carbonyl-$C_1$-$C_6$-haloalkoxy, ($C_1$-$C_6$-haloalkyl)carbonyl-$C_1$-$C_6$-alkoxy, ($C_1$-$C_6$-alkyl)carbonyl-$C_1$-$C_6$-haloalkoxy, ($C_1$-$C_6$-alkoxy)carbonyl-$C_1$-$C_6$-alkoxy, ($C_1$-$C_6$-haloalkoxy)carbonyl-$C_1$-$C_6$-alkoxy, ($C_1$-$C_6$-alkoxy)carbonyl-$C_1$-$C_6$-haloalkoxy, ($C_1$-$C_6$-haloalkoxy)carbonyl-$C_1$-$C_6$-haloalkoxy, ($C_1$-$C_6$-alkoxy-$C_1$-$C_6$-alkyl)carbonyl-$C_1$-$C_6$-alkoxy, ($C_1$-$C_6$-haloalkoxy-$C_1$-$C_6$-alkyl)carbonyl-$C_1$-$C_6$-alkoxy, ($C_1$-$C_6$-alkoxy-$C_1$-$C_6$-haloalkyl)carbonyl-$C_1$-$C_6$-alkoxy, ($C_1$-$C_6$-alkoxy-$C_1$-$C_6$-alkyl)carbonyl-$C_1$-$C_6$-haloalkoxy, ($C_1$-$C_6$-haloalkoxy-$C_1$-$C_6$-alkyl)carbonyl-$C_1$-$C_6$-haloalkoxy, ($C_1$-$C_6$-alkoxy-$C_1$-$C_6$-haloalkyl)carbonyl-$C_1$-$C_6$-haloalkoxy, ($C_1$-$C_6$-haloalkoxy-$C_1$-$C_6$-haloalkyl)carbonyl-$C_1$-$C_6$-haloalkoxy, ($C_1$-$C_6$-alkylthio)carbonyl-$C_1$-$C_6$-alkoxy, ($C_1$-$C_6$-haloalkylthio)carbonyl-$C_1$-$C_6$-alkoxy, ($C_1$-$C_6$-alkylthio)carbonyl-$C_1$-$C_6$-haloalkoxy, ($C_1$-$C_6$-haloalkylthio)carbonyl-$C_1$-$C_6$-haloalkoxy, ($C_1$-$C_6$-alkylthio-$C_1$-$C_6$-alkyl)carbonyl-$C_1$-$C_6$-alkoxy, ($C_1$-$C_6$-haloalkylthio-$C_1$-$C_6$-alkyl)carbonyl-$C_1$-$C_6$-alkoxy, ($C_1$-$C_6$-alkylthio-$C_1$-$C_6$-haloalkyl)carbonyl-$C_1$-$C_6$-alkoxy, ($C_1$-$C_6$-alkylthio-$C_1$-$C_6$-alkyl)carbonyl-$C_1$-$C_6$-haloalkoxy, ($C_1$-$C_6$-haloalkylthio-$C_1$-$C_6$-haloalkyl)carbonyl-$C_1$-$C_6$-alkoxy, ($C_1$-$C_6$-haloalkylthio-$C_1$-$C_6$-alkyl)carbonyl-$C_1$-$C_6$-haloalkoxy, ($C_1$-$C_6$-alkylthio-$C_1$-$C_6$-haloalkyl)carbonyl-$C_1$-$C_6$-haloalkoxy, ($C_1$-$C_6$-haloalkylthio-$C_1$-$C_6$-haloalkyl)carbonyl-$C_1$-$C_6$-haloalkoxy, $C_3$-$C_6$-cycloalkoxy, ($C_3$-$C_6$-cycloalkyl)$C_1$-$C_6$-alkoxy, ($C_3$-$C_6$-cycloalkyl)$C_1$-$C_6$-haloalkoxy, aminocarbonyl-$C_1$-$C_6$-alkoxy, aminocarbonyl-$C_1$-$C_6$-haloalkoxy, N—($C_1$-$C_6$-alkyl)-aminocarbonyl-$C_1$-$C_6$-alkoxy, N—($C_1$-$C_6$-alkyl)-aminocarbonyl-$C_1$-$C_6$-haloalkoxy, N, N-di($C_1$-$C_6$-alkyl)-aminocarbonyl-$C_1$-$C_6$-alkoxy, N, N-di($C_1$-$C_6$-alkyl)-aminocarbonyl-$C_1$-$C_6$-haloalkoxy, O—N=C(di(phenyl), O—N=C(phenyl)($C_1$-$C_6$-alkyl), O—N=C[di($C_1$-$C_6$-alkyl)], ($C_1$-$C_6$-alkyl)$_3$-silyl-$C_1$-$C_6$-alkoxy, $C_1$-$C_6$-alkylthio, $C_1$-$C_6$-haloalkylthio, $C_1$-$C_6$-alkoxy-$C_1$-$C_6$-alkylthio, $C_1$-$C_6$-haloalkoxy-$C_1$-$C_6$-alkylthio, $C_1$-$C_6$-alkoxy-$C_1$-$C_6$-haloalkylthio, $C_1$-$C_6$-haloalkoxy-$C_1$-$C_6$-haloalkylthio, $C_1$-$C_6$-alkoxy-$C_1$-$C_6$-alkoxy-$C_1$-$C_6$-alkylthio, $C_1$-$C_6$-cyanoalkylthio, $C_2$-$C_6$-alkenylthio, $C_2$-$C_6$-haloalkenylthio, $C_2$-$C_6$-alkenyloxy-$C_1$-$C_6$-alkylthio, $C_2$-$C_6$-haloalkenyloxy-$C_1$-$C_6$-alkylthio, $C_2$-$C_6$-alkenyloxy-$C_1$-$C_6$-haloalkylthio, $C_2$-$C_6$-haloalkenyloxy-$C_1$-$C_6$-haloalkylthio, $C_1$-$C_6$-alkynylthio, $C_2$-$C_6$-haloalkynylthio, $C_2$-$C_6$-alkynyloxy-$C_1$-$C_6$-alkylthio, $C_2$-$C_6$-haloalkynyloxy-$C_1$-$C_6$-haloalkylthio, $C_2$-$C_6$-alkynyloxy-$C_1$-$C_6$-haloalkylthio, $C_2$-$C_6$-alkynyloxy-$C_2$-$C_6$-alkenylthio, $C_2$-$C_6$-haloalkynyloxy-$C_2$-$C_6$-alkenylthio, $C_2$-$C_6$-alkynyloxy-$C_2$-$C_6$-haloalkenylthio, $C_2$-$C_6$-haloalkynyloxy-$C_2$-$C_6$-haloalkenylthio, $C_2$-$C_6$-alkynyloxy-$C_2$-$C_6$-alkynylthio, $C_2$-$C_6$-haloalkynyloxy-$C_2$-$C_6$-alkynylthio, $C_2$-$C_6$-alkynyloxy-$C_2$-$C_6$-haloalkynylthio, $C_2$-$C_6$-haloalkynyloxy-$C_2$-$C_6$-haloalkynylthio, ($C_1$-$C_6$-alkyl)carbonyl-$C_1$-$C_6$-alkylthio, ($C_1$-$C_6$-haloalkyl)carbonyl-$C_1$-$C_6$-alkylthio, ($C_1$-$C_6$-alkyl)carbonyl-$C_1$-$C_6$-haloalkylthio, ($C_1$-$C_6$-haloalkyl)carbonyl-$C_1$-$C_6$-haloalkylthio, ($C_1$-$C_6$-alkoxy)carbonyl-$C_1$-$C_6$-alkylthio, ($C_1$-$C_6$-haloalkoxy)carbonyl-$C_1$-$C_6$-alkylthio, ($C_1$-$C_6$-alkoxy)carbonyl-$C_1$-$C_6$-haloalkylthio, ($C_1$-$C_6$-haloalkoxy)carbonyl-$C_1$-$C_6$-haloalkylthio, ($C_1$-$C_6$-alkoxy-$C_1$-$C_6$-alkyl)carbonyl-$C_1$-$C_6$-alkylthio, ($C_1$-$C_6$-haloalkoxy-$C_1$-$C_6$-alkyl)carbonyl-$C_1$-$C_6$-alkylthio, ($C_1$-$C_6$-alkoxy-$C_1$-$C_6$-haloalkyl)carbonyl-$C_1$-$C_6$-alkylthio, ($C_1$-$C_6$-alkoxy-$C_1$-$C_6$-alkyl)carbonyl-$C_1$-$C_6$-haloalkylthio, ($C_1$-$C_6$-haloalkoxy-$C_1$-$C_6$-haloalkyl)carbonyl-$C_1$-$C_6$-alkylthio, ($C_1$-$C_6$-haloalkoxy-$C_1$-$C_6$-alkyl)carbonyl-$C_1$-$C_6$-haloalkylthio, ($C_1$-$C_6$-alkoxy-$C_1$-$C_6$-haloalkyl)carbonyl-$C_1$-$C_6$-haloalkylthio, ($C_1$-$C_6$-haloalkoxy-$C_1$-$C_6$-haloalkyl)carbonyl-$C_1$-$C_6$-haloalkylthio, ($C_1$-$C_6$- alkylthio)carbonyl-$C_1$-$C_6$-alkylthio, ($C_1$-$C_6$-haloalkylthio)carbonyl-$C_1$-$C_6$-alkylthio, ($C_1$-$C_6$-alkylthio)carbonyl-$C_1$-$C_6$-haloalkylthio, ($C_1$-$C_6$-haloalkylthio)carbonyl-$C_1$-$C_6$-haloalkylthio, ($C_1$-$C_6$-alkylthio-$C_1$-$C_6$-alkyl)carbonyl-$C_1$-$C_6$-alkylthio, ($C_1$-$C_6$-haloalkylthio-$C_1$-$C_6$-alkyl)carbonyl-$C_1$-$C_6$-alkylthio, ($C_1$-$C_6$-alkylthio-$C_1$-$C_6$-haloalkyl)carbonyl-$C_1$-$C_6$-alkylthio, ($C_1$-$C_6$-alkylthio-$C_1$-$C_6$-alkyl)carbonyl-$C_1$-$C_6$-haloalkylthio, ($C_1$-$C_6$-haloalkylthio-$C_1$-$C_6$-haloalkyl)carbonyl-$C_1$-$C_6$-alkylthio, ($C_1$-$C_6$-haloalkylthio-$C_1$-$C_6$-alkyl)carbonyl-$C_1$-$C_6$-haloalkylthio, ($C_1$-$C_6$-alkylthio-$C_1$-$C_6$-haloalkyl)carbonyl-$C_1$-$C_6$-haloalkylthio, ($C_1$-$C_6$-haloalkylthio-$C_1$-$C_6$-haloalkyl)carbonyl-$C_1$-$C_6$-haloalkylthio, $C_3$-$C_6$-cycloalkylthio, ($C_3$-$C_6$-cycloalkyl)$C_1$-$C_6$-alkylthio, ($C_3$-$C_6$-cycloalkyl)$C_1$-$C_6$-haloalkylthio, aminocarbonyl-$C_1$-$C_6$-alkylthio, aminocarbonyl-$C_1$-$C_6$-haloalkylthio, N—($C_1$-$C_6$-alkyl)-aminocarbonyl-$C_1$-$C_6$-alkylthio, N—($C_1$-$C_6$-haloalkyl)-aminocarbonyl-$C_1$-$C_6$-alkylthio, N—($C_1$-$C_6$-alkyl)-aminocarbonyl-$C_1$-$C_6$-haloalkylthio, N—($C_1$-$C_6$-haloalkyl)-aminocarbonyl-$C_1$-$C_6$-haloalkylthio, N,N-di($C_1$-$C_6$-alkyl)-aminocarbonyl-$C_1$-$C_6$-alkylthio, N,N-di($C_1$-$C_6$-haloalkyl)-aminocarbonyl-$C_1$-$C_6$-alkylthio, N,N-di($C_1$-$C_6$-alkyl)aminocarbonyl-$C_1$-$C_6$-haloalkylthio, N,N-di($C_1$-$C_6$-haloalkyl)-aminocarbonyl-$C_1$-$C_6$-haloalkylthio, $NH_2$, ($C_1$-$C_6$-alkyl)amino, hydroxyamino, ($C_1$-$C_6$-alkoxy)amino, ($C_3$-$C_6$-cycloalkoxy)amino, ($C_1$-$C_6$-alkyl)sulfinylamino, ($C_1$-$C_6$-alkyl)sulfonylamino, (amino)sulfinylamino, [($C_1$-$C_6$-alkyl)amino]sulfinylamino, (amino)sulfonylamino, [($C_1$-$C_6$-alkyl)amino]sulfonylamino, [di($C_1$-$C_6$-alkyl)amino]sulfonylamino, di($C_1$-$C_6$-alkyl)amino, (hydroxy)($C_1$-$C_6$-alkyl)amino, (hydroxy)($C_1$-$C_6$-cycloalkyl)amino, ($C_1$-$C_6$-alkoxy)($C_1$-$C_6$-alkyl)amino, ($C_1$-$C_6$-alkoxy)($C_3$-$C_6$-cycloalkyl)amino, ($C_3$-$C_6$-cycloalkoxy)($C_1$-$C_6$-alkyl)amino, ($C_3$-$C_6$-cycloalkoxy)($C_3$-$C_6$-cycloalkyl)amino, [($C_1$-$C_6$-alkyl)sulfinyl]($C_1$-$C_6$-alkyl)amino, [($C_1$-$C_6$-alkyl)sulfonyl]($C_1$-$C_6$-alkyl)amino, [di($C_1$-$C_6$-alkyl)amino]sulfinylamino, [di($C_1$-$C_6$-alkyl)amino]sulfonylamino, phenyloxy, phenyl-$C_1$-$C_6$-alkoxy, phenylthio, phenyl-$C_1$-$C_6$-alkylthio, phenylamino, ($C_1$-$C_6$-alkyl)(phenyl)amino, (heteroaryl)oxy, heteroaryl-$C_1$-$C_6$-alkoxy, (heterocyclyl)oxy, heterocyclyl-$C_1$-$C_6$-alkoxy, wherein the phenyl, heteroaryl and heterocyclyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

provided that in case $R^2$ is OH, $R^1$ is not $C_1$-$C_6$-alkyl, hydroxy-$C_1$-$C_6$-alkyl, $C_1$-$C_6$-alkoxy or $C_1$-$C_6$-alkylthio.

Also preferred are the pyrimidines of formula (II), wherein $R^1$ is $C_1$-$C_6$-alkyl, $C_1$-$C_6$-alkoxy, $C_1$-$C_6$-haloalkoxy, $C_2$-$C_6$-alkenyloxy, $C_2$-$C_6$-haloalkenyloxy $C_2$-$C_6$-alkinyloxy, $C_2$-$C_6$-haloalkinyloxy, $C_1$-$C_6$-alkylthio, $C_3$-$C_6$-cycloalkyl or phenyl,
wherein the cycloalkyl or phenyl substituent is unsubstituted;
particularly preferred $C_1$-$C_6$-alkyl, $C_1$-$C_6$-alkoxy or $C_3$-$C_6$-cycloalkyl,
wherein the cycloalkyl substituent is unsubstituted;
especially preferred $C_3$-$C_6$-cycloalkyl,
wherein the cycloalkyl substituent is unsubstituted;
also especially preferred $C_2H_5$, i-$C_3H_7$, i-$C_4H_9$, $OCH_3$, c-$C_3H_5$ or c-$C_4H_9$; more preferred $C_2H_5$, $OCH_3$ or c-$C_3H_5$;
most preferred c-$C_3H_5$.

Also preferred are the pyrimidines of formula (II), wherein
$R^1$ is $C_1$-$C_6$-alkyl, $C_1$-$C_6$-alkoxy, $C_1$-$C_6$-haloalkoxy, $C_1$-$C_6$-alkylthio, $C_3$-$C_6$-cycloalkyl or phenyl,
wherein the cycloalkyl or phenyl substituent is unsubstituted;
particularly preferred $C_1$-$C_6$-alkyl, $C_1$-$C_6$-alkoxy or $C_3$-$C_6$-cycloalkyl,
wherein the cycloalkyl substituent is unsubstituted;
especially preferred $C_3$-$C_6$-cycloalkyl,
wherein the cycloalkyl substituent is unsubstituted;
also especially preferred $C_2H_5$, i-$C_3H_7$, i-$C_4H_9$, $OCH_3$, c-$C_3H_5$ or c-$C_4H_9$;
more preferred $C_2H_5$, $OCH_3$ or c-$C_3H_5$;
most preferred c-$C_3H_5$.

Also preferred are the pyrimidines of formula (II), wherein
$R^2$ is OH, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, ($C_1$-$C_6$-alkoxy)carbonyl-$C_1$-$C_6$-alkoxy, $C_1$-$C_6$-alkylthio, ($C_1$-$C_6$-alkoxy)carbonyl-$C_1$-$C_6$-alkylthio, $NH_2$, ($C_1$-$C_6$-alkyl)amino, ($C_1$-$C_6$-alkyl)sulfonylamino, [di($C_1$-$C_6$-alkyl)amino]sulfonylamino, phenyloxy, phenyl-$C_1$-$C_6$-alkoxy or phenyl-$C_1$-$C_6$-alkylthio,
wherein the phenyl substituent is unsubstituted;
preferably OH, $C_1$-$C_6$-alkoxy, $C_1$-$C_6$-haloalkoxy, $C_2$-$C_6$-alkynyloxy, ($C_1$-$C_6$-alkoxy)carbonyl-$C_1$-$C_6$-alkoxy, $C_1$-$C_6$-alkylthio, ($C_1$-$C_6$-alkoxy)carbonyl-$C_1$-$C_6$-alkylthio, $NH_2$, ($C_1$-$C_6$-alkyl)amino, ($C_1$-$C_6$-alkyl)sulfonylamino, [di($C_1$-$C_6$-alkyl)amino]sulfonylamino, phenyloxy, phenyl-$C_1$-$C_6$-alkoxy or phenyl-$C_1$-$C_6$-alkylthio,
wherein the phenyl substituent is unsubstituted;
particularly preferred OH, $C_1$-$C_6$-alkoxy, $C_1$-$C_6$-haloalkoxy, $C_2$-$C_6$-alkynyloxy, $C_1$-$C_6$-alkylthio, phenyloxy or phenyl-$C_1$-$C_6$-alkoxy,
wherein the phenyl substituent is unsubstituted;
also particularly preferred OH, $C_1$-$C_6$-alkoxy, $C_2$-$C_6$-alkynyloxy or $C_1$-$C_6$-haloalkoxy;
especially preferred $C_1$-$C_6$-alkoxy, $C_2$-$C_6$-alkynyloxy or $C_1$-$C_6$-haloalkoxy;
also especially preferred OH, $C_1$-$C_6$-alkoxy or $C_1$-$C_6$-haloalkoxy;
more preferred OH or $C_1$-$C_6$-alkoxy,
most preferred OH,
also most preferred $C_1$-$C_6$-alkoxy.

Also preferred are pyrimidines of formula (II), wherein
$R^1$ is $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_6$-cycloalkyl,
wherein the cycloalkyl is unsubstituted or substituted by one to five substituents selected from halogen;
preferably $C_1$-$C_6$-alkyl, $C_1$-$C_6$-alkoxy or $C_3$-$C_6$-cycloalkyl;
particularly preferred $C_3$-$C_6$-cycloalkyl or $C_1$-$C_6$-alkoxy;
especially preferred $C_3$-$C_6$-cycloalkyl,
more preferably cyclopropyl.

Also preferred are pyrimidines of formula (II), wherein
$R^2$ is OH, halogen, $C_1$-$C_6$-alkoxy, $C_1$-$C_6$-haloalkoxy or $C_3$-$C_6$-cycloalkoxy;
preferably OH, halogen or $C_1$-$C_6$-alkoxy;
particularly preferred OH or $C_1$-$C_6$-alkoxy;

more preferably OH.

Preferred are pyrimidines of formula (II), wherein
$R^1$ is $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_6$-cycloalkyl,
wherein the cycloalkyl is unsubstituted or substituted by one to five substituents selected from halogen;
preferably $C_1$-$C_6$-alkyl, $C_1$-$C_6$-alkoxy or $C_3$-$C_6$-cycloalkyl;
particularly preferred $C_3$-$C_6$-cycloalkyl or $C_1$-$C_6$-alkoxy;
especially preferred $C_3$-$C_6$-cycloalkyl,
more preferably cyclopropyl;
and
$R^2$ is OH, halogen, $C_1$-$C_6$-alkoxy, $C_1$-$C_6$-haloalkoxy or $C_3$-$C_6$-cycloalkoxy;
preferably OH, halogen or $C_1$-$C_6$-alkoxy;
particularly preferred OH or $C_1$-$C_6$-alkoxy;
more preferably OH.

With respect to the variables, the particularly preferred embodiments of the intermediate pyrimidines (II) correspond, either independently of one another or in combination with one another, to those of the variables of $R^1$ and $R^2$ of the phenylpyrimidines formula (I).

Particular preference is given to pyrimidines of formula (II.a) (corresponds to pyrimidines of formula (II) wherein $R^2$ is OH:

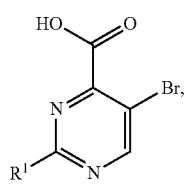

(II.a)

wherein the variable $R^1$ has the meanings, in particular the preferred meanings, as defined above.

Special preference is given to the pyrimidines of the formulae (II.a.1) to (II.a.4) of Table (II):

TABLE (II)

| No. | $R^1$ |
|---|---|
| II.a.1 | c-$C_3H_5$ |
| II.a.2 | c-$C_4H_7$ |
| II.a.3 | $C_2H_5$ |
| II.a.4 | $OCH_3$ |

Also preferred are the pyrimidines of formula (II.b), particularly preferred the pyrimidines of formulae (II.b.1) to (II.b.4), which differ from the corresponding pyrimidines of formula (II.a) as well as formulae (II.a.1) to (II.a.4) only in that $R^2$ is $OCH_3$:

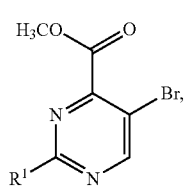

(II.b)

Also preferred are the pyrimidines of formula (II.c), particularly preferred the pyrimidines of formulae (II.c.1) to (II.c.4), which differ from the corresponding pyrimidines of formula (II.a) as well as formulae (II.a.1) to (II.a.4) only in that $R^2$ is $OC_2H_5$:

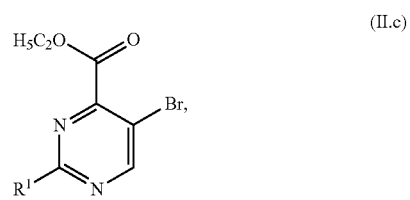

(II.c)

Also preferred are the pyrimidines of formula (II.d), particularly preferred the pyrimidines of formulae (II.d.1) to (II.d.4), which differ from the corresponding pyrimidines of formula (II.a) as well as formulae (II.a.1) to (II.a.4) only in that $R^2$ is $OCH_2C\equiv CH$:

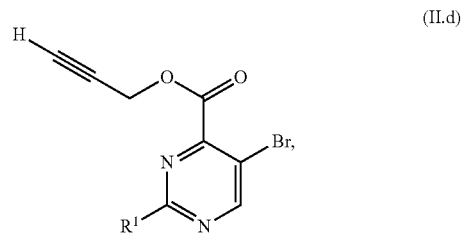

(II.d)

Also preferred are the pyrimidines of formula (II.e), particularly preferred the pyrimidines of formulae (II.e.1) to (II.e.4), which differ from the corresponding pyrimidines of formula (II.a) as well as formulae (II.a.1) to (II.a.4) only in that $R^2$ is $OCH_2CHF_2$:

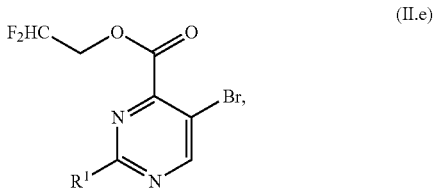

(II.e)

To widen the spectrum of action and to achieve synergistic effects, the phenylpyrimidines of formula (I) may be mixed with a large number of representatives of other herbicidal or growth-regulating active ingredient groups and then applied concomitantly. Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

It may furthermore be beneficial to apply the phenylpyrimidines of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

The invention also relates to agrochemical compositions comprising at least an auxiliary and at least one phenylpyrimidine of formula (I) according to the invention.

An agrochemical composition comprises a pesticidal effective amount of a phenylpyrimidine of formula (I). The term "effective amount" denotes an amount of the composition or of the compounds I, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific phenylpyrimidine of formula (I) used.

The phenylpyrimidines of formula (I), their N-oxides, salts or derivatives can be converted into customary types of agrochemical compositions, e.g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, $6^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the phenylpyrimidines of formula (I) on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-Soluble Concentrates (SL, LS)

10-60 wt % of a phenylpyrimidine of formula (I) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a phenylpyrimidine of formula (I) according to the invention and 1-10 wt % dispersant (e.g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a phenylpyrimidine of formula (I) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a phenylpyrimidine of formula (I) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a phenylpyrimidine of formula (I) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a phenylpyrimidine of formula (I) according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a phenylpyrimidine of formula (I) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a phenylpyrimidine of formula (I) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a phenylpyrimidine of formula (I) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a phenylpyrimidine of formula (I) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a phenylpyrimidine of formula (I) according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % of a phenylpyrimidine of formula (I) according to the invention are ground finely and mixed intimately with solid carrier (e.g. finely divided kaolin) ad 100 wt %.

x) Granules (GR, FG)

0.5-30 wt % of a phenylpyrimidine of formula (I) according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of a phenylpyrimidine of formula (I) according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions comprising generally comprise between 0.01 and 95%, preferably between 0.1 and 90%, and in particular between 0.5 and 75%, by weight of the phenylpyrimidine of formula (I). The phenylpyrimidines of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The agrochemical compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying phenylpyrimidines of formula (I) and agrochemical compositions thereof, on to plant propagation material, especially seeds, include dressing, coating, pelleting, dusting, soaking and in-furrow application methods of the propagation material. Preferably, phenylpyrimidines of formula (I) and agrochemical compositions thereof, are applied on to the plant propagation material by a method such that germination is not induced, e.g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the phenylpyrimidines of formula (I) and the agrochemical compositions comprising them as premix or, if appropriate not until immediately prior to use (tank mix). These agents can be admixed with the agrochemical compositions according to the invention in a weight ratio of 1:100 to 100:1, preferably 1:10 to 10:1.

The user applies the phenylpyrimidine of formula (I) according to the invention and the agrochemical compositions comprising them usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e.g. components comprising phenylpyrimidines of formula (I) may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e.g components comprising phenylpyrimidines of formula (I) can be applied jointly (e.g. after tank mix) or consecutively.

The phenylpyrimidines of formula (I), are suitable as herbicides. They are suitable as such or as an appropriately formulated composition (agrochemical composition).

The phenylpyrimidines of formula (I), or the agrochemical compositions comprising the phenylpyrimidines of formula (I), control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

The phenylpyrimidines of formula (I), or the agrochemical compositions comprising them, are applied to the plants mainly by spraying the leaves. Here, the application can be carried out using, for example, water as carrier by customary spraying techniques using spray liquor amounts of from about 100 to 1000 l/ha (for example from 300 to 400 l/ha). The phenylpyrimidines of formula (I), or the agrochemical compositions comprising them, may also be applied by the low-volume or the ultra-low-volume method, or in the form of micro granules.

Application of the phenylpyrimidines of formula (I), or the agrochemical compositions comprising them, can be done before, during and/or after, preferably during and/or after, the emergence of the undesirable plants.

The phenylpyrimidines of formula (I), or the agrochemical compositions comprising them, can be applied pre-, post-emergence or pre-plant, or together with the seed of a crop plant. It is also possible to apply the phenylpyrimidines of formula (I), or the agrochemical compositions comprising them, by applying seed, pretreated with the phenylpyrimidines of formula (I), or the agrochemical compositions comprising them, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the phenylpyrimidines of formula (I), or the agrochemical compositions comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the phenylpyrimidines of formula (I), or the agrochemical compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

When employed in plant protection, the amounts of active substances applied, i.e. the phenylpyrimidines of formula (I) without formulation auxiliaries, are, depending on the kind of effect desired, from 0.001 to 2 kg per ha, preferably from 0.005 to 2 kg per ha, more preferably from 0.05 to 0.9 kg per ha and in particular from 0.1 to 0.75 kg per ha.

In another embodiment of the invention, the application rate of the phenylpyrimidines of formula (I) is from 0.001 to 3 kg/ha, preferably from 0.005 to 2.5 kg/ha and in particular from 0.01 to 2 kg/ha of active substance (a.s.).

In another preferred embodiment of the invention, the rates of application of the phenylpyrimidines of formula (I) according to the present invention (total amount of phenylpyrimidines of formula (I)) are from 0.1 g/ha to 3000 g/ha, preferably 10 g/ha to 1000 g/ha, depending on the control target, the season, the target plants and the growth stage.

In another preferred embodiment of the invention, the application rates of the phenylpyrimidines of formula (I) are in the range from 0.1 g/ha to 5000 g/ha and preferably in the range from 1 g/ha to 2500 g/ha or from 5 g/ha to 2000 g/ha.

In another preferred embodiment of the invention, the application rate of the phenylpyrimidines of formula (I) is 0.1 to 1000 g/ha, preferably 1 to 750 g/ha, more preferably 5 to 500 g/ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. the phenylpyrimidines of formula (I) are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Depending on the application method in question, the phenylpyrimidines of formula (I), or the agrochemical compositions comprising them, can additionally be employed in a further number of crop plants for eliminating undesirable plants. Examples of suitable crops are the following: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec.*, Manihot esculenta, Medicago sativa, Musa* spec.*, Nicotiana tabacum (N. rustica), Olea europaea, Oryza sativa, Phaseolus lunatus, Phaseolus vulgaris, Picea abies, Pinus* spec.*, Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera* and *Zea mays*.

Preferred crops are *Arachis hypogaea, Beta vulgaris* spec. *altissima, Brassica napus* var. *napus, Brassica oleracea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus* spec.*, Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (s. vulgare), Triticale, Triticum aestivum, Triticum durum, Vicia faba, Vitis vinifera* and *Zea mays*.

Especially preferred crops are crops of cereals, corn, soybeans, rice, oilseed rape, cotton, potatoes, peanuts or permanent crops.

The phenylpyrimidines of formula (I) according to the invention, or the agrochemical compositions comprising them, can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e.g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e.g., Clearfield® summer rape (Canola, BASF SE, Germany) being tolerant to imidazolinones, e.g., imazamox, or ExpressSun® sunflowers (DuPont, USA) being tolerant to sulfonyl ureas, e.g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RounduppReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e.g., CryIA(b), CryIA(c), CryIF, CryIF(a2), CryIIA(b), CryIIIA, CryIIIB(b1) or Cry9c; vegetative insecticidal proteins (VIP), e.g., VIP1, VIP2, VIP3 or VIP3A; insecticidal proteins of bacteria colonizing nematodes, e.g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e.g., WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIPtoxin); NewLeaf® (potato cultivars producing the Cry3A toxin); Bt-Xtra®, NatureGard®, KnockOut®, BiteGard®, Protecta®, Bt11 (e.g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e.g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modi-fied plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e.g., oil crops that produce health-promoting long-chain omega-3 fatty acids or unsaturated omega-9 fatty acids (e.g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

The preparation of the phenylpyrimidines of formula (I) is illustrated by examples; however, the subject matter of the present invention is not limited to the examples given.

A PREPARATION EXAMPLES

Example 1: Methyl-5-(2-chlorophenyl)-2-cyclobutyl-pyrimidine-4-carboxylate

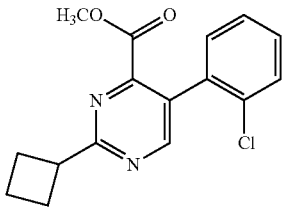 [SMILES: COC(=O)c1nc(C2CCC2)ncc1-c1ccccc1Cl]

1.1. 5-Bromo-2-cyclobutyl-pyrimidine-4-carboxylic acid

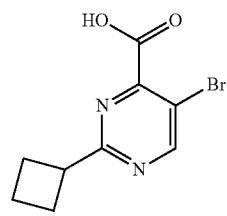 [SMILES: O=C(O)c1nc(C2CCC2)ncc1Br]

Ethanol (100 ml) is carefully added to NaH (95% purity, 1.01 g, 40.1 mmol, 2.70 eq) and kept in a flask at −70° C. under nitrogen. The resulting mixture is slowly warmed to ambient temperature and the cyclobutanecarboxamidine hydrochlorid (5.00 g, 37.2 mmol, 2.50 eq.) was added in portions. The mixture is warmed to 50° C. and maintained at this temperature for 1 h followed by the portion wise addition of mucobromic acid (3.83 g, 14.9 mmol, 1.00 eq.) while keeping the temperature around 50° C. The mixture is cooled to ambient temperature and allowed to stir for additional 16 h. All volatile components are removed under reduced pressure and the resulting residue is titrated with aq. HCl (2 mol/L). The solids are collected by filtration, washed with water and dried yielding the title compound (2.24 g, yield 59%) as a colorless solid.

MS (ESI) m/z 257.3 [M+H$^+$]

1.2 Methyl 5-bromo-2-cyclobutyl-pyrimidine-4-carboxylate

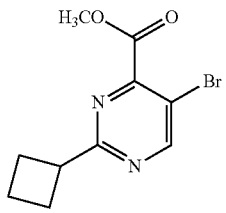 [SMILES: COC(=O)c1nc(C2CCC2)ncc1Br]

5-Bromo-2-cyclobutyl-pyrimidine-4-carboxylic acid (2.24 g, 8.69 mmol, 1.00 eq.) is dissolved in dichloromethane and a catalytic amount of DMF is added. Oxalylchloride (1.32 g, 985 µL, 10.4 mmol, 1.20 eq.) is added drop wise at ambient temperature and the resulting mixture is stirred for additional 6 h before being added in a drop wise manner to a solution of triethylamine (2.64 g, 3.62 mL, 26.1 mmol, 3.00 eq.) in MeOH kept at 0° C. After completion of the addition the reaction is stirred for additional 16 h before ice water is added. The phases are separated and the aqueous phase is extracted with dichloromethane. The combined organics are dried over Na$_2$SO$_4$, the drying agent is removed via filtration and all volatiles are removed under reduced pressure. Column chromatography of the resulting crude product (ISCO-CombiFlash Rf, reverse phase, H$_2$O/MeCN) yields the title compound (1.48 g, yield 63%) as a colorless solid.

MS (ESI) m/z 271.3 [M+H$^+$]

1.3 Methyl 5-(2-chlorophenyl)-2-cyclobutyl-pyrimidine-4-carboxylate

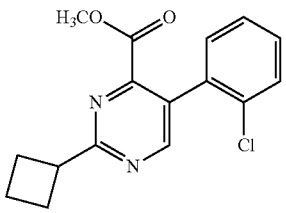 [SMILES: COC(=O)c1nc(C2CCC2)ncc1-c1ccccc1Cl]

A mixture of methyl 5-bromo-2-cyclobutyl-pyrimidine-4-carboxylate (850 mg, 3.14 mmol, 1.00 eq.), 2-chlorophenylboronic acid (490 mg, 3.14 mmol, 1.00 eq.), K$_2$CO$_3$ (867 mg, 6.27 mmol, 2.00 eq.) and PdCl$_2$dppf (256 mg, 0.31 mmol, 0.10 eq.) is dissolved in a mixture of degassed acetonitrile (5 mL) and degassed water (1 mL) under nitrogen. The resulting mixture is heated to 90° C. for 20 h and then cooled to ambient temperature. Water and dichloromethan are added, the phases are separated and organic phase is dried over Na$_2$SO$_4$. The solids are removed via filtration and resulting solution is concentrated under reduced pressure. Column chromatography of the crude product (ISCO-CombiFlash Rf, reverse phase, H$_2$O/MeCN) yields the title compound (622 mg, yield 66%) as a colorless solid.

MS (ESI) m/z 302.8 [M+H$^+$]

Example 2: 5-(2-Chlorophenyl)-2-cyclobutyl-pyrimidine-4-carboxylate

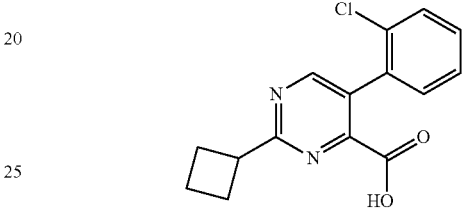

Methyl-5-(2-chlorophenyl)-2-cyclobutyl-pyrimidine-4-carboxylate (350 mg, 1.16 mmol, 1.00 eq.) is dissolved in THF and lithiumhydroxid (55.4 mg, 2.31 mmol, 2.00 eq.) is added as a solution in water. The resulting mixture is stirred for 18 hours at ambient temperature and then acidified to pH=2 with aqueous hydrochloric acid (2 mol/L). The precipitate is filtered and dried yielding the title compound (320 mg, 96%) as a colorless solid.

MS (ESI) m/z 289.4 [M+H$^+$]

$^1$H NMR (400 MHz, DMSO-d$_6$): δ=13.7 (brs, 1H), 8.85 (s, 1H), 7.59-7.52 (m, 1H), 7.49-7.40 (m, 3H), 3.90-3.82 (m, 1H), 2.46-2.32 (m, 4H), 2.13-2.01 (m 1H), 1.95-1.86 (m, 1H) ppm.

Example 3: Methyl 2-[5-(2-chlorophenyl)-2-cyclopropyl-pyrimidine-4-carbonyl]sulfanyl-acetate

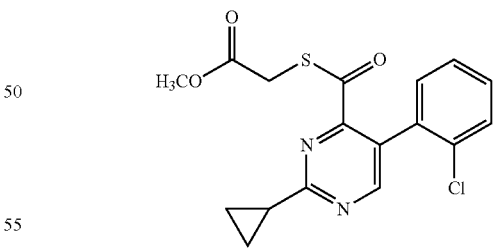

5-(2-Chlorophenyl)-2-cyclopropyl-pyrimidine-4-carboxylic acid (prepared analogously as described in example 1, 500 mg, 1.82 mmol, 1.00 eq.) is dissolved in dichloromethane and a catalytic amount of DMF is added. Oxalylchloride (277 mg, 166 µL, 2.55 mmol, 1.20 eq.) is added drop wise at ambient temperature and the resulting mixture is stirred for additional 4 h before being added in a drop wise manner to a solution of triethylamine (553 mg, 757 µL, 5.46 mmol, 3.00 eq.) and methyl 2-sulfanylacetate (270 mg, 228 µL, 2.55 mmol, 1.40 eq.) in dichloromethane kept at 0° C. After completion of the addition the reaction is stirred for additional 17 h before ice water is added. The phases are separated and the aqueous phase is extracted with dichloromethane. The combined organics are dried over $Na_2SO_4$, the drying agent is removed via filtration and all volatiles are removed under reduced pressure. Column chromatography of the resulting crude product (ISCO-CombiFlash Rf, reverse phase, $H_2O$/MeCN) yields the title compound (617 mg, 93%) as a colorless solid.

MS (ESI) m/z 362.7 [M+H$^+$]

$^1$H NMR (400 MHz, DMSO-$d_6$): δ=8.79 (s, 1H), 7.55-7.53 (m, 1H), 7.48-7.39 (m, 3H), 3.78 (d, J=2.1 Hz, 2H), 3.60 (s, 3H), 2.43-2.35 (m, 1H), 1.25-1.22 (m, 2H), 1.17-1.14 (m, 2H) ppm.

The compounds listed below in table 1 can be prepared similarly to the examples mentioned above

TABLE 1

(I)

| Ex. | R$^1$ | R$^2$ | R$^3$ | R$^4$ | R$^5$ | R$^6$ | R$^7$ | R$_t$ [min] | m/z |
|---|---|---|---|---|---|---|---|---|---|
| 4 | CH$_3$ | OH | CH$_3$ | H | H | H | H | 0.791 | 229.0 |
| 5 | CH$_3$ | OCH$_3$ | CH$_3$ | H | H | H | H | 0.982 | 243.4 |
| 6 | C$_2$H$_5$ | OH | Cl | H | H | H | H | 0.909 | 263.1 |
| 7 | C$_2$H$_5$ | OH | Cl | H | H | CH$_3$ | H | 0.978 | 276.7 |
| 8 | C$_2$H$_5$ | OH | CH$_3$ | H | H | CH$_3$ | H | 0.917 | 243.1 |
| 9 | C$_2$H$_5$ | OH | CH$_3$ | H | H | CH$_3$ | H | 0.994 | 257.1 |
| 10 | C$_2$H$_5$ | OH | CH$_3$ | H | H | F | H | 0.919 | 260.8 |
| 11 | C$_2$H$_5$ | OH | CH$_3$ | H | H | Cl | H | 0.991 | 276.8 |
| 12 | C$_2$H$_5$ | OH | CH$_3$ | H | F | CH$_3$ | H | 0.998 | 275.1 |
| 13 | C$_2$H$_5$ | OH | CH$_3$ | H | CN | H | H | 0.867 | 268.1 |
| 14 | C$_2$H$_5$ | OH | CH$_3$ | H | CH$_3$ | H | H | 0.968 | 256.8 |
| 15 | C$_2$H$_5$ | OH | CH$_3$ | H | CF$_3$ | H | H | 1.080 | 311.6 |
| 16 | C$_2$H$_5$ | OH | OCH$_3$ | H | H | H | H | 0.834 | 259.2 |
| 17 | C$_2$H$_5$ | OH | OCH$_3$ | H | H | t-C$_4$H$_9$ | H | 1.097 | 315.1 |
| 18 | C$_2$H$_5$ | OH | OCH$_3$ | H | H | OCH$_3$ | H | 0.861 | 289.1 |
| 19 | C$_2$H$_5$ | OCH$_3$ | Cl | H | H | H | H | 1.070 | 276.8 |
| 20 | C$_2$H$_5$ | OCH$_3$ | Cl | H | H | CH$_3$ | H | 1.174 | 291.5 |
| 21 | C$_2$H$_5$ | OCH$_3$ | CH$_3$ | H | H | F | H | 1.091 | 274.8 |
| 22 | C$_2$H$_5$ | OCH$_3$ | CH$_3$ | H | H | Cl | H | 1.158 | 290.8 |
| 23 | C$_2$H$_5$ | OCH$_3$ | CH$_3$ | H | H | CH$_3$ | H | 1.146 | 270.1 |
| 24 | C$_2$H$_5$ | OCH$_3$ | CH$_3$ | H | CH$_3$ | H | H | 1.149 | 270.8 |
| 25 | C$_2$H$_5$ | OCH$_3$ | CH$_3$ | H | CF$_3$ | H | H | 1.230 | 325.5 |
| 26 | C$_2$H$_5$ | OC$_2$H$_5$ | Cl | H | H | H | H | 1.158 | 291.5 |
| 27 | C$_2$H$_5$ | OC$_2$H$_5$ | CH$_3$ | H | F | CH$_3$ | H | 1.222 | 303.1 |
| 28 | C$_2$H$_5$ | OC$_2$H$_5$ | OCH$_3$ | H | H | t-C$_4$H$_9$ | H | 1.311 | 343.2 |
| 29 | C$_2$H$_5$ | OC$_2$H$_5$ | OCH$_3$ | H | CN | H | H | 1.096 | 296.2 |
| 30 | n-C$_3$H$_7$ | OH | CH$_3$ | H | H | H | H | 0.987 | 257.1 |
| 31 | n-C$_3$H$_7$ | OCH$_3$ | CH$_3$ | H | H | H | H | 1.169 | 271.4 |
| 32 | i-C$_3$H$_7$ | OH | Cl | H | H | H | H | 1.045 | 276.7 |
| 33 | i-C$_3$H$_7$ | OH | CH$_3$ | H | H | H | H | 1.003 | 257.5 |
| 34 | i-C$_3$H$_7$ | OH | CH$_3$ | H | H | CH$_3$ | H | 1.078 | 271.5 |
| 35 | i-C$_3$H$_7$ | OH | OCH$_3$ | H | H | H | H | 0.977 | 272.8 |
| 36 | i-C$_3$H$_7$ | OCH$_3$ | Cl | H | H | H | H | 1.175 | 291.5 |
| 37 | i-C$_3$H$_7$ | OCH$_3$ | CH$_3$ | H | H | H | H | 1.193 | 271.5 |
| 38 | i-C$_3$H$_7$ | OCH$_3$ | CH$_3$ | H | H | CH$_3$ | H | 1.258 | 285.6 |
| 39 | i-C$_3$H$_7$ | OCH$_3$ | OCH$_3$ | H | H | H | H | 1.116 | 287.5 |
| 40 | i-C$_4$H$_9$ | OH | CH$_3$ | H | H | H | H | 1.061 | 270.8 |
| 41 | s-C$_4$H$_9$ | OH | CH$_3$ | H | H | H | H | 1.083 | 270.8 |
| 42 | t-C$_4$H$_9$ | OH | CH$_3$ | H | H | H | H | 1.158 | 271.5 |
| 43 | t-C$_4$H$_9$ | OH | CH$_3$ | H | H | CH$_3$ | H | 1.224 | 285.5 |
| 44 | t-C$_4$H$_9$ | OCH$_3$ | CH$_3$ | H | H | H | H | 1.333 | 285.6 |
| 45 | t-C$_4$H$_9$ | OCH$_3$ | CH$_3$ | H | H | CH$_3$ | H | 1.396 | 299.8 |
| 46 | CH$_2$OCH$_3$ | OH | CH$_3$ | H | H | H | H | 0.876 | 258.4 |
| 47 | CH$_2$OCH$_3$ | OCH$_3$ | CH$_3$ | H | H | H | H | 0.984 | 272.8 |
| 48 | CH(CH$_3$)(OCH$_3$) | OH | CH$_3$ | H | H | H | H | 0.868 | 273.1 |
| 49 | CH(CH$_3$)(OCH$_3$) | OCH$_3$ | Cl | H | H | H | H | 1.027 | 307.0 |
| 50 | CH(CH$_3$)(OCH$_3$) | OCH$_3$ | CH$_3$ | H | H | H | H | 1.029 | 287.4 |
| 51 | OCH$_3$ | OH | Cl | H | H | H | H | 0.873 | 265.0 |
| 52 | OCH$_3$ | OH | CH$_3$ | H | H | H | H | 0.856 | 245.1 |
| 53 | OCH$_3$ | OH | CH$_3$ | H | H | F | H | 0.894 | 263.4 |
| 54 | OCH$_3$ | OH | CH$_3$ | H | H | CH$_3$ | H | 0.937 | 259.2 |
| 55 | OCH$_3$ | OH | CH$_3$ | H | F | CH$_3$ | H | 0.968 | 277.1 |

TABLE 1-continued (I)

| Ex. | R¹ | R² | R³ | R⁴ | R⁵ | R⁶ | R⁷ | $R_t$ [min] | m/z |
|---|---|---|---|---|---|---|---|---|---|
| 56 | OCH₃ | OH | CH₃ | H | CN | H | H | 0.830 | 270.0 |
| 57 | OCH₃ | OH | CH₃ | H | CH₃ | H | H | 0.984 | 258.8 |
| 58 | OCH₃ | OH | OCH₃ | H | H | H | H | 0.801 | 261.1 |
| 59 | OCH₃ | OH | OCH₃ | H | H | OCH₃ | H | 0.815 | 291.1 |
| 60 | OCH₃ | OH | OCH₃ | H | H | t-C₄H₉ | H | 1.070 | 317.1 |
| 61 | OCH₃ | OCH₃ | Cl | H | H | H | H | 1.057 | 278.7 |
| 62 | OCH₃ | OCH₃ | CH₃ | H | H | F | H | 1.081 | 276.8 |
| 63 | OCH₃ | OCH₃ | CH₃ | H | CH₃ | H | H | 1.127 | 273.5 |
| 64 | OCH₃ | OC₂H₅ | CH₃ | H | F | CH₃ | H | 1.183 | 305.1 |
| 65 | OCH₃ | OC₂H₅ | CH₃ | H | CN | H | H | 1.059 | 298.2 |
| 66 | OCH₃ | OC₂H₅ | OCH₃ | H | H | t-C₄H₉ | H | 1.299 | 345.2 |
| 67 | OC₂H₅ | OH | CH₃ | H | H | H | H | 0.972 | 259.4 |
| 68 | OC₂H₅ | OH | CH₃ | H | H | CH₃ | H | 1.028 | 273.4 |
| 69 | OC₂H₅ | OC₂H₅ | CH₃ | H | H | H | H | 1.217 | 287.5 |
| 70 | OC₂H₅ | OC₂H₅ | CH₃ | H | H | CH₃ | H | 1.281 | 301.6 |
| 71 | O[CH(CH₃)₂] | OH | Cl | H | H | H | H | 1.056 | 297.7 |
| 72 | O[CH(CH₃)₂] | OH | CH₃ | H | H | H | H | 1.053 | 272.8 |
| 73 | O[CH(CH₃)₂] | OH | CH₃ | H | H | CH₃ | H | 1.100 | 286.8 |
| 74 | O[CH(CH₃)₂] | OH | OCH₃ | H | H | H | H | 0.983 | 288.8 |
| 75 | O[CH(CH₃)₂] | O-i-C₃H₇ | Cl | H | H | H | H | 1.305 | 334.7 |
| 76 | O[CH(CH₃)₂] | O-i-C₃H₇ | CH₃ | H | H | H | H | 1.318 | 314.8 |
| 77 | O[CH(CH₃)₂] | O-i-C₃H₇ | CH₃ | H | H | CH₃ | H | 1.371 | 329.0 |
| 78 | O[CH(CH₃)₂] | O-i-C₃H₇ | OCH₃ | H | H | H | H | 1.256 | 330.8 |
| 79 | OCH₂CF₃ | OH | CH₃ | H | H | H | H | 1.028 | 313.5 |
| 80 | OCH₂CF₃ | OH | CH₃ | H | H | CH₃ | H | 1.090 | 327.5 |
| 81 | OCH₂CF₃ | OCH₃ | CH₃ | H | H | H | H | 1.203 | 327.5 |
| 82 | OCH₂CF₃ | OCH₃ | CH₃ | H | H | CH₃ | H | 1.261 | 341.5 |
| 83 | SCH₃ | OH | F | H | H | OCH₃ | H | 0.989 | 295.0 |
| 84 | SCH₃ | OH | F | OCH₃ | Cl | H | H | 1.027 | 329.1 |
| 85 | SCH₃ | OH | Cl | H | H | Cl | H | 1.089 | 314.9 |
| 86 | SCH₃ | OH | Cl | H | H | CH₃ | H | 1.067 | 295.5 |
| 87 | SCH₃ | OH | Cl | H | H | CF₃ | H | 1.128 | 349.0 |
| 88 | SCH₃ | OH | Cl | H | H | OCH₃ | H | 1.038 | 311.0 |
| 89 | SCH₃ | OH | Cl | H | H | H | H | 1.104 | 314.9 |
| 90 | SCH₃ | OH | Cl | Cl | H | H | H | 1.082 | 314.9 |
| 91 | SCH₃ | OH | CH₃ | H | H | Cl | H | 1.090 | 295.0 |
| 92 | SCH₃ | OH | CH₃ | H | H | CH₃ | H | 1.075 | 275.1 |
| 93 | SCH₃ | OH | CH₃ | H | H | CF₃ | H | 1.119 | 329.1 |
| 94 | SCH₃ | OH | CH₃ | H | F | H | H | 1.022 | 279.0 |
| 95 | SCH₃ | OH | CH₃ | H | F | CH₃ | H | 1.058 | 293.1 |
| 96 | SCH₃ | OH | CH₃ | H | CN | H | H | 0.965 | 286.1 |
| 97 | SCH₃ | OH | CH₃ | H | CH₃ | H | H | 1.081 | 275.1 |
| 98 | SCH₃ | OH | CH₃ | H | CH₃ | CH₃ | H | 1.100 | 289.1 |
| 99 | SCH₃ | OH | CH₃ | H | CF₃ | H | H | 0.141 | 329.0 |
| 100 | SCH₃ | OH | CH₃ | H | OCH₃ | H | H | 1.014 | 291.1 |
| 101 | SCH₃ | OH | CH₃ | H | OC₂H₅ | CH₃ | H | 1.128 | 319.2 |
| 102 | SCH₃ | OH | CH₃ | CH₃ | H | H | H | 1.066 | 275.2 |
| 103 | SCH₃ | OH | i-C₃H₇ | H | H | H | H | 1.121 | 289.1 |
| 104 | SCH₃ | OH | OCH₃ | H | H | H | H | 0.949 | 277.0 |
| 105 | SCH₃ | OH | OCH₃ | H | H | t-C₄H₉ | H | 1.160 | 333.2 |
| 106 | SCH₃ | OH | OCH₃ | H | H | i-C₃H₇ | H | 1.110 | 319.1 |
| 107 | SCH₃ | OH | OCH₃ | H | H | CF₃ | H | 1.090 | 345.0 |
| 108 | SCH₃ | OH | OCH₃ | H | H | OCH₃ | H | 0.957 | 307.0 |
| 109 | SCH₃ | OH | OCH₃ | H | OCH₃ | H | H | 0.966 | 307.0 |
| 110 | SCH₃ | OH | OCH₃ | OCH₃ | H | H | OCH₃ | 0.934 | 337.1 |
| 111 | SCH₃ | OH | OCF₃ | H | H | OCH₃ | H | 1.077 | 361.1 |
| 112 | SCH₃ | OH | CO₂H | H | H | H | H | 0.815 | 291.0 |
| 113 | SCH₃ | OH | SC₂H₅ | H | H | H | H | 1.078 | 307.0 |
| 114 | SCH₃ | OH | S(O)₂CH₃ | H | H | H | H | 0.817 | 325.1 |
| 115 | SCH₃ | OH | O-(c-C₅H₉) | H | H | CH₃ | H | 1.195 | 345.1 |
| 116 | SCH₃ | OCH₃ | F | OCH₃ | Cl | H | H | 1.200 | 343.0 |
| 117 | SCH₃ | OCH₃ | Cl | H | H | CH₃ | H | 1.243 | 308.7 |
| 118 | SCH₃ | OCH₃ | CH₃ | H | F | CH₃ | H | 1.252 | 307.1 |
| 119 | SCH₃ | OCH₃ | CH₃ | H | CH₃ | CH₃ | H | 1.273 | 303.1 |

TABLE 1-continued (I)

| Ex. | $R^1$ | $R^2$ | $R^3$ | $R^4$ | $R^5$ | $R^6$ | $R^7$ | $R_t$ [min] | m/z |
|---|---|---|---|---|---|---|---|---|---|
| 120 | $SCH_3$ | $OCH_3$ | $CH_3$ | H | $OC_2H_5$ | $CH_3$ | H | 1.319 | 333.1 |
| 121 | $SCH_3$ | $OCH_3$ | $OCH_3$ | H | H | $t$-$C_4H_9$ | H | 1.323 | 374.2 |
| 122 | $SCH_3$ | $OCH_3$ | $OCH_3$ | H | H | $i$-$C_3H_7$ | H | 1.276 | 333.2 |
| 123 | $SCH_3$ | $OCH_3$ | $OCF_3$ | H | H | $OCH_3$ | H | 1.269 | 375.1 |
| 124 | $SCH_3$ | $OCH_3$ | $OCH_3$ | $OCH_3$ | H | H | $OCH_3$ | 1.112 | 351.1 |
| 125 | $SCH_3$ | $OCH_3$ | O-(c-$C_5H_9$) | H | H | $CH_3$ | H | 1.382 | 359.2 |
| 126 | $S(O)CH_3$ | OH | $CH_3$ | H | H | H | H | 0.735 | 277.0 |
| 127 | $S(O)_2CH_3$ | OH | $CH_3$ | H | H | H | H | 0.781 | 293.0 |
| 128 | $N(CH_3)_2$ | OH | $CH_3$ | H | H | H | H | 0.950 | 258.4 |
| 129 | $N(CH_3)_2$ | OH | $CH_3$ | H | H | $CH_3$ | H | 1.041 | 272.4 |
| 130 | $N(CH_3)_2$ | $OCH_3$ | $CH_3$ | H | H | H | H | 1.182 | 272.4 |
| 131 | $N(CH_3)_2$ | $OCH_3$ | $CH_3$ | H | H | $CH_3$ | H | 1.252 | 286.6 |
| 132 | c-$C_3H_5$ | OH | F | H | H | H | H | 0.952 | 258.8 |
| 133 | c-$C_3H_5$ | OH | F | H | F | H | H | 0.978 | 277.0 |
| 134 | c-$C_3H_5$ | OH | F | H | F | H | F | 0.983 | 294.8 |
| 135 | c-$C_3H_5$ | OH | F | H | H | Br | H | 1.038 | 338.8 |
| 136 | c-$C_3H_5$ | OH | F | H | Cl | C(O)O-$i$-$C_3H_7$ | H | 1.141 | 379.0 |
| 137 | c-$C_3H_5$ | OH | F | H | $CH_3$ | Cl | H | 1.093 | 307.0 |
| 138 | c-$C_3H_5$ | OH | F | $CH_3$ | H | H | Br | 1.107 | 350.9 |
| 139 | c-$C_3H_5$ | OH | F | $CH_3$ | H | H | 6-Br-2-F-3-$CH_3$-phenyl | 1.291 | 460.9 |
| 140 | c-$C_3H_5$ | OH | F | $OCH_3$ | Cl | H | H | 1.035 | 323.0 |
| 141 | c-$C_3H_5$ | OH | Cl | H | H | H | H | 1.105 | 274.3 |
| 142 | c-$C_3H_5$ | OH | Cl | H | H | F | H | 1.004 | 292.9 |
| 143 | c-$C_3H_5$ | OH | Cl | H | H | Cl | H | 1.071 | 308.9 |
| 144 | c-$C_3H_5$ | OH | Cl | H | H | $CH_3$ | H | 1.068 | 288.8 |
| 145 | c-$C_3H_5$ | OH | Cl | H | H | $OCH_3$ | H | 1.027 | 304.7 |
| 146 | c-$C_3H_5$ | OH | Cl | H | F | H | H | 1.010 | 292.7 |
| 147 | c-$C_3H_5$ | OH | Cl | H | F | H | Cl | 1.095 | 327.0 |
| 148 | c-$C_3H_5$ | OH | Cl | H | Cl | H | F | 1.123 | 327.0 |
| 149 | c-$C_3H_5$ | OH | Cl | H | Cl | H | Cl | 1.169 | 342.8 |
| 150 | c-$C_3H_5$ | OH | Cl | F | H | H | H | 1.035 | 292.9 |
| 151 | c-$C_3H_5$ | OH | Cl | Cl | H | H | H | 1.079 | 310.7 |
| 152 | c-$C_3H_5$ | OH | Br | H | H | H | H | 1.015 | 319.2 |
| 153 | c-$C_3H_5$ | OH | Br | H | H | $OCH_3$ | H | 1.027 | 351.2 |
| 154 | c-$C_3H_5$ | OH | CN | H | H | H | H | 0.863 | 266.0 |
| 155 | c-$C_3H_5$ | OH | CN | H | H | F | H | 0.928 | 384.4 |
| 156 | c-$C_3H_5$ | OH | CN | H | H | $CH_3$ | H | 0.956 | 280.5 |
| 157 | c-$C_3H_5$ | OH | CN | H | F | H | H | 0.922 | 284.4 |
| 158 | c-$C_3H_5$ | OH | CN | H | $CH_3$ | H | H | 0.948 | 280.4 |
| 159 | c-$C_3H_5$ | OH | CN | F | H | H | H | 0.899 | 284.3 |
| 160 | c-$C_3H_5$ | OH | $NO_2$ | H | H | H | H | 0.918 | 286.3 |
| 161 | c-$C_3H_5$ | OH | $CH_3$ | H | H | H | H | 0.989 | 254.8 |
| 162 | c-$C_3H_5$ | OH | $CH_3$ | H | H | H | $CH_3$ | 1.037 | 269.5 |
| 163 | c-$C_3H_5$ | OH | $CH_3$ | H | H | F | H | 0.997 | 272.8 |
| 164 | c-$C_3H_5$ | OH | $CH_3$ | H | H | Cl | H | 1.083 | 288.7 |
| 165 | c-$C_3H_5$ | OH | $CH_3$ | H | H | $CH_3$ | H | 1.020 | 269.1 |
| 166 | c-$C_3H_5$ | OH | $CH_3$ | H | H | $OCH_3$ | H | 0.990 | 285.3 |
| 167 | c-$C_3H_5$ | OH | $CH_3$ | H | F | $CH_3$ | H | 1.079 | 286.8 |
| 168 | c-$C_3H_5$ | OH | $CH_3$ | H | $CH_3$ | H | H | 1.060 | 268.8 |
| 169 | c-$C_3H_5$ | OH | $CH_3$ | H | $OCH_3$ | $CH_3$ | H | 1.061 | 298.8 |
| 170 | c-$C_3H_5$ | OH | $CH_3$ | F | H | H | H | 1.018 | 272.8 |
| 171 | c-$C_3H_5$ | OH | $CH_3$ | Cl | H | H | H | 1.081 | 288.8 |
| 172 | c-$C_3H_5$ | OH | $CH_3$ | $CH_3$ | H | H | H | 1.068 | 289.0 |
| 173 | c-$C_3H_5$ | OH | $CH_3$ | $CH_3$ | H | H | H | 1.049 | 268.9 |
| 174 | c-$C_3H_5$ | OH | $C_2H_5$ | H | H | H | H | 1.057 | 269.4 |
| 175 | c-$C_3H_5$ | OH | $i$-$C_3H_7$ | H | H | H | H | 1.116 | 283.4 |
| 176 | c-$C_3H_5$ | OH | $CF_3$ | H | H | H | H | 1.051 | 308.8 |
| 177 | c-$C_3H_5$ | OH | $OCH_3$ | H | H | H | H | 0.926 | 270.8 |
| 178 | c-$C_3H_5$ | OH | $OCH_3$ | H | H | H | Cl | 1.006 | 304.8 |
| 179 | c-$C_3H_5$ | OH | $OCH_3$ | H | H | $OCH_3$ | H | 0.912 | 301.1 |
| 180 | c-$C_3H_5$ | OH | $OCH_2OCH_3$ | H | H | H | H | 0.962 | 301.4 |

TABLE 1-continued

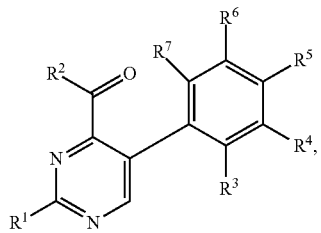

(I)

| Ex. | R¹ | R² | R³ | R⁴ | R⁵ | R⁶ | R⁷ | $R_t$ [min] | m/z |
|---|---|---|---|---|---|---|---|---|---|
| 181 | c-C₃H₅ | OH | OCHF₂ | H | H | H | H | 0.969 | 307.0 |
| 182 | c-C₃H₅ | OH | SCH₃ | H | H | H | H | 1.002 | 286.8 |
| 183 | c-C₃H₅ | OH | CH=CH₂ | H | H | H | H | 1.217 | 267.3 |
| 184 | c-C₃H₅ | OH | N(CH₃)₂ | H | H | H | H | 0.657 | 284.0 |
| 185 | c-C₃H₅ | OH | S(O)₂CH₃ | H | H | H | H | 0.820 | 319.3 |
| 186 | c-C₃H₅ | OH | S(O)CH₃ | H | H | H | H | 0.756 | 302.7 |
| 187 | c-C₃H₅ | OH | c-C₃H₅ | H | H | H | H | 1.072 | 281.4 |
| 188 | c-C₃H₅ | OH | C₆H₅ | H | H | H | H | 1.103 | 317.5 |
| 189 | c-C₃H₅ | OH | 2-Br-phenyl | H | H | H | H | 1.172 | 396.9 |
| 190 | c-C₃H₅ | OCH₃ | F | H | H | H | H | 1.103 | 272.8 |
| 191 | c-C₃H₅ | OCH₃ | F | H | H | Br | H | 1.220 | 353.2 |
| 192 | c-C₃H₅ | OCH₃ | F | H | F | H | H | 1.138 | 291.1 |
| 193 | c-C₃H₅ | OCH₃ | F | H | F | H | F | 1.144 | 308.8 |
| 194 | c-C₃H₅ | OCH₃ | F | H | Cl | H | Cl | 1.279 | 340.9 |
| 195 | c-C₃H₅ | OCH₃ | F | H | Cl | C(O)O-i-C₃H₇ | H | 1.312 | 293.3 |
| 196 | c-C₃H₅ | OCH₃ | F | H | CH₃ | Cl | H | 1.271 | 321.3 |
| 197 | c-C₃H₅ | OCH₃ | F | F | H | H | Br | 1.194 | 368.9 |
| 198 | c-C₃H₅ | OCH₃ | F | CH₃ | H | H | Br | 1.270 | 366.2 |
| 199 | c-C₃H₅ | OCH₃ | F | CH₃ | H | H | 6-Br-2-F-3-CH₃-phenyl | 1.392 | 474.8 |
| 200 | c-C₃H₅ | OCH₃ | F | OCH₃ | Cl | H | H | 1.210 | 337.3 |
| 201 | c-C₃H₅ | OCH₃ | Cl | H | H | H | H | 1.159 | 289.4 |
| 202 | c-C₃H₅ | OCH₃ | Cl | H | H | H | OCH₃ | 1.148 | 318.8 |
| 203 | c-C₃H₅ | OCH₃ | Cl | H | H | F | H | 1.177 | 307.3 |
| 204 | c-C₃H₅ | OCH₃ | Cl | H | H | Cl | H | 1.252 | 323.3 |
| 205 | c-C₃H₅ | OCH₃ | Cl | H | H | CH₃ | H | 1.230 | 303.5 |
| 206 | c-C₃H₅ | OCH₃ | Cl | H | H | OCH₃ | H | 1.166 | 319.5 |
| 207 | c-C₃H₅ | OCH₃ | Cl | H | F | H | H | 1.170 | 306.8 |
| 208 | c-C₃H₅ | OCH₃ | Cl | H | F | H | Cl | 1.253 | 340.9 |
| 209 | c-C₃H₅ | OCH₃ | Cl | H | Cl | H | Cl | 1.329 | 358.9 |
| 210 | c-C₃H₅ | OCH₃ | Cl | F | H | H | H | 1.201 | 306.9 |
| 211 | c-C₃H₅ | OCH₃ | Cl | Cl | H | H | H | 1.258 | 323.3 |
| 212 | c-C₃H₅ | OCH₃ | Cl | OCH₃ | H | H | Br | 1.232 | 398.9 |
| 213 | c-C₃H₅ | OCH₃ | Br | H | H | H | H | 1.170 | 332.7 |
| 214 | c-C₃H₅ | OCH₃ | Br | H | F | H | F | 1.200 | 368.9 |
| 215 | c-C₃H₅ | OCH₃ | Br | H | F | F | H | 1.202 | 368.8 |
| 216 | c-C₃H₅ | OCH₃ | Br | OCH₃ | H | H | F | 1.061 | 310.7 |
| 217 | c-C₃H₅ | OCH₃ | CN | H | H | H | H | 1.015 | 280.1 |
| 218 | c-C₃H₅ | OCH₃ | CN | H | H | F | H | 1.320 | 298.3 |
| 219 | c-C₃H₅ | OCH₃ | CN | H | H | CH₃ | H | 1.086 | 294.0 |
| 220 | c-C₃H₅ | OCH₃ | CN | H | F | H | H | 1.082 | 298.4 |
| 221 | c-C₃H₅ | OCH₃ | CN | H | CH₃ | H | H | 1.083 | 293.9 |
| 222 | c-C₃H₅ | OCH₃ | CN | F | H | H | H | 1.042 | 297.8 |
| 223 | c-C₃H₅ | OCH₃ | NO₂ | H | H | H | H | 1.068 | 300.3 |
| 224 | c-C₃H₅ | OCH₃ | CH₃ | H | H | H | H | 1.164 | 269.7 |
| 225 | c-C₃H₅ | OCH₃ | CH₃ | H | H | H | CH₃ | 1.213 | 283.6 |
| 226 | c-C₃H₅ | OCH₃ | CH₃ | H | H | F | H | 1.177 | 287.6 |
| 227 | c-C₃H₅ | OCH₃ | CH₃ | H | H | Cl | H | 1.231 | 303.5 |
| 228 | c-C₃H₅ | OCH₃ | CH₃ | H | H | CH₃ | H | 1.209 | 283.1 |
| 229 | c-C₃H₅ | OCH₃ | CH₃ | H | H | OCH₃ | H | 1.158 | 299.5 |
| 230 | c-C₃H₅ | OCH₃ | CH₃ | H | F | CH₃ | H | 1.248 | 301.6 |
| 231 | c-C₃H₅ | OCH₃ | CH₃ | H | CH₃ | H | H | 1.235 | 283.5 |
| 232 | c-C₃H₅ | OCH₃ | CH₃ | H | OCH₃ | CH₃ | H | 1.256 | 313.5 |
| 233 | c-C₃H₅ | OCH₃ | CH₃ | F | H | H | H | 1.211 | 287.5 |
| 234 | c-C₃H₅ | OCH₃ | CH₃ | Cl | H | H | H | 1.246 | 302.8 |
| 235 | c-C₃H₅ | OCH₃ | CH₃ | CH₃ | H | H | H | 1.253 | 302.9 |
| 236 | c-C₃H₅ | OCH₃ | CH₃ | CH₃ | H | H | H | 1.247 | 283.5 |
| 237 | c-C₃H₅ | OCH₃ | C₂H₅ | H | H | H | H | 1.235 | 282.9 |
| 238 | c-C₃H₅ | OCH₃ | i-C₃H₇ | H | H | H | H | 1.293 | 296.9 |
| 239 | c-C₃H₅ | OCH₃ | CF₃ | H | H | H | H | 1.185 | 322.8 |
| 240 | c-C₃H₅ | OCH₃ | OCH₃ | H | H | H | H | 1.094 | 285.7 |
| 241 | c-C₃H₅ | OCH₃ | OCH₃ | H | H | OCH₃ | H | 1.082 | 315.2 |

TABLE 1-continued $$(I)$$

[Structure: pyrimidine with R$^1$ at 2-position, C(O)R$^2$ at 4-position, and phenyl at 5-position bearing R$^3$, R$^4$, R$^5$, R$^6$, R$^7$]

| Ex. | R$^1$ | R$^2$ | R$^3$ | R$^4$ | R$^5$ | R$^6$ | R$^7$ | R$_t$ [min] | m/z |
|---|---|---|---|---|---|---|---|---|---|
| 242 | c-C$_3$H$_5$ | OCH$_3$ | OCHF$_2$ | H | H | H | H | 1.115 | 321.3 |
| 243 | c-C$_3$H$_5$ | OCH$_3$ | OCH$_2$OCH$_3$ | H | H | H | H | 1.113 | 315.4 |
| 244 | c-C$_3$H$_5$ | OCH$_3$ | SCH$_3$ | H | H | H | H | 1.177 | 301.5 |
| 245 | c-C$_3$H$_5$ | OCH$_3$ | CH=CH$_2$ | H | H | H | H | 1.197 | 280.9 |
| 246 | c-C$_3$H$_5$ | OCH$_3$ | N(CH$_3$)$_2$ | H | H | H | H | 0.943 | 298.5 |
| 247 | c-C$_3$H$_5$ | OCH$_2$ | S(O)CH$_3$ | H | H | H | H | 0.884 | 316.8 |
| 248 | c-C$_3$H$_5$ | OCH$_3$ | S(O)CH$_3$ | H | H | H | H | 0.937 | 332.8 |
| 249 | c-C$_3$H$_5$ | OCH$_3$ | C$_6$H$_5$ | H | H | H | H | 1.254 | 331.6 |
| 250 | c-C$_3$H$_5$ | OCH$_3$ | 2-Br-phenyl | H | H | H | H | 1.287 | 410.8 |
| 251 | c-C$_3$H$_5$ | OC$_2$H$_5$ | Cl | H | H | H | H | 1.212 | 302.7 |
| 252 | c-C$_3$H$_5$ | O-i-C$_3$H$_7$ | Cl | H | H | H | H | 1.269 | 316.9 |
| 253 | c-C$_3$H$_5$ | O-t-C$_4$H$_9$ | Cl | H | H | H | H | 1.148 | 330.4 |
| 254 | c-C$_3$H$_5$ | OCH$_2$—C$_6$H$_5$ | Cl | H | H | H | H | 1.332 | 364.8 |
| 255 | c-C$_3$H$_5$ | OC$_6$H$_5$ | Cl | H | H | H | H | 1.312 | 350.8 |
| 256 | c-C$_3$H$_5$ | OCH$_2$C≡CH | Cl | H | H | H | H | 1.217 | 313.3 |
| 257 | c-C$_3$H$_5$ | OCH$_2$CHF$_2$ | Cl | H | H | H | H | 1.237 | 339.3 |
| 258 | c-C$_3$H$_5$ | OCH$_2$CH$_2$Si(CH$_3$)$_3$ | Cl | H | H | H | H | 1.487 | 374.9 |
| 259 | c-C$_3$H$_5$ | O(4-OCH$_3$)phenyl | Cl | H | H | H | H | 1.324 | 382.7 |
| 260 | c-C$_3$H$_5$ | OCH$_2$CH$_3$ | Cl | H | H | H | H | 1.202 | 319.3 |
| 261 | c-C$_3$H$_5$ | OCH$_2$—C(O)OCH$_3$ | Cl | H | H | H | H | 1.195 | 347.3 |
| 262 | c-C$_3$H$_5$ | O-c-C$_3$H$_5$ | Cl | H | H | H | H | 1.219 | 314.8 |
| 263 | c-C$_4$H$_7$ | OH | CH$_3$ | H | H | H | H | 1.040 | 268.8 |
| 264 | c-C$_4$H$_7$ | OCH$_3$ | CH$_3$ | H | H | H | H | 1.244 | 283.5 |
| 265 | c-C$_5$H$_9$ | OH | CH$_3$ | H | H | H | H | 1.118 | 283.5 |
| 266 | c-C$_5$H$_9$ | OCH$_3$ | CH$_3$ | H | H | H | H | 1.293 | 297.6 |
| 267 | cyclopenten-1-yl | OH | Cl | H | H | H | H | 1.135 | 301.0 |
| 268 | 1-CH$_3$-cyclopropyl | OH | CH$_3$ | H | H | H | H | 1.112 | 269.4 |
| 269 | 1-CH$_3$-cyclopropyl | OCH$_3$ | CH$_3$ | H | H | H | H | 1.295 | 283.5 |
| 270 | C$_6$H$_5$ | OH | Cl | H | H | H | H | 2.390 | 311.0 |
| 271 | C$_6$H$_5$ | OH | CH$_3$ | H | H | H | H | 1.143 | 291.0 |
| 272 | C$_6$H$_5$ | OCH$_3$ | CH$_3$ | H | H | H | H | 1.317 | 305.4 |
| 273 | C$_6$H$_5$ | OCH$_3$ | Cl | H | H | H | H | 1.312 | 325.0 |
| 274 | 3-pyridyl | OCH$_3$ | CH$_3$ | H | H | H | H | 0.882 | 306.3 |
| 275 | tetrahydrofuran-2-yl | OH | CH$_3$ | H | H | H | H | 0.880 | 285.3 |
| 276 | tetrahydrofuran-2-yl | OCH$_3$ | CH$_3$ | H | H | H | H | 1.037 | 299.5 |
| 277 | c-C$_4$H$_7$ | OCH$_3$ | Cl | H | H | H | H | 1.220 | 302.8 |
| 278 | c-C$_3$H$_5$ | S—CH$_2$—C(O)OCH$_3$ | Cl | H | H | H | H | 1.235 | 362.7 |
| 279 | c-C$_3$H$_5$ | S—CH$_2$—C(O)OCH(CH$_3$)$_2$ | Cl | H | H | H | H | 1.344 | 390.8 |
| 280 | c-C$_3$H$_5$ | S—CH$_2$—C$_6$H$_5$ | Cl | H | H | H | H | 1.470 | 380.8 |
| 281 | c-C$_3$H$_5$ | S—C(CH$_3$)$_3$ | Cl | H | H | H | H | 1.473 | 346.8 |
| 282 | c-C$_3$H$_5$ | S—CH$_2$—(4-OCH$_3$-phenyl) | Cl | H | H | H | H | 1.435 | 410.8 |
| 283 | c-C$_3$H$_5$ | S—C(CH$_3$)$_2$—C(O)OCH$_3$ | Cl | H | H | H | H | 1.369 | 390.8 |
| 284 | 3-pyridyl | OH | CH$_3$ | H | H | H | H | 0.719 | 292.1 |
| 285 | c-C$_3$H$_5$ | N(CH$_3$)$_2$ | Cl | H | H | H | H | 1.055 | 302.4 |
| 286 | c-C$_3$H$_5$ | N(H)(SO$_2$CH$_3$) | Cl | H | H | H | H | 1.052 | 351.8 |
| 287 | c-C$_3$H$_5$ | N(H)[SO$_2$N(CH$_3$)$_2$] | Cl | H | H | H | H | 1.135 | 380.8 |
| 288 | c-C$_3$H$_5$ | NH$_2$ | Cl | H | H | H | H | 0.968 | 273.8 |
| 289 | c-C$_3$H$_5$ | N(H)(CH$_3$) | Cl | H | H | H | H | 1.067 | 288.4 |
| 290 | c-C$_3$H$_5$ | N(H)(OH) | Cl | H | H | H | H | 0.886 | 290.3 |
| 291 | c-C$_3$H$_5$ | SC$_2$H$_5$ | Cl | H | H | H | H | 1.402 | 319.4 |
| 292 | CH=CH$_2$ | OCH$_3$ | Cl | H | H | H | H | 1.081 | 275.0 |
| 293 | 2,2-difluoro-cyclopropyl | OCH$_3$ | Cl | H | H | H | H | 1.127 | 325.0 |
| 294 | c-C$_3$H$_5$ | OCH$_3$ | Cl | H | OCH$_3$ | H | H | 1.181 | 319.0 |
| 295 | c-C$_3$H$_5$ | OCH$_3$ | F | H | OCH$_3$ | H | H | 1.134 | 303.1 |
| 296 | c-C$_3$H$_5$ | OH | Cl | H | OCH$_3$ | H | H | 1.015 | 305.0 |
| 297 | c-C$_3$H$_5$ | OH | F | H | OCH$_3$ | H | H | 0.958 | 289.0 |
| 298 | c-C$_3$H$_5$ | OCH$_3$ | OCH$_3$ | H | H | F | H | 1.116 | 303.1 |
| 299 | c-C$_3$H$_5$ | OH | OCH$_3$ | H | H | F | H | 0.937 | 289.0 |
| 300 | c-C$_3$H$_5$ | OCH$_3$ | OCH$_3$ | H | F | H | H | 1.125 | 303.1 |
| 301 | c-C$_3$H$_5$ | OH | OCH$_3$ | H | F | H | H | 0.936 | 289.0 |
| 302 | c-C$_3$H$_5$ | OCH$_3$ | Cl | H | H | H | CF$_3$ | 1.248 | 356.9 |
| 303 | c-C$_3$H$_5$ | OH | OC$_2$H$_5$ | H | H | H | Br | 1.112 | 362.9 |
| 304 | c-C$_3$H$_5$ | OH | CF$_3$ | H | H | H | Cl | 1.117 | 342.9 |

TABLE 1-continued

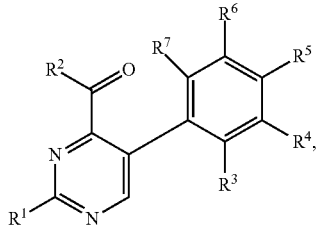

(I)

| Ex. | R¹ | R² | R³ | R⁴ | R⁵ | R⁶ | R⁷ | R_r [min] | m/z |
|---|---|---|---|---|---|---|---|---|---|
| 305 | c-C₃H₅ | OCH₃ | O(nC₃H₇) | H | H | CF₃ | H | 1.315 | 381.0 |
| 306 | c-C₃H₅ | OH | O(nC₃H₇) | H | H | CF₃ | H | 1.117 | 367.0 |
| 307 | c-C₃H₅ | SCH₂CH₂C(O)—OCH₃ | Cl | H | H | H | H | 1.320 | 377.0 |
| 308 | c-C₃H₅ | OCH₃ | CF₂H | H | H | H | H | 1.108 | 305.0 |
| 309 | c-C₃H₅ | OH | CF₂H | H | H | H | H | 0.968 | 291.0 |
| 310 | c-C₃H₅ | OH | SCF₃ | H | H | H | H | 1.118 | 341.0 |
| 311 | c-C₃H₅ | OH | I | H | H | H | H | 1.017 | 367.0 |
| 312 | c-C₃H₅ | OCH₃ | I | H | H | H | H | 1.193 | 380.9 |
| 313 | c-C₃H₅ | OH | F | H | H | C(O)CH₃ | H | 1.072 | 315.0 |
| 314 | c-C₃H₅ | OH | F | H | H | C(O)CH₃ | H | 0.909 | 300.8 |
| 315 | CF₃ | OH | Cl | H | H | H | H | 0.992 | 302.9- |
| 316 | CF₃ | OCH₃ | Cl | H | H | H | H | 1.145 | 317.0 |
| 317 | c-C₃H₅ | OH | F | H | H | H | I | 1.042 | 384.9 |
| 318 | c-C₃H₅ | OH | CO₂H | H | H | H | H | 0.802 | 285.1 |
| 319 | OCH₂C=CH | OH | Cl | H | H | H | H | 0.948 | 289.0 |
| 320 | OCH₂C=CH | OCH₃ | Cl | H | H | H | H | 1.071 | 303.0 |
| 321 | c-C₃H₅ | OCH3 | SCF₃ | H | H | H | H | 1.217 | 355.0 |

B USE EXAMPLES

The herbicidal activity of the phenylpyrimidines of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles.

The containers were irrigated gently to promote germination and growth and subsequently covered with transparent plastic hoods until the plants had rooted. This cover caused uniform germination of the test plants, unless this had been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively.

The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments were of the following species:

| Bayer code | Scientific name |
|---|---|
| ABUTH | Abutilon theophrasti |
| ALOMY | Alopercurus myosuroides |
| AMARE | Amaranthus retroflexus |
| APESV | Apera spica-venti |
| AVEFA | Avena fatua |
| ECHCG | Echinocloa crus-galli |
| LOLMU | Lolium multiflorum |
| POLCO | Polygonum convolvulus |
| SETFA | Setaria faberi |
| SETVI | Setaria viridis |

At an application rate of 1000 g/ha, example 2 applied by the pre-emergence method, showed good herbicidal activity against SETFA.

At an application rate of 1000 g/ha kg/ha, example 2 applied by the post-emergence method, showed good herbicidal activity against ABUTH and ECHCG.

At an application rate of 500 g/ha, example 141 applied by the pre-emergence method, showed very good herbicidal activity against APESV and ECHCG.

At an application rate of 500 g/ha kg/ha, example 141 applied by the post-emergence method, showed very good herbicidal activity against ALOMY and AVEFA.

At an application rate of 500 g/ha, example 146 applied by the pre-emergence method, showed very good herbicidal activity against APESV, ECHCG and ALOMY.

At an application rate of 500 g/ha kg/ha, example 146 applied by the post-emergence method, showed very good herbicidal activity against ALOMY.

At an application rate of 500 g/ha, example 152 applied by the pre-emergence method, showed very good herbicidal activity against APESV and ECHCG, and good herbicidal activity against ALOMY.

At an application rate of 500 g/ha kg/ha, example 152 applied by the post-emergence method, showed good herbicidal activity against AMARE.

At an application rate of 1000 g/ha, example 161 applied by the pre-emergence method, showed very good herbicidal activity against APESV.

At an application rate of 1000 g/ha kg/ha, example 161 applied by the post-emergence method, showed good herbicidal activity against ALOMY, AMARE, LOLMU and POLCO.

At an application rate of 500 g/ha, example 178 applied by the pre-emergence method, showed very good herbicidal activity against APESV and ECHCG.

At an application rate of 500 g/ha kg/ha, example 178 applied by the post-emergence method, showed good herbicidal activity against AVEFA and ALOMY.

At an application rate of 500 g/ha, example 201 applied by the pre-emergence method, showed very good herbicidal activity against APESV, ECHCG and ALOMY.

At an application rate of 500 g/ha, example 201 applied by the post-emergence method, showed very good herbicidal activity against POLCO and ALOMY.

At an application rate of 500 g/ha, example 207 applied by the pre-emergence method, showed very good herbicidal activity against APESV, ECHCG and ALOMY.

At an application rate of 500 g/ha kg/ha, example 207 applied by the post-emergence method, showed good herbicidal activity against ALOMY.

At an application rate of 500 g/ha, example 213 applied by the pre-emergence method, showed very good herbicidal activity against APESV, ECHCG and ALOMY.

At an application rate of 500 g/ha kg/ha, example 213 applied by the post-emergence method, showed good herbicidal activity against ALOMY and ECHCG.

At an application rate of 500 g/ha, example 260 applied by the pre-emergence method, showed very good herbicidal activity against APESV and ECHCG.

At an application rate of 500 g/ha, example 260 applied by the post-emergence method, showed very good herbicidal activity against ALOMY and AVEFA.

At an application rate of 500 g/ha, example 6 applied by the post-emergence method showed very good herbicidal activity against ECHCG and POLCO, and good herbicidal activity against LOLMU, and applied by the pre-emergence method showed very good herbicidal activity against APESV.

At an application rate of 1000 g/ha, example 7 applied by the pre-emergence method showed very good herbicidal activity against APESV and ECHCG.

At an application rate of 1000 g/ha, example 8 applied by the post-emergence method showed very good herbicidal activity against ECHCG, and good herbicidal activity against ABUTH, and applied by the pre-emergence method showed very good herbicidal activity against APESV and ECHCG.

At an application rate of 1000 g/ha, example 9 applied by the post-emergence method showed very good herbicidal activity against ABUTH, and good herbicidal activity against AMARE, and applied by the pre-emergence method showed very good herbicidal activity against APESV and SETFA.

At an application rate of 500 g/ha, example 10 applied by the pre-emergence method showed very good herbicidal activity against APESV and ECHCG.

At an application rate of 2000 g/ha, example 16 applied by the post-emergence method showed very good herbicidal activity against ABUTH, and applied by the pre-emergence method showed very good herbicidal activity against APESV and ECHCG.

At an application rate of 1000 g/ha, example 19 applied by the pre-emergence method showed very good herbicidal activity against APESV and ECHCG.

At an application rate of 1000 g/ha, example 20 applied by the post-emergence method showed good herbicidal activity against ECHCG, and applied by the pre-emergence method showed very good herbicidal activity against APESV and ECHCG.

At an application rate of 1000 g/ha, example 22 applied by the pre-emergence method showed good herbicidal activity against APESV and ECHCG.

At an application rate of 1000 g/ha, example 23 applied by the pre-emergence method showed very good herbicidal activity against APESV and ECHCG.

At an application rate of 1000 g/ha, example 32 applied by the post-emergence method showed very good herbicidal activity against ABUTH and good herbicidal activity against AMARE, and applied by the pre-emergence method showed very good herbicidal activity against APESV and ECHCG.

At an application rate of 500 g/ha, example 33 applied by the post-emergence method showed good herbicidal activity against ECHCG and POLCO, and applied by the pre-emergence method showed very good herbicidal activity against APESV and ECHCG.

At an application rate of 500 g/ha, example 34 applied by the post-emergence method showed very good herbicidal activity against ECHCG and good herbicidal activity against LOLMU, and applied by the pre-emergence method showed very good herbicidal activity against APESV and ECHCG.

At an application rate of 1000 g/ha, example 35 applied by the post-emergence method showed very good herbicidal activity against ABUTH, and applied by the pre-emergence method showed very good herbicidal activity against APESV and ECHCG.

At an application rate of 1000 g/ha, example 37 applied by the post-emergence method showed very good herbicidal activity against ECHCG, and applied by the pre-emergence method showed very good herbicidal activity against SETFA and ECHCG.

At an application rate of 1000 g/ha, example 38 applied by the pre-emergence method showed very good herbicidal activity against ECHCG, and good herbicidal activity against APESV.

At an application rate of 1000 g/ha, example 40 applied by the post-emergence method showed very good herbicidal activity against ABUTH and good herbicidal activity against ECHCG, and applied by the pre-emergence method showed good herbicidal activity against APESV.

At an application rate of 1000 g/ha, example 41 applied by the post-emergence method showed very good herbicidal activity against ABUTH and good herbicidal activity against ECHCG, and applied by the pre-emergence method showed very good herbicidal activity against APESV.

At an application rate of 500 g/ha, example 51 applied by the post-emergence method showed very good herbicidal activity against POLCO, and good herbicidal activity against AVEFA and ECHCG, and applied by the pre-emergence method showed very good herbicidal activity against APESV and ECHCG.

At an application rate of 2000 g/ha, example 52 applied by the post-emergence method showed good herbicidal activity against ALOMY, and applied by the pre-emergence method showed very good herbicidal activity against APESV and good herbicidal activity against ECHCG.

At an application rate of 1000 g/ha, example 54 applied by the post-emergence method showed very good herbicidal activity against ALOMY and AMARE, and good herbicidal activity against ABUTH, and applied by the pre-emergence method showed very good herbicidal activity against APESV and ECHCG.

At an application rate of 1000 g/ha, example 57 applied by the pre-emergence method showed very good herbicidal activity against APESV and ECHCG.

At an application rate of 500 g/ha, example 61 applied by the post-emergence method showed very good herbicidal activity against POLCO, and good herbicidal activity against ALOMY and ECHCG, and applied by the pre-emergence method showed very good herbicidal activity against APESV and ECHCG.

At an application rate of 1000 g/ha, example 62 applied by the pre-emergence method showed very good herbicidal activity against APESV and good herbicidal activity against ECHCG.

At an application rate of 1000 g/ha, example 64 applied by the post-emergence method, showed very good herbicidal activity against AMARE, ALOMY and SETVI.

At an application rate of 500 g/ha, example 67 applied by the post-emergence method showed very good herbicidal activity against POLCO, and good herbicidal activity against ECHCG, and applied by the pre-emergence method showed very good herbicidal activity against APESV and good herbicidal activity against ECHCG.

At an application rate of 500 g/ha, example 68 applied by the post-emergence method showed very good herbicidal activity against POLCO, and good herbicidal activity against ECHCG, and applied by the pre-emergence method showed very good herbicidal activity against APESV and ECHCG.

At an application rate of 1000 g/ha, example 71 applied by the pre-emergence method showed very good herbicidal activity against APESV and ECHCG.

At an application rate of 500 g/ha, example 72 applied by the post-emergence method showed very good herbicidal activity against AMARE and ECHCG.

At an application rate of 1000 g/ha, example 74 applied by the pre-emergence method showed good herbicidal activity against SETVI.

At an application rate of 2000 g/ha, example 83 applied by the post-emergence method, showed good herbicidal activity against ECHCG.

At an application rate of 1000 g/ha, example 86 applied by the pre-emergence method showed good herbicidal activity against SETFA and ECHCG.

At an application rate of 2000 g/ha, example 89 applied by the post-emergence method, showed very good herbicidal activity against AMARE and ECHCG.

At an application rate of 2000 g/ha, example 90 applied by the post-emergence method, showed very good herbicidal activity against AMARE and ECHCG, and good herbicidal activity against ABUTH.

At an application rate of 2000 g/ha, example 92 applied by the post-emergence method showed very good herbicidal activity against AMARE and good herbicidal activity against ECHCG, and applied by the pre-emergence method showed very good herbicidal activity against ECHCG and good herbicidal activity against APESV.

At an application rate of 2000 g/ha, example 93 applied by the post-emergence method, showed very good herbicidal activity against AMARE.

At an application rate of 1000 g/ha, example 94 applied by the post-emergence method, showed very good herbicidal activity against ECHCG and POLCO, and good herbicidal activity against ABUTH.

At an application rate of 2000 g/ha, example 96 applied by the post-emergence method, showed very good herbicidal activity against AMARE and SETVI.

At an application rate of 2000 g/ha, example 97 applied by the post-emergence method, showed very good herbicidal activity against AMARE and good herbicidal activity against ECHCG.

At an application rate of 2000 g/ha, example 99 applied by the post-emergence method, showed very good herbicidal activity against AMARE and SETVI, and good herbicidal activity against ECHCG.

At an application rate of 2000 g/ha, example 100 applied by the post-emergence method, showed good herbicidal activity against ECHCG.

At an application rate of 2000 g/ha, example 102 applied by the post-emergence method, showed very good herbicidal activity against AMARE.

At an application rate of 2000 g/ha, example 103 applied by the post-emergence method showed very good herbicidal activity against AMARE and ECHCG, and applied by the pre-emergence method showed good herbicidal activity against ECHCG.

At an application rate of 2000 g/ha, example 107 applied by the post-emergence method, showed very good herbicidal activity against AMARE.

At an application rate of 2000 g/ha, example 108 applied by the post-emergence method showed very good herbicidal activity against AMARE, and applied by the pre-emergence method showed very good herbicidal activity against ECHCG.

At an application rate of 2000 g/ha, example 109 applied by the post-emergence method, showed good herbicidal activity against SETVI.

At an application rate of 2000 g/ha, example 113 applied by the post-emergence method, showed very good herbicidal activity against AMARE.

At an application rate of 2000 g/ha, example 114 applied by the pre-emergence method, showed very good herbicidal activity against SETFA.

At an application rate of 500 g/ha, example 117 applied by the pre-emergence method showed good herbicidal activity against AMARE and ECHCG.

At an application rate of 2000 g/ha, example 126 applied by the post-emergence method, showed very good herbicidal activity against AMARE.

At an application rate of 2000 g/ha, example 127 applied by the pre-emergence method, showed good herbicidal activity against SETFA.

At an application rate of 500 g/ha, example 129 applied by the post-emergence method showed good herbicidal activity against ABUTH, and applied by the pre-emergence method showed very good herbicidal activity against APESV, and good herbicidal activity against ECHCG.

At an application rate of 500 g/ha, example 132 applied by the post-emergence method showed very good herbicidal activity against ALOMY and ECHCG, and applied by the pre-emergence method showed very good herbicidal activity against ECHCG, ALOMY and APESV.

At an application rate of 500 g/ha, example 133 applied by the post-emergence method showed very good herbicidal activity against ALOMY and AVEFA, and applied by the pre-emergence method showed very good herbicidal activity against ECHCG and APESV.

At an application rate of 500 g/ha, example 134 applied by the post-emergence method showed very good herbicidal activity against ALOMY and AVEFA, and applied by the pre-emergence method showed very good herbicidal activity against ECHCG and APESV.

At an application rate of 1000 g/ha, example 135 applied by the pre-emergence method showed very good herbicidal activity against APESV, and applied by the post-emergence method showed herbicidal activity against ALOMY.

At an application rate of 1000 g/ha, example 137 applied by the post-emergence method showed very good herbicidal activity against AMARE and SETVI.

At an application rate of 500 g/ha, example 142 applied by the post-emergence method showed very good herbicidal activity against ALOMY and ECHCG, and applied by the pre-emergence method showed very good herbicidal activity against ECHCG, APESV and ALOMY.

At an application rate of 500 g/ha, example 143 applied by the post-emergence method showed very good herbicidal activity against POLCO, and good herbicidal activity against ECHCG, and applied by the pre-emergence method showed very good herbicidal activity against ECHCG and APESV.

At an application rate of 500 g/ha, example 144 applied by the post-emergence method showed very good herbicidal activity against POLCO and SETVI, and applied by the pre-emergence method showed very good herbicidal activity against APESV and ECHCG.

At an application rate of 500 g/ha, example 145 applied by the post-emergence method showed very good herbicidal activity against POLCO and ECHCG, and applied by the pre-emergence method showed very good herbicidal activity against ECHCG and APESV.

At an application rate of 500 g/ha, example 147 applied by the post-emergence method showed very good herbicidal activity against ALOMY and POLCO, and applied by the pre-emergence method showed very good herbicidal activity against ALOMY and APESV.

At an application rate of 250 g/ha, example 148 applied by the post-emergence method showed very good herbicidal activity against ALOMY and POLCO, and applied by the pre-emergence method showed very good herbicidal activity against APESV.

At an application rate of 1000 g/ha, example 149 applied by the post-emergence method showed very good herbicidal activity against ALOMY and AVEFA, and applied by the pre-emergence method showed very good herbicidal activity against APESV.

At an application rate of 1000 g/ha, example 150 applied by the post-emergence method showed very good herbicidal activity against ALOMY and ABUTH, and applied by the pre-emergence method showed very good herbicidal activity against ECHCG and APESV.

At an application rate of 1000 g/ha, example 153 applied by the post-emergence method showed very good herbicidal activity against ECHCG, and applied by the pre-emergence method showed very good herbicidal activity against APESV.

At an application rate of 500 g/ha, example 154 applied by the post-emergence method showed very good herbicidal activity against ALOMY, and good herbicidal activity against ECHCG, and applied by the pre-emergence method showed very good herbicidal activity against ECHCG and APESV.

At an application rate of 500 g/ha, example 155 applied by the post-emergence method showed very good herbicidal activity against AMARE and ECHCG At an application rate of 1000 g/ha, example 157 applied by the post-emergence method showed very good herbicidal activity against ALOMY and AVEFA, and applied by the pre-emergence method showed very good herbicidal activity against APESV.

At an application rate of 1000 g/ha, example 160 applied by the post-emergence method showed very good herbicidal activity against ECHCG, and applied by the pre-emergence method showed very good herbicidal activity against ECHCG and APESV.

At an application rate of 500 g/ha, example 162 applied by the post-emergence method showed very good herbicidal activity against ALOMY and ECHCG, and applied by the pre-emergence method showed very good herbicidal activity against ECHCG, ALOMY and APESV.

At an application rate of 1000 g/ha, example 163 applied by the post-emergence method showed very good herbicidal activity against ECHCG and SETVI, and applied by the pre-emergence method showed very good herbicidal activity against APESV and ECHCG.

At an application rate of 500 g/ha, example 164 applied by the post-emergence method showed very good herbicidal activity against POLCO and ECHCG, and applied by the pre-emergence method showed very good herbicidal activity against ECHCG, APESV and ALOMY.

At an application rate of 500 g/ha, example 165 applied by the post-emergence method showed very good herbicidal activity against ALOMY and AVEFA, and applied by the pre-emergence method showed very good herbicidal activity against APESV.

At an application rate of 500 g/ha, example 166 applied by the post-emergence method showed good herbicidal activity against ALOMY and ECHCG, and applied by the pre-emergence method showed very good herbicidal activity against ECHCG and APESV.

At an application rate of 100 g/ha, example 167 applied by the post-emergence method showed very good herbicidal activity against ECHCG, and good herbicidal activity against AMARE, and applied by the pre-emergence method showed very good herbicidal activity against APESV and ECHCG.

At an application rate of 500 g/ha, example 168 applied by the post-emergence method showed very good herbicidal activity against POLCO, and good herbicidal activity against ALOMY, and applied by the pre-emergence method showed very good herbicidal activity against APESV and ECHCG.

At an application rate of 1000 g/ha, example 169 applied by the post-emergence method showed very good herbicidal activity against ABUTH and good herbicidal activity against ECHCG, and applied by the pre-emergence method showed very good herbicidal activity against APESV.

At an application rate of 1000 g/ha, example 170 applied by the post-emergence method showed very good herbicidal activity against ALOMY, and good herbicidal activity against ECHCG, and applied by the pre-emergence method showed very good herbicidal activity against ECHCG and APESV.

At an application rate of 1000 g/ha, example 172 applied by the post-emergence method showed very good herbicidal activity against ABUTH, and applied by the pre-emergence method showed very good herbicidal activity against APESV.

At an application rate of 500 g/ha, example 174 applied by the post-emergence method showed very good herbicidal activity against AMARE and ECHCG, and applied by the pre-emergence method showed very good herbicidal activity against ECHCG and APESV.

At an application rate of 1000 g/ha, example 175 applied by the pre-emergence method showed very good herbicidal activity against ECHCG and APESV.

At an application rate of 500 g/ha, example 176 applied by the post-emergence method showed very good herbicidal activity against AVEFA and POLCO, and applied by the pre-emergence method showed very good herbicidal activity against ALOMY and APESV.

At an application rate of 1000 g/ha, example 177 applied by the post-emergence method showed good herbicidal activity against ECHCG, and applied by the pre-emergence method showed very good herbicidal activity against APESV and ECHCG.

At an application rate of 2000 g/ha, example 179 applied by the post-emergence method showed very good herbicidal activity against ECHCG, and applied by the pre-emergence method showed very good herbicidal activity against APESV.

At an application rate of 1000 g/ha, example 180 applied by the post-emergence method showed very good herbicidal activity against ECHCG, and applied by the pre-emergence method showed very good herbicidal activity against ECHCG and APESV.

At an application rate of 500 g/ha, example 181 applied by the post-emergence method showed very good herbicidal activity against POLCO, and good herbicidal activity against ECHCG, and applied by the pre-emergence method showed very good herbicidal activity against ECHCG and APESV.

At an application rate of 500 g/ha, example 183 applied by the pre-emergence method showed very good herbicidal activity against ECHCG and APESV.

At an application rate of 1000 g/ha, example 187 applied by the post-emergence method showed very good herbicidal activity against ECHCG, and applied by the pre-emergence method showed very good herbicidal activity against ECHCG and APESV.

At an application rate of 500 g/ha, example 190 applied by the post-emergence method showed good herbicidal activity against POLCO, and applied by the pre-emergence method showed very good herbicidal activity against ECHCG, ALOMY and APESV.

At an application rate of 1000 g/ha, example 191 applied by the post-emergence method showed very good herbicidal activity against ECHCG, and good herbicidal activity against ALOMY and AVEFA, and applied by the pre-emergence method showed very good herbicidal activity against APESV and ECHCG.

At an application rate of 500 g/ha, example 192 applied by the post-emergence method showed very good herbicidal activity against ALOMY and AVEFA, and applied by the pre-emergence method showed very good herbicidal activity against ECHCG and APESV.

At an application rate of 500 g/ha, example 193 applied by the post-emergence method showed very good herbicidal activity against ALOMY and AVEFA, and applied by the pre-emergence method showed very good herbicidal activity against ECHCG and APESV.

At an application rate of 500 g/ha, example 194 applied by the post-emergence method showed very good herbicidal activity against AVEFA, and good herbicidal activity against ALOMY, and applied by the pre-emergence method showed good herbicidal activity against APESV.

At an application rate of 500 g/ha, example 195 applied by the post-emergence method showed very good herbicidal activity against ABUTH and AMARE.

At an application rate of 1000 g/ha, example 197 applied by the post-emergence method showed very good herbicidal activity against ALOMY and AVEFA, and applied by the pre-emergence method showed very good herbicidal activity against ECHCG and APESV.

At an application rate of 500 g/ha, example 198 applied by the post-emergence method showed very good herbicidal activity against ABUTH and SETVI, and applied by the pre-emergence method showed very good herbicidal activity against ECHCG and APESV.

At an application rate of 1000 g/ha, example 202 applied by the pre-emergence method showed very good herbicidal activity against ECHCG and good herbicidal activity against APESV, and applied by the post-emergence method showed very good herbicidal activity against ALOMY and good herbicidal activity against ECHCG.

At an application rate of 500 g/ha, example 203 applied by the post-emergence method showed very good herbicidal activity against ECHCG and good herbicidal activity against ALOMY, and applied by the pre-emergence method showed very good herbicidal activity against ECHCG, APESV and ALOMY.

At an application rate of 500 g/ha, example 204 applied by the post-emergence method showed very good herbicidal activity against AMARE and POLCO, and applied by the pre-emergence method showed very good herbicidal activity against APESV.

At an application rate of 500 g/ha, example 205 applied by the post-emergence method showed very good herbicidal activity against ECHCG, and good herbicidal activity against ALOMY, and applied by the pre-emergence method showed very good herbicidal activity against APESV and ECHCG, and good herbicidal activity against ALOMY.

At an application rate of 500 g/ha, example 206 applied by the post-emergence method showed good herbicidal activity against SETVI and ECHCG, and applied by the pre-emergence method showed very good herbicidal activity against ECHCG and APESV.

At an application rate of 1000 g/ha, example 208 applied by the post-emergence method showed very good herbicidal activity against ALOMY and AVEFA, and applied by the pre-emergence method showed very good herbicidal activity against APESV, and good herbicidal activity against AMARE.

At an application rate of 1000 g/ha, example 209 applied by the post-emergence method showed very good herbicidal activity against ALOMY and AVEFA, and applied by the pre-emergence method showed very good herbicidal activity against APESV.

At an application rate of 500 g/ha, example 210 applied by the post-emergence method showed very good herbicidal activity against ECHCG and POLCO, and applied by the pre-emergence method showed very good herbicidal activity against ECHCG and APESV.

At an application rate of 1000 g/ha, example 211 applied by the post-emergence method showed very good herbicidal activity against ALOMY and AMARE.

At an application rate of 500 g/ha, example 212 applied by the post-emergence method showed very good herbicidal activity against AMARE and ECHCG.

At an application rate of 500 g/ha, example 215 applied by the post-emergence method showed very good herbicidal activity against ALOMY and AVEFA, and applied by the pre-emergence method showed very good herbicidal activity against ECHCG and APESV.

At an application rate of 500 g/ha, example 217 applied by the post-emergence method showed very good herbicidal activity against ECHCG, and good herbicidal activity against ALOMY, and applied by the pre-emergence method showed very good herbicidal activity against ECHCG and APESV.

At an application rate of 500 g/ha, example 218 applied by the post-emergence method showed very good herbicidal activity against AVEFA and ECHCG, and applied by the pre-emergence method showed very good herbicidal activity against ECHCG and APESV.

At an application rate of 500 g/ha, example 220 applied by the post-emergence method showed very good herbicidal activity against ALOMY and AVEFA, and applied by the pre-emergence method showed very good herbicidal activity against APESV.

At an application rate of 1000 g/ha, example 223 applied by the post-emergence method showed very good herbicidal activity against ECHCG and SETVI, and applied by the pre-emergence method showed very good herbicidal activity against ECHCG and APESV.

At an application rate of 500 g/ha, example 225 applied by the post-emergence method showed very good herbicidal activity against POLCO, and good herbicidal activity against ECHCG, and applied by the pre-emergence method showed very good herbicidal activity against ECHCG and APESV.

At an application rate of 500 g/ha, example 226 applied by the post-emergence method showed very good herbicidal activity against POLCO and ALOMY, and applied by the pre-emergence method showed very good herbicidal activity against ALOMY and ECHCG and good herbicidal activity against APESV.

At an application rate of 500 g/ha, example 227 applied by the post-emergence method showed very good herbicidal activity against ALOMY and ECHCG, and applied by the pre-emergence method showed very good herbicidal activity against ECHCG, APESV and ALOMY.

At an application rate of 2000 g/ha, example 228 applied by the post-emergence method showed very good herbicidal activity against ALOMY and ECHCG, and applied by the pre-emergence method showed very good herbicidal activity against APESV.

At an application rate of 500 g/ha, example 229 applied by the post-emergence method showed very good herbicidal activity against ECHCG, and good herbicidal activity against ALOMY, and applied by the pre-emergence method showed very good herbicidal activity against ECHCG and APESV.

At an application rate of 500 g/ha, example 230 applied by the post-emergence method showed very good herbicidal activity against ECHCG, and good herbicidal activity against ALOMY, and applied by the pre-emergence method showed very good herbicidal activity against APESV and ECHCG, and good herbicidal activity against ALOMY.

At an application rate of 1000 g/ha, example 231 applied by the post-emergence method showed good herbicidal activity against ALOMY and ECHCG, and applied by the pre-emergence method showed very good herbicidal activity against APESV and ECHCG.

At an application rate of 1000 g/ha, example 232 applied by the post-emergence method showed very good herbicidal activity against ABUTH and ECHCG, and applied by the pre-emergence method showed very good herbicidal activity against APESV and ECHCG.

At an application rate of 1000 g/ha, example 237 applied by the post-emergence method showed very good herbicidal activity against AMARE and ECHCG, and applied by the pre-emergence method showed very good herbicidal activity against ECHCG.

At an application rate of 1000 g/ha, example 239 applied by the post-emergence method showed very good herbicidal activity against AVEFA, and applied by the pre-emergence method showed very good herbicidal activity against ECHCG and APESV.

At an application rate of 1000 g/ha, example 214 applied by the post-emergence method showed very good herbicidal activity against ALOMY and AVEFA, and applied by the pre-emergence method showed very good herbicidal activity against ECHCG and APESV.

At an application rate of 500 g/ha, example 242 applied by the post-emergence method showed very good herbicidal activity against AMARE, and good herbicidal activity against ECHCG, and applied by the pre-emergence method showed very good herbicidal activity against ECHCG.

At an application rate of 500 g/ha, example 251 applied by the post-emergence method showed very good herbicidal activity against ABUTH and AMARE, and applied by the pre-emergence method showed very good herbicidal activity against ALOMY and APESV.

At an application rate of 1000 g/ha, example 252 applied by the post-emergence method showed very good herbicidal activity against ALOMY and AVEFA, and applied by the pre-emergence method showed very good herbicidal activity against ECHCG.

At an application rate of 1000 g/ha, example 254 applied by the post-emergence method showed very good herbicidal activity against ALOMY, AVEFA and ECHCG, and applied by the pre-emergence method showed very good herbicidal activity against ECHCG and APESV.

At an application rate of 1000 g/ha, example 255 applied by the post-emergence method showed very good herbicidal activity against ALOMY, AVEFA and ECHCG, and applied by the pre-emergence method showed very good herbicidal activity against ECHCG and APESV.

At an application rate of 500 g/ha, example 256 applied by the post-emergence method showed very good herbicidal activity against APESV, AVEFA and ECHCG, and applied by the pre-emergence method showed very good herbicidal activity against ECHCG, AVEFA and APESV.

At an application rate of 500 g/ha, example 257 applied by the post-emergence method showed very good herbicidal activity against ALOMY and AVEFA, and good herbicidal activity against ECHCG, and applied by the pre-emergence method showed very good herbicidal activity against ECHCG, POLCO and APESV.

At an application rate of 1000 g/ha, example 258 applied by the post-emergence method showed very good herbicidal activity against ALOMY, AVEFA and ECHCG, and applied by the pre-emergence method showed very good herbicidal activity against ECHCG At an application rate of 500 g/ha, example 259 applied by the post-emergence method showed very good herbicidal activity against ALOMY and AVEFA, and good herbicidal activity against ECHCG, and applied by the pre-emergence method showed very good herbicidal activity against ECHCG and APESV.

At an application rate of 1000 g/ha, example 261 applied by the post-emergence method showed very good herbicidal activity against ALOMY and ECHCG, and applied by the pre-emergence method showed very good herbicidal activity against ECHCG and APESV.

At an application rate of 500 g/ha, example 262 applied by the post-emergence method showed good herbicidal activity against AVEFA, and applied by the pre-emergence method showed very good herbicidal activity against ECHCG and APESV.

At an application rate of 1000 g/ha, example 263 applied by the post-emergence method showed very good herbicidal activity against ABUTH and ECHCG, and applied by the pre-emergence method showed good herbicidal activity against APESV.

At an application rate of 1000 g/ha, example 264 applied by the post-emergence method showed very good herbicidal activity against ABUTH and AMARE, and applied by the pre-emergence method showed very good herbicidal activity against SETFA and good herbicidal activity against APESV.

At an application rate of 500 g/ha, example 271 applied by the post-emergence method showed very good herbicidal activity against ABUTH and ECHCG, and applied by the pre-emergence method showed good herbicidal activity against SETFA.

At an application rate of 1000 g/ha, example 276 applied by the post-emergence method showed very good herbicidal activity against AMARE and ABUTH, and applied by the pre-emergence method showed very good herbicidal activity against AMARE.

At an application rate of 500 g/ha, example 277 applied by the post-emergence method showed very good herbicidal activity against ABUTH, and applied by the pre-emergence method showed good herbicidal activity against APESV.

At an application rate of 500 g/ha, example 278 applied by the pre-emergence method showed very good herbicidal activity against APESV and ECHCG, and applied by the post-emergence method showed very good herbicidal activity against POLCO.

At an application rate of 500 g/ha, example 279 applied by the pre-emergence method showed very good herbicidal activity against APESV and ECHCG, and applied by the post-emergence method showed very good herbicidal activity against AVEFA.

At an application rate of 500 g/ha, example 280 applied by the pre-emergence method showed very good herbicidal activity against APESV, and applied by the post-emergence method showed very good herbicidal activity against AMARE.

At an application rate of 500 g/ha, example 281 applied by the pre-emergence method showed very good herbicidal activity against APESV, and applied by the post-emergence method showed very good herbicidal activity against ALOMY and POLCO.

At an application rate of 500 g/ha, example 282 applied by the pre-emergence method showed very good herbicidal activity against APESV, and applied by the post-emergence method showed very good herbicidal activity against AVEFA.

At an application rate of 500 g/ha, example 283 applied by the pre-emergence method showed very good herbicidal activity against APESV and ALOMY, and applied by the post-emergence method showed very good herbicidal activity against AVEFA and POLCO.

At an application rate of 500 g/ha, example 285 applied by the pre-emergence method showed good herbicidal activity against APESV and AMARE.

At an application rate of 500 g/ha, example 286 applied by the pre-emergence method showed very good herbicidal activity against APESV and ECHCG, and applied by the post-emergence method showed very good herbicidal activity against AMARE and LOLMU.

At an application rate of 500 g/ha, example 287 applied by the pre-emergence method showed very good herbicidal activity against AMARE and APESV, and applied by the post-emergence method showed very good herbicidal activity against ECHCG, LOLMU and POLCO.

At an application rate of 500 g/ha, example 288 applied by the pre-emergence method showed very good herbicidal activity against AMARE and APESV, and applied by the post-emergence method showed very good herbicidal activity against SETVI and POLCO.

At an application rate of 1000 g/ha, example 289 applied by the pre-emergence method showed very good herbicidal activity against APESV and good herbicidal activity against ECHCG, and applied by the post-emergence method showed good herbicidal activity against SETVI.

At an application rate of 500 g/ha, example 290 applied by the pre-emergence method showed very good herbicidal activity against APESV and ECHCG, and applied by the post-emergence method showed very good herbicidal activity against ALOMY and AVEFA.

At an application rate of 500 g/ha, example 291 applied by the pre-emergence method showed very good herbicidal activity against APESV and ECHCG, and applied by the post-emergence method showed very good herbicidal activity against AVEFA and ECHCG.

At an application rate of 1000 g/ha, example 292 applied by the post-emergence method showed very good herbicidal activity against AMARE.

At an application rate of 1000 g/ha, example 293 applied by the post-emergence method showed good herbicidal activity against AMARE.

At an application rate of 1000 g/ha, example 294 applied by the post-emergence method showed good herbicidal activity against ECHCG.

At an application rate of 500 g/ha, example 295 applied by the post-emergence method showed good herbicidal activity against AMARE.

At an application rate of 1000 g/ha, example 296 applied by the pre-emergence method showed very good herbicidal activity against APESV.

At an application rate of 1000 g/ha, example 297 applied by the pre-emergence method showed very good herbicidal activity against APESV.

At an application rate of 1000 g/ha, example 301 applied by the pre-emergence method showed very good herbicidal activity against ECHCG and good herbicidal activity against APESV.

At an application rate of 1000 g/ha, example 302 applied by the pre-emergence method showed very good herbicidal activity against SETFA, and applied by the post-emergence method showed very good herbicidal activity against AMARE and ECHCG.

At an application rate of 1000 g/ha, example 303 applied by the pre-emergence method showed very good herbicidal activity against APESV and SETFA, and applied by the post-emergence method showed very good herbicidal activity against ECHCG.

At an application rate of 1000 g/ha, example 304 applied by the pre-emergence method showed very good herbicidal activity against APESV, and applied by the post-emergence method showed very good herbicidal activity against AVEFA, ALOMY and ECHCG.

At an application rate of 1000 g/ha, example 306 applied by the post-emergence method showed very good herbicidal activity against ABUTH.

At an application rate of 250 g/ha, example 307 applied by the post-emergence method showed very good herbicidal activity against AVEFA and LOLMU, and good herbicidal activity against ECHCG, and applied by the pre-emergence method showed very good herbicidal activity against APESV.

At an application rate of 500 g/ha, example 308 applied by the pre-emergence method showed very good herbicidal activity against APESV and ECHCG, and applied by the post-emergence method showed very good herbicidal activity against ALOMY, AVEFA and POLCO.

At an application rate of 500 g/ha, example 309 applied by the pre-emergence method showed very good herbicidal activity against APESV and ECHCG, and applied by the post-emergence method showed very good herbicidal activity against ALOMY, AVEFA and POLCO.

At an application rate of 1000 g/ha, example 321 applied by the post-emergence method showed herbicidal activity against AVEFA.

At an application rate of 1000 g/ha, example 310 applied by the post-emergence method showed good herbicidal activity against ABUTH.

At an application rate of 500 g/ha, example 311 applied by the pre-emergence method showed very good herbicidal activity against APESV and ECHCG, and applied by the post-emergence method showed very good herbicidal activity against ALOMY, AVEFA and ECHCG.

At an application rate of 500 g/ha, example 312 applied by the pre-emergence method showed very good herbicidal activity against APESV and ECHCG, and applied by the post-emergence method showed very good herbicidal activity against ALOMY, AVEFA and ECHCG.

At an application rate of 500 g/ha, example 313 applied by the pre-emergence method showed good herbicidal activity against ABUTH.

At an application rate of 1000 g/ha, example 315 applied by the pre-emergence method showed very good herbicidal activity against ECHCG and good herbicidal activity against APESV, and applied by the post-emergence method showed good herbicidal activity against ALOMY, AVEFA and ECHCG.

At an application rate of 1000 g/ha, example 316 applied by the pre-emergence method showed good herbicidal activity against APESV and ECHCG, and applied by the post-emergence method showed good herbicidal activity against AVEFA.

At an application rate of 1000 g/ha, example 317 applied by the pre-emergence method showed very good herbicidal activity against APESV and ECHCG, and applied by the post-emergence method showed very good herbicidal activity against ALOMY, AVEFA and SETVI.

At an application rate of 2000 g/ha, example 318 applied by the pre-emergence method showed very good herbicidal activity against ECHCG, and applied by the post-emergence method showed very good herbicidal activity against ABUTH.

The invention claimed is:
1. A method for controlling undesired vegetation or harmful plants comprising allowing a herbicidal active amount of at least one compound of formula (I)

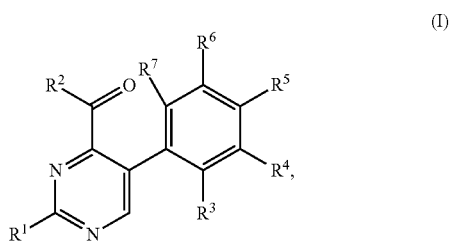

or agriculturally acceptable salt or derivative, wherein in formula (I) the variables have the following meanings:

$R^1$ $C_1$-$C_6$-alkyl, $C_1$-$C_6$-haloalkyl, hydroxy-$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkinyloxy, $C_3$-$C_6$-haloalkinyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, 5 or 6-membered heteroaryl, or 3- to 6-membered heterocyclyl, wherein the cycloalkyl, heteroaryl and heterocyclyl substituents independently of one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^2$ H, halogen, $C_1$-$C_6$-alkyl, $C_1$-$C_6$-haloalkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkylcarbonyl-$C_1$-$C_6$-alkyl, $C_1$-$C_6$-haloalkoxycarbonyl-$C_1$-$C_6$-alkyl, $C_1$-$C_6$-alkylcarbonyl-$C_1$-$C_6$-haloalkyl, $C_1$-$C_6$-alkoxycarbonyl-$C_1$-$C_6$-haloalkyl, $C_1$-$C_6$-haloalkylcarbonyl-$C_1$-$C_6$-haloalkyl, $C_1$-$C_6$-haloalkoxycarbonyl-$C_1$-$C_6$-haloalkyl, OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy, $C_1$-$C_6$-haloalkoxy, $C_1$-$C_6$-cyanoalkoxy, $C_1$-$C_6$-hydroxyalkoxy, $C_2$-$C_6$-alkenyloxy, $C_2$-$C_6$-alkenyloxy-$C_1$-$C_6$-alkoxy, $C_2$-$C_6$-haloalkenyloxy-$C_1$-$C_6$-haloalkoxy, $C_2$-$C_6$-alkenyloxy-$C_1$-$C_6$-haloalkoxy, $C_2$-$C_6$-haloalkenyloxy, $C_2$-$C_6$-alkynyloxy, $C_2$-$C_6$-haloalkynyloxy, $C_2$-$C_6$-alkynyloxy-$C_1$-$C_6$-alkoxy, $C_2$-$C_6$-haloalkynyloxy-$C_1$-$C_6$-haloalkoxy, $C_2$-$C_6$-alkynyloxy-$C_1$-$C_6$-haloalkoxy, $C_2$-$C_6$-alkynyloxy-$C_2$-$C_6$-alkenyloxy, $C_2$-$C_6$-haloalkynyloxy-$C_2$-$C_6$-alkenyloxy, $C_2$-$C_6$-alkynyloxy-$C_2$-$C_6$-haloalkenyloxy, $C_2$-$C_6$-haloalkynyloxy-$C_2$-$C_6$-haloalkenyloxy, $C_2$-$C_6$-alkynyloxy-$C_2$-$C_6$-alkynyloxy, $C_2$-$C_6$-haloalkynyloxy-$C_2$-$C_6$-alkynyloxy, $C_2$-$C_6$-alkynyloxy-$C_2$-$C_6$-haloalkynyloxy, $C_2$-$C_6$-haloalkynyloxy-$C_2$-$C_6$-haloalkynyloxy, ($C_1$-$C_6$-alkyl)carbonyl-$C_1$-$C_6$-alkoxy, ($C_1$-$C_6$-haloalkyl)carbonyl-$C_1$-$C_6$- haloalkoxy, (C$_1$-C$_6$-haloalkyl)carbonyl-C$_1$-C$_6$-alkoxy, (C$_1$-C$_6$-alkyl)carbonyl-C$_1$-C$_6$-haloalkoxy, (C$_1$-C$_6$-alkoxy)carbonyl-C$_1$-C$_6$-alkoxy, (C$_1$-C$_6$-haloalkoxy)carbonyl-C$_1$-C$_6$-alkoxy, (C$_1$-C$_6$-alkoxy)carbonyl-C$_1$-C$_6$-haloalkoxy, (C$_1$-C$_6$-haloalkoxy)-carbonyl-C$_1$-C$_6$-haloalkoxy, (C$_1$-C$_6$-alkoxy-C$_1$-C$_6$-alkyl)carbonyl-C$_1$-C$_6$-alkoxy, (C$_1$-C$_6$-haloalkoxy-C$_1$-C$_6$-alkyl)carbonyl-C$_1$-C$_6$-alkoxy, (C$_1$-C$_6$-alkoxy-C$_1$-C$_6$-haloalkyl)carbonyl-C$_1$-C$_6$-alkoxy, (C$_1$-C$_6$-alkoxy-C$_1$-C$_6$-alkyl)carbonyl-C$_1$-C$_6$-haloalkoxy, (C$_1$-C$_6$-haloalkoxy-C$_1$-C$_6$-haloalkyl)carbonyl-C$_1$-C$_6$-alkoxy, (C$_1$-C$_6$-haloalkoxy-C$_1$-C$_6$-alkyl)carbonyl-C$_1$-C$_6$-haloalkoxy, (C$_1$-C$_6$-alkoxy-C$_1$-C$_6$-haloalkyl)carbonyl-C$_1$-C$_6$-haloalkoxy, (C$_1$-C$_6$-haloalkoxy-C$_1$-C$_6$-haloalkyl)carbonyl-C$_1$-C$_6$-haloalkoxy, (C$_1$-C$_6$-alkylthio)carbonyl-C$_1$-C$_6$-alkoxy, (C$_1$-C$_6$-haloalkylthio)-carbonyl-C$_1$-C$_6$-alkoxy, (C$_1$-C$_6$-alkylthio)carbonyl-C$_1$-C$_6$-haloalkoxy, (C$_1$-C$_6$-haloalkylthio)carbonyl-C$_1$-C$_6$-haloalkoxy, (C$_1$-C$_6$-alkylthio-C$_1$-C$_6$-alkyl)carbonyl-C$_1$-C$_6$-alkoxy, (C$_1$-C$_6$-haloalkylthio-C$_1$-C$_6$-alkyl)carbonyl-C$_1$-C$_6$-alkoxy, (C$_1$-C$_6$-alkylthio-C$_1$-C$_6$-haloalkyl)carbonyl-C$_1$-C$_6$-alkoxy, (C$_1$-C$_6$-alkylthio-C$_1$-C$_6$-alkyl)carbonyl-C$_1$-C$_6$-haloalkoxy, (C$_1$-C$_6$-haloalkylthio-C$_1$-C$_6$-haloalkyl)carbonyl-C$_1$-C$_6$-alkoxy, (C$_1$-C$_6$-haloalkylthio-C$_1$-C$_6$-alkyl)carbonyl-C$_1$-C$_6$-haloalkoxy, (C$_1$-C$_6$-alkylthio-C$_1$-C$_6$-haloalkyl)carbonyl-C$_1$-C$_6$-haloalkoxy, (C$_1$-C$_6$-haloalkylthio-C$_1$-C$_6$-haloalkyl)carbonyl-C$_1$-C$_6$-haloalkoxy, C$_3$-C$_6$-cycloalkoxy, C$_3$-C$_6$-halocycloalkoxy, (C$_3$-C$_6$-cycloalkyl)C$_1$-C$_6$-alkoxy, (C$_3$-C$_6$-halocycloalkyl)C$_1$-C$_6$-alkoxy, (C$_3$-C$_6$-cycloalkyl)C$_1$-C$_6$-haloalkoxy, aminocarbonyl-C$_1$-C$_6$-alkoxy, (C$_3$-C$_6$-halocycloalkyl)-C$_1$-C$_6$-haloalkoxy, aminocarbonyl-C$_1$-C$_6$-haloalkoxy, N—(C$_1$-C$_6$-alkyl)-aminocarbonyl-C$_1$-C$_6$-alkoxy, N—(C$_1$-C$_6$-alkyl)-aminocarbonyl-C$_1$-C$_6$-haloalkoxy, N,N-di(C$_1$-C$_6$-alkyl)-aminocarbonyl-C$_1$-C$_6$-alkoxy, N,N-di(C$_1$-C$_6$-alkyl)-aminocarbonyl-C$_1$-C$_6$-haloalkoxy, O—N=C(di(phenyl), O—N=C(phenyl)(C$_1$-C$_6$-alkyl), O—N=C[di(C$_1$-C$_6$-alkyl)], (C$_1$-C$_6$-alkyl)$_3$-silyl-C$_1$-C$_6$-alkoxy, C$_1$-C$_6$-alkylthio, C$_1$-C$_6$-haloalkylthio, C$_1$-C$_6$-alkoxy-C$_1$-C$_6$-alkylthio, C$_1$-C$_6$-halo-alkoxy-C$_1$-C$_6$-alkylthio, C$_1$-C$_6$-alkoxy-C$_1$-C$_6$-haloalkylthio, C$_1$-C$_6$-haloalkoxy-C$_1$-C$_6$-haloalkylthio, C$_1$-C$_6$-alkoxy-C$_1$-C$_6$-alkoxy-C$_1$-C$_6$-alkylthio, C$_1$-C$_6$-cyanoalkylthio, C$_2$-C$_6$-alkenylthio, C$_2$-C$_6$-haloalkenylthio, C$_2$-C$_6$-alkenyloxy-C$_1$-C$_6$-alkylthio, C$_2$-C$_6$-haloalkenyloxy-C$_1$-C$_6$-alkylthio, C$_2$-C$_6$-alkenyloxy-C$_1$-C$_6$-haloalkylthio, C$_2$-C$_6$-haloalkenyloxy-C$_1$-C$_6$-haloalkylthio, C$_2$-C$_6$-alkynylthio, C$_2$-C$_6$-haloalkynylthio, C$_2$-C$_6$-alkynyloxy-C$_1$-C$_6$-alkylthio, C$_2$-C$_6$-haloalkynyloxy-C$_1$-C$_6$-haloalkylthio, C$_2$-C$_6$-alkynyloxy-C$_1$-C$_6$-haloalkylthio, C$_2$-C$_6$-alkynyloxy-C$_2$-C$_6$-alkenylthio, C$_2$-C$_6$-haloalkynyloxy-C$_2$-C$_6$-alkenylthio, C$_2$-C$_6$-alkynyloxy-C$_2$-C$_6$-haloalkenylthio, C$_2$-C$_6$-haloalkynyloxy-C$_2$-C$_6$-haloalkenylthio, C$_2$-C$_6$-alkynyloxy-C$_2$-C$_6$-alkynylthio, C$_2$-C$_6$-haloalkynyloxy-C$_2$-C$_6$-alkynylthio, C$_2$-C$_6$-alkynyloxy-C$_2$-C$_6$-haloalkynylthio, C$_2$-C$_6$-haloalkynyloxy-C$_2$-C$_6$-haloalkynylthio, (C$_1$-C$_6$-alkyl)carbonyl-C$_1$-C$_6$-alkylthio, (C$_1$-C$_6$-haloalkyl)carbonyl-C$_1$-C$_6$-alkylthio, (C$_1$-C$_6$-alkyl)carbonyl-C$_1$-C$_6$-haloalkylthio, (C$_1$-C$_6$-haloalkyl)carbonyl-C$_1$-C$_6$-haloalkylthio, (C$_1$-C$_6$-alkoxy)carbonyl-C$_1$-C$_6$-alkylthio, (C$_1$-C$_6$-haloalkoxy)carbonyl-C$_1$-C$_6$-alkylthio, (C$_1$-C$_6$-alkoxy)carbonyl-C$_1$-C$_6$-haloalkylthio, (C$_1$-C$_6$-haloalkoxy)carbonyl-C$_1$-C$_6$-haloalkylthio, (C$_1$-C$_6$-alkoxy-C$_1$-C$_6$-alkyl)carbonyl-C$_1$-C$_6$-alkylthio, (C$_1$-C$_6$-haloalkoxy-C$_1$-C$_6$-alkyl)carbonyl-C$_1$-C$_6$-alkylthio, (C$_1$-C$_6$-alkoxy-C$_1$-C$_6$-haloalkyl)carbonyl-C$_1$-C$_6$-alkylthio, (C$_1$-C$_6$-alkoxy-C$_1$-C$_6$-alkyl)carbonyl-C$_1$-C$_6$-haloalkylthio, (C$_1$-C$_6$-haloalkoxy-C$_1$-C$_6$-haloalkyl)carbonyl-C$_1$-C$_6$-alkylthio, (C$_1$-C$_6$-haloalkoxy-C$_1$-C$_6$-alkyl)carbonyl-C$_1$-C$_6$-haloalkylthio, (C$_1$-C$_6$-alkoxy-C$_1$-C$_6$-haloalkyl)carbonyl-C$_1$-C$_6$-haloalkylthio, (C$_1$-C$_6$-haloalkoxy-C$_1$-C$_6$-haloalkyl)carbonyl-C$_1$-C$_6$-haloalkylthio, (C$_1$-C$_6$-alkylthio)carbonyl-C$_1$-C$_6$-alkylthio, (C$_1$-C$_6$-haloalkylthio)carbonyl-C$_1$-C$_6$-alkylthio, (C$_1$-C$_6$-alkylthio)carbonyl-C$_1$-C$_6$-haloalkylthio, (C$_1$-C$_6$-haloalkylthio)carbonyl-C$_1$-C$_6$-haloalkylthio, (C$_1$-C$_6$-alkylthio-C$_1$-C$_6$-alkyl)carbonyl-C$_1$-C$_6$-alkylthio, (C$_1$-C$_6$-haloalkylthio-C$_1$-C$_6$-alkyl)carbonyl-C$_1$-C$_6$-alkylthio, (C$_1$-C$_6$-alkylthio-C$_1$-C$_6$-haloalkyl)carbonyl-C$_1$-C$_6$-alkylthio, (C$_1$-C$_6$-alkylthio-C$_1$-C$_6$-alkyl)carbonyl-C$_1$-C$_6$-haloalkylthio, (C$_1$-C$_6$-haloalkylthio-C$_1$-C$_6$-haloalkyl)carbonyl-C$_1$-C$_6$-alkylthio, (C$_1$-C$_6$-haloalkylthio-C$_1$-C$_6$-alkyl)carbonyl-C$_1$-C$_6$-haloalkylthio, (C$_1$-C$_6$-alkylthio-C$_1$-C$_6$-haloalkyl)carbonyl-C$_1$-C$_6$-haloalkylthio, (C$_1$-C$_6$-haloalkylthio-C$_1$-C$_6$-haloalkyl)carbonyl-C$_1$-C$_6$-haloalkylthio, C$_3$-C$_6$-cycloalkylthio, C$_3$-C$_6$-halocycloalkylthio, (C$_3$-C$_6$-cycloalkyl)C$_1$-C$_6$-alkylthio, (C$_3$-C$_6$-cycloalkyl)C$_1$-C$_6$-haloalkylthio, (C$_3$-C$_6$-halocycloalkyl)C$_1$-C$_6$-alkylthio, (C$_3$-C$_6$-halocycloalkyl)C$_1$-C$_6$-haloalkylthio, aminocarbonyl-C$_1$-C$_6$-alkylthio, aminocarbonyl-C$_1$-C$_6$-haloalkylthio, N—(C$_1$-C$_6$-alkyl)-aminocarbonyl-C$_1$-C$_6$-alkylthio, N—(C$_1$-C$_6$-haloalkyl)-amino-carbonyl-C$_1$-C$_6$-alkylthio, N—(C$_1$-C$_6$-alkyl)-aminocarbonyl-C$_1$-C$_6$-haloalkylthio, N—(C$_1$-C$_6$-haloalkyl)-aminocarbonyl-C$_1$-C$_6$-haloalkylthio, N,N-di(C$_1$-C$_6$-alkyl)-aminocarbonyl-C$_1$-C$_6$-alkylthio, N,N-di(C$_1$-C$_6$-haloalkyl)-aminocarbonyl-C$_1$-C$_6$-alkylthio, N,N-di(C$_1$-C$_6$-alkyl)-aminocarbonyl-C$_1$-C$_6$-haloalkylthio, N,N-di(C$_1$-C$_6$-haloalkyl)-aminocarbonyl-C$_1$-C$_6$-haloalkylthio, NH$_2$, (C$_1$-C$_6$-alkyl)amino, hydroxyamino, (C$_1$-C$_6$-alkoxy)amino, (C$_3$-C$_6$-cycloalkoxy)amino, (C$_1$-C$_6$-alkyl)sulfinylamino, (C$_1$-C$_6$-alkyl)sulfonylamino, (amino)sulfinylamino, [(C$_1$-C$_6$-alkyl)amino]sulfinylamino, (amino)sulfonylamino, [(C$_1$-C$_6$-alkyl)amino]sulfonylamino, [di(C$_1$-C$_6$-alkyl)amino]sulfonylamino, di(C$_1$-C$_6$-alkyl)amino, (hydroxy)(C$_1$-C$_6$-alkyl)amino, (hydroxy)(C$_1$-C$_6$-cycloalkyl)amino, (C$_1$-C$_6$-alkoxy)(C$_1$-C$_6$-alkyl)amino, (C$_1$-C$_6$-alkoxy)(C$_3$-C$_6$-cycloalkyl)amino, (C$_3$-C$_6$-cycloalkoxy)(C$_1$-C$_6$-alkyl)amino, (C$_3$-C$_6$-cycloalkoxy)(C$_3$-C$_6$-cycloalkyl)amino, [(C$_1$-C$_6$-alkyl)sulfinyl](C$_1$-C$_6$-alkyl)amino, [(C$_1$-C$_6$-alkyl)sulfonyl](C$_1$-C$_6$-alkyl)amino, [di(C$_1$-C$_6$-alkyl)amino]sulfinylamino, [di(C$_1$-C$_6$-alkyl)amino]sulfonylamino, phenyloxy, phenyl-C$_1$-C$_6$-alkoxy, phenylthio, phenyl-C$_1$-C$_6$-alkylthio, phenylamino, (C$_1$-C$_6$-alkyl)(phenyl)amino, (heteroaryl)oxy, heteroaryl-C$_1$-C$_6$-alkoxy, (heterocyclyl)oxy, heterocyclyl-C$_1$-C$_6$-alkoxy, wherein the phenyl, heteroaryl and heterocyclyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^3$ halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkinyl, $C_2$-$C_6$-haloalkinyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkinyloxy, $C_2$-$C_6$-haloalkinyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

and $R^4$, $R^5$, $R^6$ and $R^7$ independently of one another

H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkinyl, $C_2$-$C_6$-haloalkinyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkinyloxy, $C_2$-$C_6$-haloalkinyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

to act on undesired vegetation, harmful plants, their environment or on crop seed.

2. A compound of formula (I),

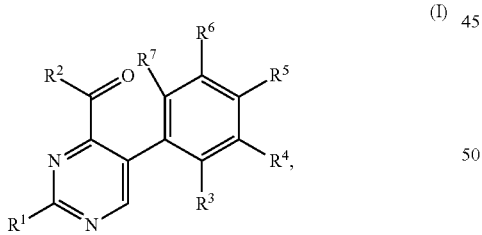

(I)

or an agriculturally acceptable salt or derivative;

$R^1$ is $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkinyloxy, $C_3$-$C_6$-haloalkinyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, 5- or 6-membered heteroaryl, or 3- to 6-membered heterocyclyl wherein the cycloalkyl, heteroaryl and heterocyclyl substituents independently of one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^2$ is H, halogen, $C_1$-$C_6$-alkyl, $C_1$-$C_6$-haloalkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkylcarbonyl-$C_1$-$C_6$-alkyl, $C_1$-$C_6$-haloalkoxycarbonyl-$C_1$-$C_6$-alkyl, $C_1$-$C_6$-alkylcarbonyl-$C_1$-$C_6$-haloalkyl, $C_1$-$C_6$-alkoxycarbonyl-$C_1$-$C_6$-haloalkyl, $C_1$-$C_6$-haloalkylcarbonyl-$C_1$-$C_6$-haloalkyl, $C_1$-$C_6$-haloalkoxycarbonyl-$C_1$-$C_6$-haloalkyl, OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy, $C_1$-$C_6$-haloalkoxy, $C_1$-$C_6$-cyanoalkoxy, $C_1$-$C_6$-hydroxyalkoxy, $C_2$-$C_6$-alkenyloxy, $C_2$-$C_6$-alkenyloxy-$C_1$-$C_6$-alkoxy, $C_2$-$C_6$-haloalkenyloxy-$C_1$-$C_6$-haloalkoxy, $C_2$-$C_6$-alkenyloxy-$C_1$-$C_6$-haloalkoxy, $C_2$-$C_6$-haloalkenyloxy, $C_2$-$C_6$-alkynyloxy, $C_2$-$C_6$-haloalkynyloxy, $C_2$-$C_6$-alkynyloxy-$C_1$-$C_6$-alkoxy, $C_2$-$C_6$-haloalkynyloxy-$C_1$-$C_6$-haloalkoxy, $C_2$-$C_6$-alkynyloxy-$C_1$-$C_6$-haloalkoxy, $C_2$-$C_6$-alkynyloxy-$C_2$-$C_6$-alkenyloxy, $C_2$-$C_6$-haloalkynyloxy-$C_2$-$C_6$-alkenyloxy, $C_2$-$C_6$-alkynyloxy-$C_2$-$C_6$-haloalkenyloxy, $C_2$-$C_6$-haloalkynyloxy-$C_2$-$C_6$-haloalkenyloxy, $C_2$-$C_6$-alkynyloxy-$C_2$-$C_6$-alkynyloxy, $C_2$-$C_6$-haloalkynyloxy-$C_2$-$C_6$-alkynyloxy, $C_2$-$C_6$-alkynyloxy-$C_2$-$C_6$-haloalkynyloxy, $C_2$-$C_6$-haloalkynyloxy-$C_2$-$C_6$-haloalkynyloxy, ($C_1$-$C_6$-alkyl)carbonyl-$C_1$-$C_6$-alkoxy, ($C_1$-$C_6$-haloalkyl)carbonyl-$C_1$-$C_6$-haloalkoxy, ($C_1$-$C_6$-haloalkyl)carbonyl-$C_1$-$C_6$-alkoxy, ($C_1$-$C_6$-alkyl)carbonyl-$C_1$-$C_6$-haloalkoxy, ($C_1$-$C_6$-alkoxy)carbonyl-$C_1$-$C_6$-alkoxy, ($C_1$-$C_6$-haloalkoxy)carbonyl-$C_1$-$C_6$-alkoxy, ($C_1$-$C_6$-alkoxy)carbonyl-$C_1$-$C_6$-haloalkoxy, ($C_1$-$C_6$-haloalkoxy)carbonyl-$C_1$-$C_6$-haloalkoxy, ($C_1$-$C_6$-alkoxy-$C_1$-$C_6$-alkyl)carbonyl-$C_1$-$C_6$-alkoxy, ($C_1$-$C_6$-haloalkoxy-$C_1$-$C_6$-alkyl)carbonyl-$C_1$-$C_6$-alkoxy, ($C_1$-$C_6$-alkoxy-$C_1$-$C_6$-haloalkyl)carbonyl-$C_1$-$C_6$-alkoxy, ($C_1$-$C_6$-alkoxy-$C_1$-$C_6$-alkyl)carbonyl-$C_1$-$C_6$-haloalkoxy, ($C_1$-$C_6$-haloalkoxy-$C_1$-$C_6$-haloalkyl)carbonyl-$C_1$-$C_6$-alkoxy, ($C_1$-$C_6$-haloalkoxy-$C_1$-$C_6$-alkyl)carbonyl-$C_1$-$C_6$-haloalkoxy, ($C_1$-$C_6$-alkoxy-$C_1$-$C_6$-haloalkyl)carbonyl-$C_1$-$C_6$-haloalkoxy, ($C_1$-$C_6$-haloalkoxy-$C_1$-$C_6$-haloalkyl)carbonyl-$C_1$-$C_6$-haloalkoxy, ($C_1$-$C_6$-alkylthio)carbonyl-$C_1$-$C_6$-alkoxy, ($C_1$-$C_6$-haloalkylthio)-carbonyl-$C_1$-$C_6$-alkoxy, ($C_1$-$C_6$-alkylthio)carbonyl-$C_1$-$C_6$-haloalkoxy, ($C_1$-$C_6$-haloalkylthio)carbonyl-$C_1$-$C_6$-haloalkoxy, ($C_1$-$C_6$-alkylthio-$C_1$-$C_6$-alkyl)carbonyl-$C_1$-$C_6$-alkoxy, ($C_1$-$C_6$-haloalkylthio-$C_1$-$C_6$-alkyl)carbonyl-$C_1$-$C_6$-alkoxy, ($C_1$-$C_6$-alkylthio-$C_1$-$C_6$-haloalkyl)carbonyl-$C_1$-$C_6$-alkoxy, ($C_1$-$C_6$-alkylthio-$C_1$-$C_6$-alkyl)carbonyl-$C_1$-$C_6$-haloalkoxy, ($C_1$-$C_6$-haloalkylthio-$C_1$-$C_6$-haloalkyl)carbonyl-$C_1$-$C_6$- alkoxy, ($C_1$-$C_6$-haloalkylthio-$C_1$-$C_6$-alkyl)carbonyl-$C_1$-$C_6$-haloalkoxy, ($C_1$-$C_6$-alkylthio-$C_1$-$C_6$-haloalkyl)carbonyl-$C_1$-$C_6$-haloalkoxy, ($C_1$-$C_6$-haloalkylthio-$C_1$-$C_6$-haloalkyl)carbonyl-$C_1$-$C_6$-haloalkoxy, $C_3$-$C_6$-cycloalkoxy, $C_3$-$C_6$-halocycloalkoxy, ($C_3$-$C_6$-cycloalkyl)$C_1$-$C_6$-alkoxy, ($C_3$-$C_6$-halocycloalkyl)$C_1$-$C_6$-alkoxy, ($C_3$-$C_6$-cycloalkyl)$C_1$-$C_6$-haloalkoxy, aminocarbonyl-$C_1$-$C_6$-alkoxy, ($C_3$-$C_6$-halocycloalkyl)-$C_1$-$C_6$-haloalkoxy, aminocarbonyl-$C_1$-$C_6$-haloalkoxy, N—($C_1$-$C_6$-alkyl)-aminocarbonyl-$C_1$-$C_6$-alkoxy, N—($C_1$-$C_6$-alkyl)-aminocarbonyl-$C_1$-$C_6$-haloalkoxy, N,N-di($C_1$-$C_6$-alkyl)-aminocarbonyl-$C_1$-$C_6$-alkoxy, N,N-di($C_1$-$C_6$-alkyl)-aminocarbonyl-$C_1$-$C_6$-haloalkoxy, O—N=C(di(phenyl), O—N=C(phenyl)($C_1$-$C_6$-alkyl), O—N=C[di($C_1$-$C_6$-alkyl)], ($C_1$-$C_6$-alkyl)$_3$-silyl-$C_1$-$C_6$-alkoxy, $C_1$-$C_6$-alkylthio, $C_1$-$C_6$-haloalkylthio, $C_1$-$C_6$-alkoxy-$C_1$-$C_6$-alkylthio, $C_1$-$C_6$-halo-alkoxy-$C_1$-$C_6$-alkylthio, $C_1$-$C_6$-alkoxy-$C_1$-$C_6$-haloalkylthio, $C_1$-$C_6$-haloalkoxy-$C_1$-$C_6$-haloalkylthio, $C_1$-$C_6$-alkoxy-$C_1$-$C_6$-alkoxy-$C_1$-$C_6$-alkylthio, $C_1$-$C_6$-cyanoalkylthio, $C_2$-$C_6$-alkenylthio, $C_2$-$C_6$-haloalkenylthio, $C_2$-$C_6$-alkenyloxy-$C_1$-$C_6$-alkylthio, $C_2$-$C_6$-haloalkenyloxy-$C_1$-$C_6$-alkylthio, $C_2$-$C_6$-alkenyloxy-$C_1$-$C_6$-haloalkylthio, $C_2$-$C_6$-haloalkenyloxy-$C_1$-$C_6$-haloalkylthio, $C_2$-$C_6$-alkynylthio, $C_2$-$C_6$-haloalkynylthio, $C_2$-$C_6$-alkynyloxy-$C_1$-$C_6$-alkylthio, $C_2$-$C_6$-haloalkynyloxy-$C_1$-$C_6$-haloalkylthio, $C_2$-$C_6$-alkynyloxy-$C_1$-$C_6$-haloalkylthio, $C_2$-$C_6$-alkynyloxy-$C_2$-$C_6$-alkenylthio, $C_2$-$C_6$-haloalkynyloxy-$C_2$-$C_6$-alkenylthio, $C_2$-$C_6$-alkynyloxy-$C_2$-$C_6$-haloalkenylthio, $C_2$-$C_6$-haloalkynyloxy-$C_2$-$C_6$-haloalkenylthio, $C_2$-$C_6$-alkynyloxy-$C_2$-$C_6$-alkynylthio, $C_2$-$C_6$-haloalkynyloxy-$C_2$-$C_6$-alkynylthio, $C_2$-$C_6$-alkynyloxy-$C_2$-$C_6$-haloalkynylthio, $C_2$-$C_6$-haloalkynyloxy-$C_2$-$C_6$-haloalkynylthio, ($C_1$-$C_6$-alkyl)carbonyl-$C_1$-$C_6$-alkylthio, ($C_1$-$C_6$-haloalkyl)carbonyl-$C_1$-$C_6$-alkylthio, ($C_1$-$C_6$-alkyl)carbonyl-$C_1$-$C_6$-haloalkylthio, ($C_1$-$C_6$-haloalkyl)carbonyl-$C_1$-$C_6$-haloalkylthio, ($C_1$-$C_6$-alkoxy)carbonyl-$C_1$-$C_6$-alkylthio, ($C_1$-$C_6$-haloalkoxy)carbonyl-$C_1$-$C_6$-alkylthio, ($C_1$-$C_6$-alkoxy)carbonyl-$C_1$-$C_6$-haloalkylthio, ($C_1$-$C_6$-halo alkoxy)carbonyl-$C_1$-$C_6$-haloalkylthio, ($C_1$-$C_6$-alkoxy-$C_1$-$C_6$-alkyl)carbonyl-$C_1$-$C_6$-alkylthio, ($C_1$-$C_6$-haloalkoxy-$C_1$-$C_6$-alkyl)carbonyl-$C_1$-$C_6$-alkylthio, ($C_1$-$C_6$-alkoxy-$C_1$-$C_6$-haloalkyl)carbonyl-$C_1$-$C_6$-alkylthio, ($C_1$-$C_6$-alkoxy-$C_1$-$C_6$-alkyl)carbonyl-$C_1$-$C_6$-haloalkylthio, ($C_1$-$C_6$-haloalkoxy-$C_1$-$C_6$-haloalkyl)carbonyl-$C_1$-$C_6$-alkylthio, ($C_1$-$C_6$-haloalkoxy-$C_1$-$C_6$-alkyl)carbonyl-$C_1$-$C_6$-haloalkylthio, ($C_1$-$C_6$-alkoxy-$C_1$-$C_6$-haloalkyl)carbonyl-$C_1$-$C_6$-haloalkylthio, ($C_1$-$C_6$-haloalkoxy-$C_1$-$C_6$-haloalkyl)carbonyl-$C_1$-$C_6$-haloalkylthio, ($C_1$-$C_6$-alkylthio)carbonyl-$C_1$-$C_6$-alkylthio, ($C_1$-$C_6$-haloalkylthio)carbonyl-$C_1$-$C_6$-alkylthio, ($C_1$-$C_6$-alkylthio)carbonyl-$C_1$-$C_6$-haloalkylthio, ($C_1$-$C_6$-haloalkylthio)carbonyl-$C_1$-$C_6$-haloalkylthio, ($C_1$-$C_6$-alkylthio-$C_1$-$C_6$-alkyl)carbonyl-$C_1$-$C_6$-alkylthio, ($C_1$-$C_6$-haloalkylthio-$C_1$-$C_6$-alkyl)carbonyl-$C_1$-$C_6$-alkylthio, ($C_1$-$C_6$-alkylthio-$C_1$-$C_6$-haloalkyl)carbonyl-$C_1$-$C_6$-alkylthio, ($C_1$-$C_6$-alkylthio-$C_1$-$C_6$-alkyl)carbonyl-$C_1$-$C_6$-haloalkylthio, ($C_1$-$C_6$-haloalkylthio-$C_1$-$C_6$-haloalkyl)carbonyl-$C_1$-$C_6$-alkylthio, ($C_1$-$C_6$-haloalkylthio-$C_1$-$C_6$-alkyl)carbonyl-$C_1$-$C_6$-haloalkylthio, ($C_1$-$C_6$-alkylthio-$C_1$-$C_6$-haloalkyl)carbonyl-$C_1$-$C_6$-haloalkylthio, ($C_1$-$C_6$-haloalkylthio-$C_1$-$C_6$-haloalkyl)carbonyl-$C_1$-$C_6$-haloalkylthio, $C_3$-$C_6$-cycloalkylthio, $C_3$-$C_6$-halocycloalkylthio, ($C_3$-$C_6$-cycloalkyl)$C_1$-$C_6$-alkylthio, ($C_3$-$C_6$-cycloalkyl)$C_1$-$C_6$-haloalkylthio, ($C_3$-$C_6$-halocycloalkyl)$C_1$-$C_6$-alkylthio, ($C_3$-$C_6$-halocycloalkyl)$C_1$-$C_6$-haloalkylthio, aminocarbonyl-$C_1$-$C_6$-alkylthio, aminocarbonyl-$C_1$-$C_6$-haloalkylthio, N—($C_1$-$C_6$-alkyl)-aminocarbonyl-$C_1$-$C_6$-alkylthio, N—($C_1$-$C_6$-haloalkyl)-amino-carbonyl-$C_1$-$C_6$-alkylthio, N—($C_1$-$C_6$-alkyl)-aminocarbonyl-$C_1$-$C_6$-haloalkylthio, N—($C_1$-$C_6$-haloalkyl)-aminocarbonyl-$C_1$-$C_6$-haloalkylthio, N,N-di($C_1$-$C_6$-alkyl)-aminocarbonyl-$C_1$-$C_6$-alkylthio, N,N-di($C_1$-$C_6$-haloalkyl)-aminocarbonyl-$C_1$-$C_6$-alkylthio, N,N-di($C_1$-$C_6$-alkyl)-aminocarbonyl-$C_1$-$C_6$-haloalkylthio, N,N-di($C_1$-$C_6$-haloalkyl)-aminocarbonyl-$C_1$-$C_6$-haloalkylthio, $NH_2$, ($C_1$-$C_6$-alkyl)amino, hydroxyamino, ($C_1$-$C_6$-alkoxy)amino, ($C_3$-$C_6$-cycloalkoxy)amino, ($C_1$-$C_6$-alkyl) sulfinylamino, ($C_1$-$C_6$-alkyl)sulfonylamino, (amino)sulfinylamino, [($C_1$-$C_6$-alkyl)amino]sulfinylamino, (amino)sulfonylamino, [($C_1$-$C_6$-alkyl)amino]sulfonylamino, [di($C_1$-$C_6$-alkyl)amino]sulfonylamino, di($C_1$-$C_6$-alkyl)amino, (hydroxy)($C_1$-$C_6$-alkyl)amino, (hydroxy)($C_1$-$C_6$-cycloalkyl)amino, ($C_1$-$C_6$-alkoxy)($C_1$-$C_6$-alkyl)amino, ($C_1$-$C_6$-alkoxy)($C_3$-$C_6$-cycloalkyl)amino, ($C_3$-$C_6$-cycloalkoxy)($C_1$-$C_6$-alkyl)amino, ($C_3$-$C_6$-cycloalkoxy)($C_3$-$C_6$-cycloalkyl)amino, [($C_1$-$C_6$-alkyl)sulfinyl]($C_1$-$C_6$-alkyl)amino, [($C_1$-$C_6$-alkyl)sulfonyl]($C_1$-$C_6$-alkyl) amino, [di($C_1$-$C_6$-alkyl)amino]sulfinylamino, [di($C_1$-$C_6$-alkyl)amino]sulfonylamino, phenyloxy, phenyl-$C_1$-$C_6$-alkoxy, phenylthio, phenyl-$C_1$-$C_6$-alkylthio, phenylamino, ($C_1$-$C_6$-alkyl)(phenyl) amino, (heteroaryl)oxy, heteroaryl-$C_1$-$C_6$-alkoxy, (heterocyclyl)oxy, heterocyclyl-$C_1$-$C_6$-alkoxy, wherein the phenyl, heteroaryl and heterocyclyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^3$ is halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkinyl, $C_2$-$C_6$-haloalkinyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkinyloxy, $C_2$-$C_6$-haloalkinyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^4$, $R^6$ and $R^7$ independently of one another are
H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkinyl, $C_2$-$C_6$-haloalkinyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkinyloxy, $C_2$-$C_6$-haloalkinyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl; and $R^5$ is H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkinyl, $C_2$-$C_6$-haloalkinyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkinyloxy, $C_2$-$C_6$-haloalkinyloxy, $C_1$-$C_6$-alkoxy-$C_1$-$C_6$-alkoxy, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents in $R^4$, $R^5$, $R^6$ and $R^7$ independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

provided that in case $R^2$ is OH, $R^2$ is not $C_1$-$C_6$-alkyl or $C_1$-$C_6$-alkoxy.

3. A process for the preparation of the compound of claim 2, wherein a pyrimidine of formula (II)

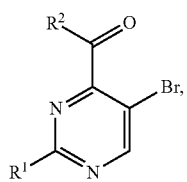

(II)

is reacted with a boronic acid of formula (III)

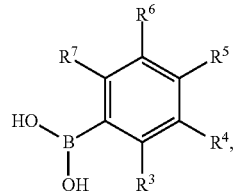

(III)

wherein $R^1$, $R^2$, $R^3$, $R^4$, $R^5$, $R^6$ and $R^7$ are as defined in claim 2.

4. A herbicidal composition comprising a herbicidal active amount of at least one compound of claim 2 and at least one inert liquid and/or solid carrier and, if appropriate, at least one surface-active substance.

5. A method of controlling undesired vegetation, which comprises allowing a herbicidal active amount of a composition according to claim 4 to act on plants, their environment or on seed.

6. A process for the preparation of herbicidal active compositions, which comprises mixing a herbicidal active amount of at least one compound of claim 2 and at least one inert liquid and/or solid carrier and, if desired, at least one surface-active sub stance.

7. A method of controlling undesired vegetation, which comprises allowing a herbicidal active amount of at least one phenylpyrimidine of formula (I) as claimed in claim 2 to act on plants, their environment or on seed.

* * * * *